(12) United States Patent
Mashal et al.

(10) Patent No.: US 11,701,486 B2
(45) Date of Patent: Jul. 18, 2023

(54) PATIENT INTERFACES

(71) Applicant: Fisher & Paykel Healthcare Limited, Auckland (NZ)

(72) Inventors: Fadi Karim Moh'd Mashal, Auckland (NZ); Kirstin Elizabeth Middelkoop, Auckland (NZ); Roheet Patel, Auckland (NZ); Peter David Alexander Bearne, Auckland (NZ); Mark Andrew Thompson, Auckland (NZ); Amit Galgali, Auckland (NZ); Michael John Henri Cox, Auckland (NZ); Gregory James Olsen, Auckland (NZ); Mark Arvind McLaren, Auckland (NZ); Max Leon Betteridge, Auckland (NZ); Bruno Sintive, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 632 days.

(21) Appl. No.: 15/316,814

(22) PCT Filed: Jun. 17, 2015

(86) PCT No.: PCT/IB2015/054560
§ 371 (c)(1),
(2) Date: Dec. 6, 2016

(87) PCT Pub. No.: WO2015/193821
PCT Pub. Date: Dec. 23, 2015

(65) Prior Publication Data
US 2017/0246411 A1    Aug. 31, 2017

Related U.S. Application Data

(60) Provisional application No. 62/013,445, filed on Jun. 17, 2014.

(51) Int. Cl.
*A61M 16/06* (2006.01)

(52) U.S. Cl.
CPC ........ *A61M 16/0605* (2014.02); *A61M 16/06* (2013.01); *A61M 16/0616* (2014.02);
(Continued)

(58) Field of Classification Search
CPC .................................................. A61M 16/0683
See application file for complete search history.

(56) References Cited

U.S. PATENT DOCUMENTS

| 235,643 A | 12/1880 | Nolen |
| 443,191 A | 12/1890 | Illing |

(Continued)

FOREIGN PATENT DOCUMENTS

| AU | 2004201337 A1 | 10/2005 |
| CN | 101378810 | 3/2009 |

(Continued)

OTHER PUBLICATIONS

International Search Report, PCT/IB2015/054560, dated Aug. 10, 2015, in 4 pages.
(Continued)

*Primary Examiner* — LaToya M Louis
(74) *Attorney, Agent, or Firm* — Knobbe Martens Olson and Bear, LLP

(57) ABSTRACT

An interface for positive pressure respiratory therapy includes a mask assembly having a mask seal and a mask shell. The mask assembly is positioned lower than and exposes a bridge of the user's nose. The mask seal includes first and second portions on respective first and second sides of a nasal region that contact opposing sides of the user's nose. The first and second portions each include supports that help maintain a shape of the mask seal. A pair of covers can be supported relative to the mask assembly and adjacent
(Continued)

a respective one of the first and second portions of the mask seal. The covers limit expansion of the first and second portions of the mask seal in response to pressurized air within the mask seal. The supports of the first and second portions can transfer load from the mask seal to the covers.

22 Claims, 37 Drawing Sheets

(52) U.S. Cl.
CPC . *A61M 16/0683* (2013.01); *A61M 2210/0618* (2013.01); *A61M 2210/0625* (2013.01)

(56) References Cited

U.S. PATENT DOCUMENTS

| | | |
|---|---|---|
| 804,272 A | 11/1905 | Schwarz |
| 1,229,050 A | 6/1917 | Donald |
| 1,445,010 A | 2/1923 | Feinberg |
| 2,228,218 A | 1/1941 | Schwartz |
| 2,317,608 A | 4/1943 | Heidbrink |
| 2,353,643 A | 7/1944 | Bulbulian |
| 2,403,046 A | 7/1946 | Bulbulian |
| 2,414,405 A | 1/1947 | Bierman et al. |
| 2,415,846 A | 2/1947 | Eugene |
| 2,444,417 A | 7/1948 | Bierman |
| 2,540,567 A | 2/1951 | Bennett |
| 2,706,983 A | 4/1955 | Matheson et al. |
| 2,867,812 A | 1/1959 | Roth et al. |
| 2,875,757 A | 3/1959 | Galleher |
| 2,931,356 A | 4/1960 | Hermann |
| 2,939,458 A | 6/1960 | Lundquist |
| 3,027,617 A | 4/1962 | Gray |
| 3,040,741 A | 6/1962 | Carolan |
| 3,092,105 A | 6/1963 | Gabb |
| 3,117,574 A | 1/1964 | Replogle |
| 3,170,463 A | 2/1965 | Duggan |
| 3,234,939 A | 2/1966 | Morton |
| 3,234,940 A | 2/1966 | Morton |
| 3,292,618 A | 12/1966 | Davis et al. |
| 3,295,529 A | 1/1967 | Corrigall et al. |
| 3,315,674 A | 4/1967 | Bloom et al. |
| 3,330,273 A | 7/1967 | Bennet |
| 3,330,274 A | 7/1967 | Bennet |
| 3,530,031 A | 9/1970 | Loew |
| 3,599,635 A | 8/1971 | Ansite |
| 3,680,555 A | 8/1972 | Warncke |
| 3,752,157 A | 8/1973 | Malmin |
| 4,263,908 A | 4/1981 | Mizerak |
| 4,384,577 A | 5/1983 | Huber et al. |
| 4,470,413 A | 9/1984 | Warncke |
| 4,603,692 A | 8/1986 | Montesi |
| 4,675,919 A | 6/1987 | Heine et al. |
| 4,764,989 A | 8/1988 | Bourgeois |
| 4,907,584 A | 3/1990 | McGinnis |
| 4,947,488 A | 8/1990 | Ashinoff |
| 4,960,121 A | 10/1990 | Nelson et al. |
| 5,005,571 A | 4/1991 | Dietz |
| 5,243,971 A | 9/1993 | Sullivan et al. |
| 5,265,595 A | 11/1993 | Rudolph |
| 5,323,516 A | 6/1994 | Hartmann |
| 5,441,046 A | 8/1995 | Starr et al. |
| 5,513,634 A | 5/1996 | Jackson |
| 5,517,986 A | 5/1996 | Starr et al. |
| 5,540,223 A | 7/1996 | Starr et al. |
| 5,560,354 A | 10/1996 | Berthon-Jones et al. |
| 5,570,684 A | 11/1996 | Behr |
| 5,570,689 A | 11/1996 | Starr et al. |
| 5,697,363 A | 12/1997 | Hart |
| 5,724,965 A | 3/1998 | Handke et al. |
| 5,832,918 A | 11/1998 | Pantino |
| 5,896,857 A | 4/1999 | Hely et al. |
| 5,934,276 A | 8/1999 | Fabro et al. |
| 6,016,804 A | 1/2000 | Gleason et al. |
| 6,119,694 A | 9/2000 | Correa et al. |
| 6,123,071 A | 9/2000 | Berthon-Jones et al. |
| 6,292,985 B1 | 9/2001 | Grunberger |
| 6,338,342 B1 | 1/2002 | Fecteau et al. |
| 6,341,382 B1 | 1/2002 | Ryvin et al. |
| 6,371,110 B1 | 4/2002 | Peterson et al. |
| 6,374,826 B1 | 4/2002 | Gunaratnam et al. |
| 6,422,238 B1 | 7/2002 | Lithgow |
| 6,467,483 B1 | 10/2002 | Kopacko et al. |
| 6,470,886 B1 | 10/2002 | Jestrabek-Hart |
| 6,491,034 B1 | 12/2002 | Gunaratnam et al. |
| 6,536,435 B1 | 3/2003 | Fecteau et al. |
| 6,584,975 B1 | 7/2003 | Elridge |
| 6,584,977 B1 | 7/2003 | Serowski |
| 6,598,271 B2 | 7/2003 | Nire |
| 6,598,272 B2 | 7/2003 | Nire |
| 6,606,767 B2 | 8/2003 | Wong |
| 6,644,316 B2 | 11/2003 | Bowman et al. |
| 6,647,597 B2 | 11/2003 | Reiter |
| 6,651,663 B2 | 11/2003 | Barnett et al. |
| 6,729,333 B2 | 5/2004 | Barnett et al. |
| 6,823,865 B2 | 11/2004 | Drew et al. |
| 6,823,869 B2 | 11/2004 | Raje et al. |
| 6,851,425 B2 | 2/2005 | Jaffre et al. |
| 6,851,428 B2 | 2/2005 | Dennis |
| 6,892,730 B2 | 5/2005 | Griffiths |
| 6,907,882 B2 | 6/2005 | Ging et al. |
| 6,990,691 B2 | 1/2006 | Klotz et al. |
| 7,000,614 B2 | 2/2006 | Lang et al. |
| 7,063,088 B1 | 6/2006 | Christopher |
| 7,152,602 B2 | 12/2006 | Bateman et al. |
| 7,210,481 B1 | 5/2007 | Lovell et al. |
| 7,260,440 B2 | 8/2007 | Selim et al. |
| 7,296,575 B1 | 11/2007 | Radney |
| 7,318,437 B2 | 1/2008 | Gunaratnam et al. |
| 7,353,826 B2 | 4/2008 | Sleeper |
| 7,448,386 B2 | 11/2008 | Ho et al. |
| 7,509,958 B2 | 3/2009 | Amarisinghe et al. |
| 7,523,754 B2 | 4/2009 | Lithgow et al. |
| 7,556,043 B2 | 7/2009 | Ho et al. |
| 7,562,658 B2 | 7/2009 | Madaus et al. |
| 7,597,100 B2 | 10/2009 | Ging et al. |
| 7,658,189 B2 | 2/2010 | Davidson et al. |
| 7,708,017 B2 | 5/2010 | Davidson et al. |
| 7,721,737 B2 | 5/2010 | Radney |
| 7,762,254 B2 | 7/2010 | Ho |
| 7,793,987 B1 | 9/2010 | Busch et al. |
| 7,810,497 B2 | 10/2010 | Pittman et al. |
| 7,827,990 B1 | 11/2010 | Melidis et al. |
| 7,856,982 B2 | 12/2010 | Matula, Jr. et al. |
| 7,942,148 B2 | 5/2011 | Davidson et al. |
| 7,942,150 B2 | 5/2011 | Guney et al. |
| 7,958,893 B2 | 6/2011 | Lithgow et al. |
| 7,971,590 B2 | 7/2011 | Frater et al. |
| 7,975,694 B2 | 7/2011 | Ho |
| 7,992,560 B2 | 8/2011 | Burton et al. |
| 8,028,699 B2 | 10/2011 | Ho et al. |
| 8,042,538 B2 | 10/2011 | Ging et al. |
| 8,042,539 B2 | 10/2011 | Chandran et al. |
| 8,042,542 B2 | 10/2011 | Ging et al. |
| 8,122,886 B2 | 2/2012 | Kwok et al. |
| 8,127,764 B2 | 3/2012 | Ho et al. |
| 8,132,270 B2 | 3/2012 | Lang et al. |
| 8,136,523 B2 | 3/2012 | Rudolph |
| 8,136,524 B2 | 3/2012 | Ging et al. |
| 8,136,525 B2 | 3/2012 | Lubke et al. |
| 8,146,596 B2 | 4/2012 | Smith et al. |
| 8,146,597 B2 | 4/2012 | Kwok et al. |
| 8,196,583 B2 | 6/2012 | Radney |
| 8,205,615 B1 | 6/2012 | Ho |
| 8,251,066 B1 | 8/2012 | Ho et al. |
| 8,254,637 B2 | 8/2012 | Abourizk et al. |
| 8,261,745 B2 | 9/2012 | Chandran et al. |
| 8,267,089 B2 | 9/2012 | Ho et al. |
| 8,291,906 B2 | 10/2012 | Kooji et al. |
| 8,297,285 B2 | 10/2012 | Henry et al. |
| 8,342,181 B2 | 1/2013 | Selvarajan et al. |
| 8,353,294 B2 | 1/2013 | Frater et al. |
| 8,397,728 B2 | 3/2013 | D'Souza et al. |

(56) References Cited

U.S. PATENT DOCUMENTS

| | | | |
|---|---|---|---|
| 8,439,035 B2 | 5/2013 | Dantanarayana et al. |
| 8,490,623 B2 | 7/2013 | Berthon-Jones et al. |
| 8,490,624 B2 | 7/2013 | Ho et al. |
| 8,550,084 B2 | 10/2013 | Ng et al. |
| 8,573,212 B2 | 11/2013 | Lynch et al. |
| 8,596,271 B2 | 12/2013 | Matula, Jr. et al. |
| 8,616,211 B2 | 12/2013 | Davidson et al. |
| 8,622,057 B2 | 1/2014 | Ujhazy et al. |
| 8,636,007 B2 | 1/2014 | Rummery et al. |
| 8,646,449 B2 | 2/2014 | Bowsher |
| 8,684,004 B2 | 4/2014 | Eifler |
| 8,701,667 B1 | 4/2014 | Ho et al. |
| 8,720,443 B2 | 5/2014 | Kooij et al. |
| 8,733,358 B2 | 5/2014 | Lithgow et al. |
| 8,757,157 B2 | 6/2014 | Price et al. |
| 8,770,190 B2 | 7/2014 | Doherty et al. |
| 8,800,563 B2 | 8/2014 | Doherty et al. |
| 8,807,134 B2 | 8/2014 | Ho et al. |
| 8,856,975 B2 | 10/2014 | Lang et al. |
| 8,857,435 B2 | 10/2014 | Matula, Jr. et al. |
| 8,869,797 B2 | 10/2014 | Davidson et al. |
| 8,875,709 B2 | 11/2014 | Davidson et al. |
| 8,910,626 B2 | 12/2014 | Matula, Jr. et al. |
| 8,931,484 B2 | 1/2015 | Melidis et al. |
| 8,944,061 B2 | 2/2015 | D'Souza et al. |
| 8,950,404 B2 | 2/2015 | Formica et al. |
| 8,967,146 B2 | 3/2015 | Veliss et al. |
| 8,978,653 B2 | 3/2015 | Frater et al. |
| 8,997,742 B2 | 4/2015 | Moore et al. |
| 9,010,330 B2 | 4/2015 | Barlow et al. |
| 9,010,331 B2 | 4/2015 | Lang et al. |
| 9,032,955 B2 | 5/2015 | Lubke et al. |
| 9,044,564 B2 | 6/2015 | Dravitzki et al. |
| 9,056,177 B2 | 6/2015 | Ho |
| 9,067,033 B2 | 6/2015 | Davidson et al. |
| 9,095,673 B2 | 8/2015 | Barlow et al. |
| 9,144,654 B2 | 9/2015 | Kwok |
| 9,149,593 B2 | 10/2015 | Dravitzki et al. |
| 9,149,594 B2 | 10/2015 | Kooij et al. |
| 9,155,857 B2 | 10/2015 | Lalonde |
| 9,174,018 B2 | 11/2015 | Ho et al. |
| 9,220,860 B2 | 12/2015 | Davidson et al. |
| 9,265,909 B2 | 2/2016 | Ho et al. |
| 9,295,805 B2 | 3/2016 | Worboys et al. |
| 9,381,316 B2 | 7/2016 | Ng et al. |
| 9,387,302 B2 | 7/2016 | Dravitzki et al. |
| 9,399,105 B2 | 7/2016 | Frater |
| 9,427,544 B2 | 8/2016 | Frater et al. |
| 9,480,809 B2 | 11/2016 | Guney et al. |
| 9,539,403 B2 | 1/2017 | Eves et al. |
| 9,717,870 B2 | 8/2017 | Kwok et al. |
| 9,737,678 B2 | 8/2017 | Formica et al. |
| 9,757,534 B2 | 9/2017 | Lang et al. |
| 9,764,107 B2 | 9/2017 | Grashow et al. |
| 9,889,267 B2 | 2/2018 | Wells et al. |
| 9,901,701 B2 | 2/2018 | Gunaratnam et al. |
| 9,962,511 B2 | 5/2018 | Ng et al. |
| 9,981,102 B2 | 5/2018 | Veliss et al. |
| 9,993,606 B2 | 6/2018 | Gibson et al. |
| 10,004,867 B2 * | 6/2018 | Henry ............... A61M 16/0683 |
| 10,130,785 B2 | 11/2018 | Dravitzki et al. |
| 10,188,819 B2 | 1/2019 | Chodkowski |
| 10,201,678 B2 | 2/2019 | Guney et al. |
| 10,220,171 B2 | 3/2019 | Olsen et al. |
| 10,265,490 B2 | 4/2019 | Barlow et al. |
| 10,265,492 B2 | 4/2019 | Amarasinghe et al. |
| 10,369,318 B2 | 8/2019 | Barlow et al. |
| 10,589,046 B2 | 3/2020 | Bearne et al. |
| 10,603,456 B2 | 3/2020 | Bearne et al. |
| 2002/0096178 A1 | 7/2002 | Ziaee |
| 2003/0127101 A1 | 7/2003 | Carnell |
| 2003/0172936 A1 | 9/2003 | Wilkie et al. |
| 2003/0196655 A1 | 10/2003 | Ging et al. |
| 2004/0107547 A1 | 6/2004 | Chung |
| 2004/0112377 A1 | 6/2004 | Amarasinghe et al. |
| 2004/0182396 A1 | 9/2004 | Carnell |
| 2005/0028822 A1 | 2/2005 | Sleeper et al. |
| 2005/0056286 A1 | 3/2005 | Huddart et al. |
| 2005/0098183 A1 | 5/2005 | Nash et al. |
| 2005/0121030 A1 | 6/2005 | Bateman et al. |
| 2005/0199239 A1 | 9/2005 | Lang et al. |
| 2006/0042629 A1 | 3/2006 | Geist |
| 2006/0124131 A1 | 6/2006 | Chandran et al. |
| 2006/0174887 A1 | 8/2006 | Chandran et al. |
| 2006/0174892 A1 | 8/2006 | Leksutin et al. |
| 2006/0237017 A1 | 10/2006 | Davidson |
| 2006/0266365 A1 | 11/2006 | Stallard |
| 2006/0283461 A1 | 12/2006 | Lubke et al. |
| 2007/0006879 A1 | 1/2007 | Thonton |
| 2007/0125385 A1 | 6/2007 | Ho et al. |
| 2007/0144525 A1 | 6/2007 | Davidson et al. |
| 2007/0246043 A1 | 10/2007 | Kwok et al. |
| 2008/0041373 A1 | 2/2008 | Doshi et al. |
| 2008/0083412 A1 | 4/2008 | Henry et al. |
| 2008/0190432 A1 | 8/2008 | Blochlinger et al. |
| 2009/0038619 A1 | 2/2009 | Ho et al. |
| 2009/0044808 A1 | 2/2009 | Guney et al. |
| 2009/0107515 A1 | 4/2009 | Gavriely |
| 2009/0114229 A1 | 5/2009 | Frater et al. |
| 2009/0120442 A1 | 5/2009 | Ho |
| 2009/0139526 A1 | 6/2009 | Melidis |
| 2009/0173349 A1 | 7/2009 | Hernandez et al. |
| 2009/0277452 A1 | 11/2009 | Lubke et al. |
| 2010/0000543 A1 | 1/2010 | Berthon-Jones et al. |
| 2010/0000544 A1 | 1/2010 | Blaszczykiewicz |
| 2010/0006101 A1 | 1/2010 | McAuley |
| 2010/0083961 A1 | 4/2010 | McAuley et al. |
| 2010/0132717 A1 | 6/2010 | Davidson et al. |
| 2010/0192955 A1 | 8/2010 | Biener et al. |
| 2010/0218768 A1 | 9/2010 | Radney |
| 2010/0229872 A1 | 9/2010 | Ho |
| 2010/0313891 A1 | 12/2010 | Veliss et al. |
| 2011/0000492 A1 | 1/2011 | Veliss et al. |
| 2011/0067704 A1 | 3/2011 | Kooij et al. |
| 2011/0072553 A1 | 3/2011 | Ho |
| 2011/0146685 A1 | 6/2011 | Allan et al. |
| 2011/0162654 A1 | 7/2011 | Carroll et al. |
| 2011/0265796 A1 | 11/2011 | Amarasinghe et al. |
| 2011/0308526 A1 | 12/2011 | Ho et al. |
| 2011/0315143 A1 | 12/2011 | Frater |
| 2012/0067349 A1 | 3/2012 | Barlow et al. |
| 2012/0080035 A1 | 4/2012 | Guney et al. |
| 2012/0138061 A1 | 6/2012 | Dravitzki et al. |
| 2012/0138063 A1 | 6/2012 | Eves et al. |
| 2012/0152255 A1 | 6/2012 | Barlow et al. |
| 2012/0167892 A1 | 7/2012 | Matula, Jr. |
| 2012/0216819 A1 | 8/2012 | Raje et al. |
| 2012/0234326 A1 | 9/2012 | Mazzone et al. |
| 2012/0304999 A1 | 12/2012 | Swift et al. |
| 2012/0325219 A1 | 12/2012 | Smith |
| 2013/0000648 A1 | 1/2013 | Madaus et al. |
| 2013/0008446 A1 | 1/2013 | Carroll et al. |
| 2013/0037033 A1 | 2/2013 | Hitchcock et al. |
| 2013/0068230 A1 | 3/2013 | Jablonski |
| 2013/0139822 A1 | 6/2013 | Gibson et al. |
| 2013/0152937 A1 | 6/2013 | Jablonski |
| 2013/0199537 A1 | 8/2013 | Formica |
| 2013/0213400 A1 | 8/2013 | Barlow et al. |
| 2013/0220327 A1 | 8/2013 | Barlow et al. |
| 2013/0263858 A1 | 10/2013 | Ho et al. |
| 2013/0306077 A1 | 11/2013 | Greenberg |
| 2013/0319422 A1 | 12/2013 | Ho et al. |
| 2013/0327336 A1 | 12/2013 | Burnham et al. |
| 2014/0026888 A1 | 1/2014 | Matula, Jr. et al. |
| 2014/0034057 A1 | 2/2014 | Todd et al. |
| 2014/0053844 A1 | 2/2014 | Rummery et al. |
| 2014/0069433 A1 | 3/2014 | Walker et al. |
| 2014/0094669 A1 | 4/2014 | Jaffe et al. |
| 2014/0158136 A1 | 6/2014 | Romagnoli et al. |
| 2014/0166018 A1 | 6/2014 | Dravitzki et al. |
| 2014/0166019 A1 | 6/2014 | Ho et al. |
| 2014/0174444 A1 | 6/2014 | Darkin et al. |
| 2014/0174446 A1 | 6/2014 | Prentice |
| 2014/0190486 A1 | 7/2014 | Dunn et al. |

(56) References Cited

U.S. PATENT DOCUMENTS

| | | |
|---|---|---|
| 2014/0202464 A1 | 7/2014 | Lithgow et al. |
| 2014/0209098 A1 | 7/2014 | Dunn et al. |
| 2014/0216462 A1 | 8/2014 | Law et al. |
| 2014/0224253 A1 | 8/2014 | Law et al. |
| 2014/0261412 A1 | 9/2014 | Guney et al. |
| 2014/0261432 A1 | 9/2014 | Eves et al. |
| 2014/0261434 A1 | 9/2014 | Ng et al. |
| 2014/0261435 A1 | 9/2014 | Rothermel |
| 2014/0261440 A1 | 9/2014 | Chodkowski |
| 2014/0283822 A1 | 9/2014 | Price et al. |
| 2014/0283826 A1 | 9/2014 | Murray et al. |
| 2014/0283831 A1 | 9/2014 | Foote et al. |
| 2014/0283841 A1 | 9/2014 | Chodkowski et al. |
| 2014/0283842 A1 | 9/2014 | Bearne et al. |
| 2014/0283843 A1 | 9/2014 | Eves et al. |
| 2014/0305439 A1 | 10/2014 | Chodkowski et al. |
| 2014/0311494 A1 | 10/2014 | Gibson et al. |
| 2014/0326243 A1 | 11/2014 | Znamenskiy et al. |
| 2014/0326246 A1 | 11/2014 | Chodkowski et al. |
| 2014/0352134 A1 | 12/2014 | Ho |
| 2014/0360503 A1 | 12/2014 | Franklin et al. |
| 2015/0007822 A1 | 1/2015 | Berthon-Jones et al. |
| 2015/0028519 A1 | 1/2015 | Lang et al. |
| 2015/0040911 A1 | 2/2015 | Davidson et al. |
| 2015/0047640 A1 | 2/2015 | McCaslin |
| 2015/0059759 A1 | 3/2015 | Frater et al. |
| 2015/0083124 A1 | 3/2015 | Chodkowski et al. |
| 2015/0105590 A1 | 4/2015 | Xiao |
| 2015/0128952 A1 | 5/2015 | Matula, Jr. et al. |
| 2015/0128953 A1 | 5/2015 | Formica et al. |
| 2015/0144139 A1 | 5/2015 | Lockhart |
| 2015/0174435 A1 | 6/2015 | Jones |
| 2015/0182719 A1 | 7/2015 | Grashow et al. |
| 2015/0193650 A1 | 7/2015 | Ho et al. |
| 2015/0196726 A1 | 7/2015 | Skipper et al. |
| 2015/0246199 A1 | 9/2015 | Matula, Jr. et al. |
| 2015/0290415 A1 | 10/2015 | Dunn |
| 2015/0352306 A1 | 12/2015 | Scheiner |
| 2015/0352308 A1 | 12/2015 | Cullen et al. |
| 2016/0001029 A1 | 1/2016 | Bayer et al. |
| 2016/0022944 A1* | 1/2016 | Chodkowski ..... A61M 16/0616 128/206.24 |
| 2016/0074613 A1 | 3/2016 | Davidson et al. |
| 2016/0082214 A1 | 3/2016 | Barlow et al. |
| 2016/0082216 A1 | 3/2016 | Lynch et al. |
| 2016/0175552 A1 | 6/2016 | Harrington |
| 2016/0184544 A1 | 6/2016 | Patel et al. |
| 2016/0271351 A1 | 9/2016 | Frater et al. |
| 2016/0296720 A1 | 10/2016 | Edward et al. |
| 2016/0367778 A1 | 12/2016 | Eves et al. |
| 2017/0000964 A1 | 1/2017 | Shafer |
| 2017/0021123 A1 | 1/2017 | Chang |
| 2017/0028153 A1 | 2/2017 | Judson et al. |
| 2017/0080174 A1 | 3/2017 | Eves et al. |
| 2017/0136200 A1 | 5/2017 | Matula, Jr. |
| 2017/0165444 A1 | 6/2017 | Rummery et al. |
| 2017/0182273 A1 | 6/2017 | Ho |
| 2017/0312467 A1 | 11/2017 | Davidson et al. |
| 2017/0326321 A1 | 11/2017 | Grashow et al. |
| 2017/0361048 A1 | 12/2017 | Moiler et al. |
| 2017/0368286 A1 | 12/2017 | Grashow et al. |
| 2018/0001044 A1 | 1/2018 | Stephens et al. |
| 2018/0071475 A1 | 3/2018 | Howard et al. |
| 2018/0099113 A1 | 4/2018 | Bell et al. |
| 2018/0104430 A1 | 4/2018 | Ng et al. |
| 2018/0140791 A1 | 5/2018 | Jones et al. |
| 2018/0169367 A1 | 6/2018 | Chodkowski et al. |
| 2018/0236198 A1 | 8/2018 | Veliss et al. |
| 2018/0250486 A1 | 9/2018 | Amarasinghe et al. |

FOREIGN PATENT DOCUMENTS

| | | |
|---|---|---|
| CN | 102698349 | 10/2012 |
| CN | 103619393 | 3/2014 |
| DE | 3719009 | 12/1988 |
| DE | 4004157 | 4/1991 |
| DE | 4307754 | 4/1994 |
| EP | 1099452 | 5/2001 |
| EP | 1163923 | 12/2001 |
| EP | 1258266 | 11/2002 |
| EP | 1938856 | 7/2008 |
| EP | 2060294 | 5/2009 |
| EP | 2130563 | 12/2009 |
| EP | 2417994 | 2/2012 |
| EP | 2452716 | 5/2012 |
| EP | 2470246 | 7/2012 |
| EP | 2474335 | 7/2012 |
| EP | 2510968 | 10/2012 |
| EP | 3254721 | 12/2017 |
| EP | 3305354 | 4/2018 |
| FR | 2390116 | 12/1978 |
| GB | 472897 | 9/1937 |
| GB | 521282 | 5/1940 |
| GB | 960115 | 6/1964 |
| GB | 1072741 | 6/1967 |
| GB | 2385533 | 8/2003 |
| GB | 2393126 | 3/2004 |
| JP | 2007-516750 | 6/2007 |
| JP | 2008-525123 | 7/2008 |
| JP | 2011-512967 | 4/2011 |
| JP | 2011-200744 | 10/2011 |
| JP | 2012-511371 | 5/2012 |
| JP | 2012-530561 | 12/2012 |
| NZ | 536545 | 12/2006 |
| NZ | 547748 | 7/2010 |
| WO | WO 94/02190 | 2/1994 |
| WO | WO 1998/034665 | 8/1998 |
| WO | WO 99/006116 | 2/1999 |
| WO | WO 00/38772 | 7/2000 |
| WO | WO 00/050122 | 8/2000 |
| WO | WO 2000/074758 | 12/2000 |
| WO | WO 2001/062326 | 8/2001 |
| WO | WO 02/07806 | 1/2002 |
| WO | WO 02/047749 | 6/2002 |
| WO | WO 03/013657 | 2/2003 |
| WO | WO 03/039637 | 5/2003 |
| WO | WO 2003/076020 | 9/2003 |
| WO | WO 2003/090827 | 11/2003 |
| WO | WO 2004/041325 | 5/2004 |
| WO | WO 2004/071565 | 8/2004 |
| WO | WO 2004/073778 | 9/2004 |
| WO | WO 2005/018523 | 3/2005 |
| WO | WO 2005/032634 | 4/2005 |
| WO | WO 2005/063328 | 7/2005 |
| WO | WO 2005/076874 | 8/2005 |
| WO | WO 2005/086943 | 9/2005 |
| WO | WO 2005/118040 | 12/2005 |
| WO | WO 2005/118042 | 12/2005 |
| WO | WO 2006/130903 | 12/2006 |
| WO | WO 2007/012145 | 2/2007 |
| WO | WO 2007/143792 | 12/2007 |
| WO | WO 2008/023028 | 2/2008 |
| WO | WO 2008/030831 | 3/2008 |
| WO | WO 2008/063923 | 5/2008 |
| WO | WO 2009/026627 | 3/2009 |
| WO | WO 2009/059353 | 5/2009 |
| WO | WO 2009/065368 | 5/2009 |
| WO | WO 2009/143586 | 12/2009 |
| WO | WO 2010/066004 | 6/2010 |
| WO | WO 2010/067235 | 6/2010 |
| WO | WO 2010/073138 | 7/2010 |
| WO | WO 2010/073142 | 7/2010 |
| WO | WO 2010/139014 | 12/2010 |
| WO | WO 2011/060479 | 5/2011 |
| WO | WO 2012/025843 | 3/2012 |
| WO | WO 2012/040791 | 4/2012 |
| WO | WO 2012/040792 | 4/2012 |
| WO | WO 2012/045127 | 4/2012 |
| WO | WO 2012/055886 | 5/2012 |
| WO | WO 2013/056389 | 4/2013 |
| WO | WO 2013/066195 | 5/2013 |
| WO | WO 2013/128324 | 9/2013 |
| WO | WO 2013/142909 | 10/2013 |

(56) References Cited

FOREIGN PATENT DOCUMENTS

| WO | WO 2013/175409 | 11/2013 |
|---|---|---|
| WO | WO 2013/186654 | 12/2013 |
| WO | WO 2014/020468 | 2/2014 |
| WO | WO 2014/021722 | 2/2014 |
| WO | WO 2014/025267 | 2/2014 |
| WO | WO 2014/045136 | 3/2014 |
| WO | WO 2014/045245 | 3/2014 |
| WO | WO 2014/062070 | 4/2014 |
| WO | WO 2014/077708 | 5/2014 |
| WO | WO 2014/110622 | 7/2014 |
| WO | WO 2014/141029 | 9/2014 |
| WO | WO 2014/165906 | 10/2014 |
| WO | WO 2014/175753 | 10/2014 |
| WO | WO 2014/177972 | 11/2014 |
| WO | WO 2014/181214 | 11/2014 |
| WO | WO 2014/183167 | 11/2014 |
| WO | WO 2015/006826 | 1/2015 |
| WO | WO 2015/020535 | 2/2015 |
| WO | WO 2015/068067 | 5/2015 |
| WO | WO 2015/070289 | 5/2015 |
| WO | WO 2015/092621 | 6/2015 |
| WO | WO 2015/131262 | 9/2015 |
| WO | WO 2015/161345 | 10/2015 |
| WO | WO 2016/000040 | 1/2016 |
| WO | WO 2016/041008 | 3/2016 |
| WO | WO 2016/041019 | 3/2016 |
| WO | WO 2016/075658 | 5/2016 |
| WO | WO 2017/049361 | 3/2017 |
| WO | WO 2017/103724 | 6/2017 |
| WO | WO 2017/120643 | 7/2017 |
| WO | WO 2017/124152 | 7/2017 |
| WO | WO 2017/185140 | 11/2017 |
| WO | WO 2018/064712 | 4/2018 |
| WO | WO 2018/177794 | 10/2018 |

OTHER PUBLICATIONS

Official Action, Chinese Patent Office, Application No. 2016-571708, dated Feb. 28, 2019, in 3 pages.
Examination Report No. 1, Australian Government IP, Application No. 2015-275705, dated Feb. 25, 2019, in 4 pages.
Extended European Search Report, PCT/IB2015/054560, dated Jan. 22, 2018, in 7 pages.
Chinese Office Action, Application No. 201580024907.4, dated Apr. 28, 2018, in 8 pages.
U.S. Appl. No. 14/354,550, filed Apr. 25, 2017, Beane et al.
U.S. Appl. No. 14/907,135, filed Jan. 22, 2016, Patel et al.
Amara View brochure, Respironics, 2015; product believed to have been available prior to Sep. 2015.
Australian Government, IP Australia, Examination Report No. 1 for Standard Patent Application No. 2014305231 dated Jan. 18, 2018 in 9 pgs.
Australian Government IP Australia, Examination Report No. 1 for Standard Patent Application No. 2013332513 dated Mar. 28, 2017 in 3 pgs.
Australian Examination Report No. 1 for Application No. 2019261711 dated Jun. 12, 2020 in 4 pgs.
Brad T Miller, B. et al., A Head-And-Face Anthropometric Survey of U.S. Respirator Users, Final Report by Anthrotech, May 28, 2004 [retrieved from internet on Oct. 28, 2016].
Chinese Notification of the First Office Action, Application No. 201480044460.2, dated Feb. 27, 2017 in 15 pages.
European Patent Office Examination Report for Application No. 14835244.6 dated Feb. 14, 2019 in 8 pgs.
European Patent Office Examination Report, Application No. 13847504.1 dated Apr. 13, 2017 in 4 pgs.
European Patent Office, European Search Report for Application No. 14835244.6 dated Dec. 20, 2016, in 14 pages.
Extended European Search Report for EP Appl. No. 16840943.1 dated Mar. 26, 2019 in 8 pages.
Examination Report, Great Britain Application No. GB1602009.1, dated Aug. 1, 2019, in 4 pages.
Examination Report, Great Britain Application No. GB1602009.1, dated Dec. 19, 2019, in 4 pages.
Hsiao, H., Anthropometric Procedures for Protective Equipment Sizing and Design, Human Factors: The Journal of the Human Factors and Ergonomics Society, 55(1):6-35, Feb. 2013.
Japanese Patent Office, Official Action for Application No. 2015-537658 dated Aug. 23, 2017 in 5 pgs.
Lee, W. et al., Analysis of the Facial Measurements of Korean Air Force pilots for Oxygen Mask Design, Ergonomics, 56(9): 1451-64, 2013.
Los Alamos Scientific Laboratory Respirator and Research and Development Section, Selection of Respirator Test Panels Representative of U.S. Adult Facial Sizes, Dec. 1973 [retrieved from internet on Oct. 28, 2016].
Extended European Search Report from EP 17857947.0 May 4, 2020 in 9 pgs.
International Search Report for PCT Application No. PCT/NZ2013/000189 dated Dec. 2, 2013.
International Search Report and Written Opinion for PCT/NZ2014/000158 dated Nov. 19, 2014 in 30 pgs.
International Search Report and Written Opinion for PCT/IB2016/055212 dated Oct. 31, 2016.
International Search Report for PCT Application No. PCT/IB2017/056136 dated Feb. 2, 2018 in 7 pages.
"International Standard ISO 17510-2 Sleep apnoea breathing therapy—Part 2: Masks and application accessories".
Japanese Office Action for Application No. 2016-533273 dated Jun. 19, 2018 in 5 pgs.
Japanese Office Action for Application No. 2016-533273 dated May 24, 2019 in 4 pgs.
Written Opinion received from Intellectual Property of Singapore for Application No. 11201600431P dated Jun. 12, 2017.
Zhuang, Z. et al., Facial Anthropometric Differences among Gender, Ethnicity and Age Groups, The Annals of Occupational Hygiene, 54(4):391-402, Jun. 2010.
Japanese Patent Office, Notice of Reasons for Refusal, Application No. JP 2019-231100, dated Jan. 20, 2021, in 6 pages.
Australian Examination Report for Application No. 2020200999, dated Jul. 13, 2020, in 5 pages.

* cited by examiner

PATIENT INTERFACES

INCORPORATION BY REFERENCE TO ANY PRIORITY APPLICATIONS

Any and all applications for which a foreign or domestic priority claim is identified in connection with the present application are hereby incorporated by reference herein and made a part of the present disclosure.

BACKGROUND

Field

The present disclosure relates to interface assemblies for respiratory therapy. In particular, the present disclosure relates to under-nose interface assemblies that do not cover the bridge of the user's nose.

Description of Related Art

In patients suffering from obstructive sleep apnea (OSA), muscles that normally keep the upper airway open relax during slumber to the extent that the airway is constrained or completely closed off, a phenomenon often manifesting itself in the form of snoring. When this occurs for a period of time, the patient's brain typically recognizes the threat of hypoxia and partially wakes the patient in order to open the airway so that normal breathing may resume. The patient may be unaware of these waking episodes, which may occur as many as several hundred times per session of sleep. This partial awakening may significantly reduce the quality of the patient's sleep, over time potentially leading to a variety of symptoms, including excessive daytime sleepiness, chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that will reduce the frequency and/or duration of apneas, hypopneas, and/or flow limitations. The therapy is often implemented by using a positive airway pressure device to deliver a pressurized stream of air through a conduit to a patient through a patient interface or mask positioned on the face of the patient.

One common type of patient interface assembly used with PAP therapy or other respiratory therapies involving the administration of gas includes a seal that contacts the bridge of the nose of a user of the interface assembly. The bride of the nose is sensitive to pressure applied by the seal of the interface assembly. More recently, interface assemblies have become available that do not contact the bridge of the nose. Such interface assemblies can be referred to as "under-nose" interface assemblies. A need exists to provide improved under-nose interface assemblies with improved comfort and/or sealing performance, or to provide the public with a useful choice.

SUMMARY

The systems, methods and devices described herein have innovative aspects, no single one of which is indispensable or solely responsible for their desirable attributes. Without limiting the scope of the claims, some of the advantageous features will now be summarized.

In some configurations, an interface for use in providing positive pressure respiratory therapy comprises a mask assembly having a mask seal and a mask shell. The mask assembly is configured to be fully positioned lower than a bridge of a nose of a face of a user and to provide an exposed bridge of the nose of the user. The mask seal is connected to the mask shell. The mask seal comprises a nasal region comprising at least one nasal opening. The mask seal comprises a first paddle on a first side of the nasal region and a second paddle on a second side of the nasal region. The first paddle is configured to contact one side of the nose of the user and the second paddle is configured to contact the other side of the nose of the user. A frame is removably coupled to the mask assembly. A pair of covers is supported relative to the mask assembly such that each of the covers is positioned adjacent a portion of a respective one of the first and second paddles. The covers limit expansion of at least the portion of the first and second paddles.

In some configurations, the covers are supported by the frame. In some configurations, the covers are unitarily formed with the frame.

In some configurations, the covers are positioned adjacent only a portion of the paddles leaving a portion of the paddles exposed. In some configurations, a rearward portion of the paddles are left exposed by the covers.

In some configurations, the paddles cover a substantial entirety of a height of an adjacent portion of the paddles.

In some configurations, the paddles define a space therebetween, which exposes a portion of an upper portion of the mask seal.

In some configurations, the covers are formed as part of the mask seal, wherein each of the covers comprises a flap portion extending from the mask seal adjacent a respective one of the paddles.

In some configurations, the seal comprises at least one living hinge adjacent and below the paddles. The living hinge is configured to allow flexing of the paddles inward toward the nose of the user and resist flexing of the paddles outward away from the nose of the user. In some configurations, the living hinge comprises a thinned portion of the seal adjacent the paddles.

In some configurations, the covers are configured to pivot relative to the mask assembly. In some configurations, an adjustment mechanism configured to permit adjustment of a pivoting of the covers relative to the mask assembly.

In some configurations, the covers are removably attachable to the frame or to the mask assembly.

In some configurations, the covers are adjustable relative to the mask assembly.

In some configurations, a height of the covers relative to the mask assembly is adjustable.

In some configurations, the interface further comprises a headgear. The headgear comprises an upper strap and a lower strap on each side of the mask assembly. The headgear is removably connected to the frame. The upper straps of the headgear movably support the covers such that the covers can slide along the upper straps.

In some configurations, the covers are formed as part of the mask shell and extend upward along the mask seal adjacent the paddles.

In some configurations, a tether extends from one side of the mask assembly to the other side of the mask assembly and the tether defines the covers.

In some configurations, each of the paddles comprises a support in the form of a suspension member, which assists in maintaining a desired shape of the paddles.

In some configurations, the suspension members comprise elongate, thickened areas of the mask seal that extend toward the frame from a patient side of the mask assembly.

In some configurations, the suspension members are thicker than other portions of the mask seal in the paddles and the nasal region.

In some configurations, each of the suspension members is aligned with a respective one of the covers and is configured to transfer load from the seal to the covers via the suspension member.

In some configurations, the suspension members are connected to one another.

In some configurations, a mask assembly for use in providing positive pressure respiratory therapy includes a mask seal and a mask shell. The mask assembly is configured to be fully positioned lower than a bridge of a nose of a face of a user and to provide an exposed bridge of the nose of the user. The mask seal is connected to the mask shell. The mask seal comprises a nasal region comprising at least one nasal opening. The mask seal comprises a first paddle on a first side of the nasal region and a second paddle on a second side of the nasal region. The first paddle is configured to contact one side of the nose of the user and the second paddle is configured to contact the other side of the nose of the user. The mask seal varies in thickness and each of the paddles comprises a support in the form of a suspension member, which assists in maintaining a desired shape of the paddles.

In some configurations, the nasal region has the smallest thickness of the mask seal In some configurations, the supports of the paddles have the largest thickness of the mask seal.

In some configurations, the suspension members extend from a user-contacting surface of the mask seal toward the mask shell.

In some configurations, the suspension members are connected to one another to form a connected area of increased thickness.

In some configurations, the mask seal further comprises an oral opening, wherein a region surrounding the oral opening has the smallest thickness or equals the smallest thickness of the mask seal.

In some configurations, the mask seal further comprises outer peripheral portions on either side of the oral opening, wherein each of the outer peripheral portions wrap from a rear-facing side of the mask seal around to at least a portion of a laterally-facing side of the mask seal. The outer peripheral portions have a thickness that is greater than the thickness of the nasal region.

In some configurations, the supports comprise a generally triangular shape with a base of the triangle positioned rearwardly of a tip of the triangle.

In some configurations, an interface assembly comprises any one of the above-described mask assemblies, wherein the interface assembly further comprises a removably attachable frame, wherein the frame comprises one or more covers that extend from the frame and are configured to prevent the mask seal from expanding outwardly and losing shape when pressurized air is introduced into the mask seal.

In some configurations, each of the suspension members is aligned with a respective one of the covers and is configured to transfer load from the seal to the covers via the suspension member.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

DETAILED DESCRIPTION

Figure 1:
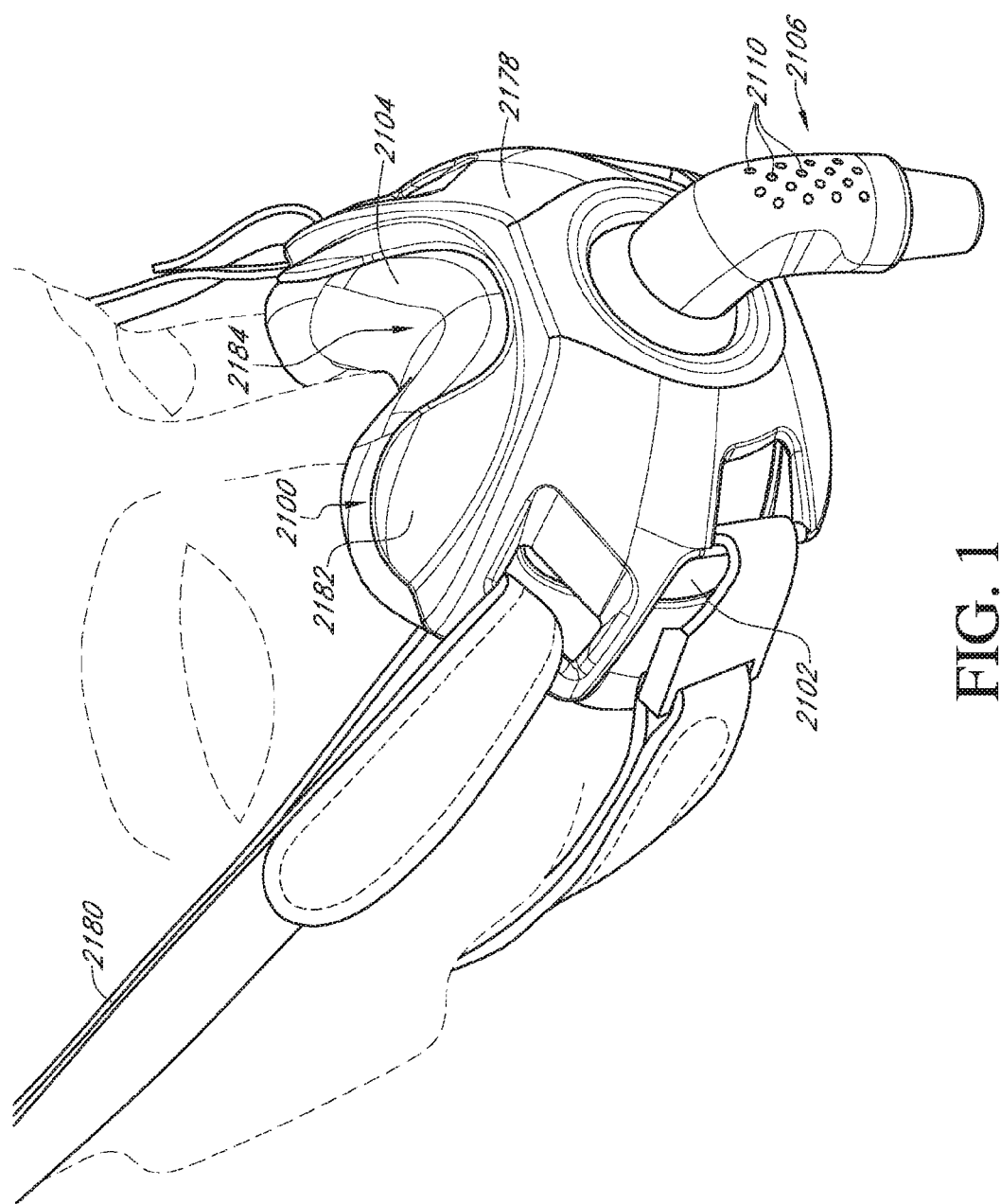
FIG. 1 is a front perspective view of an interface assembly having certain features, aspects and advantages of the present disclosure positioned on the head of a user.
Figure 2:
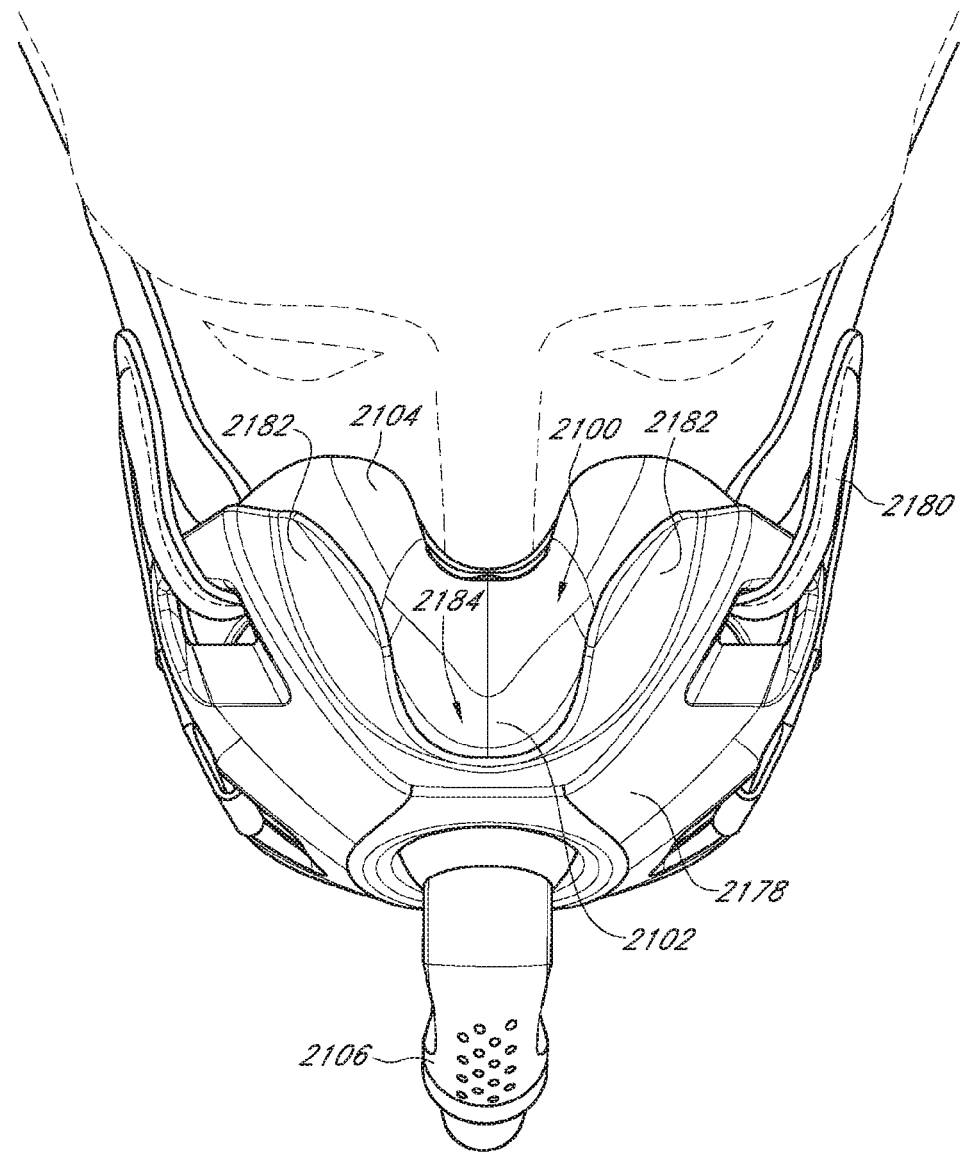
FIG. 2 is a top view of the interface assembly of FIG. 1 positioned on the head of a user.
Figure 3:
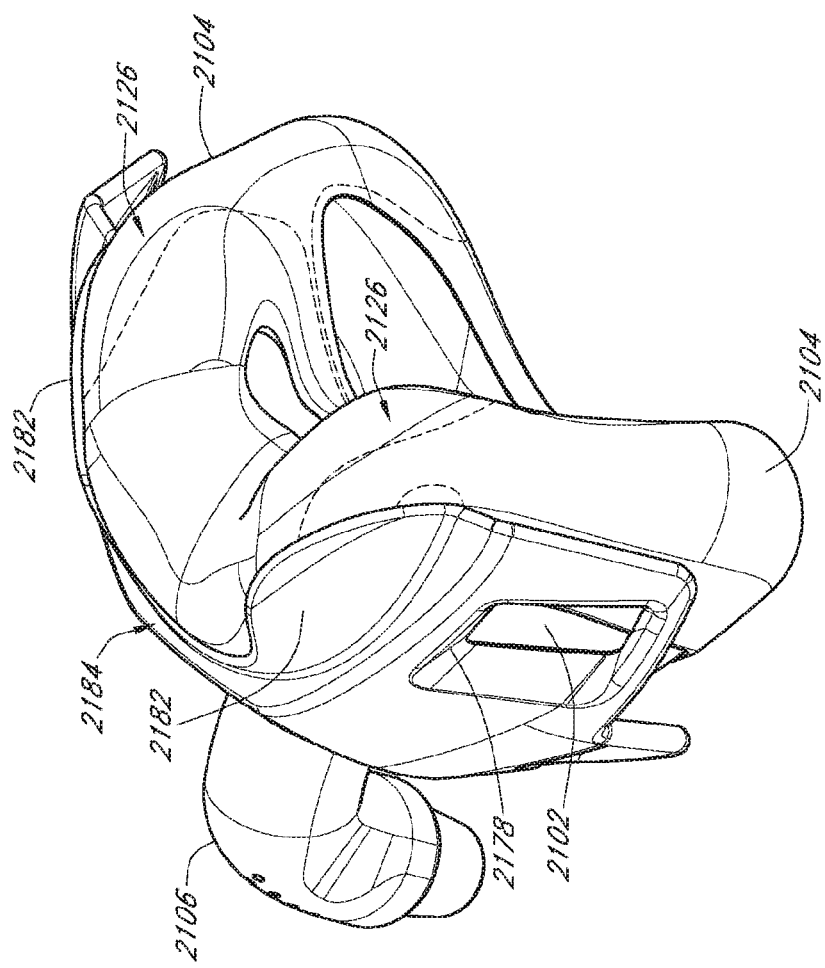
FIG. 3 is rear perspective view of an interface portion of the interface assembly of FIG. 1 separated from the user and without headgear.
Figure 4:
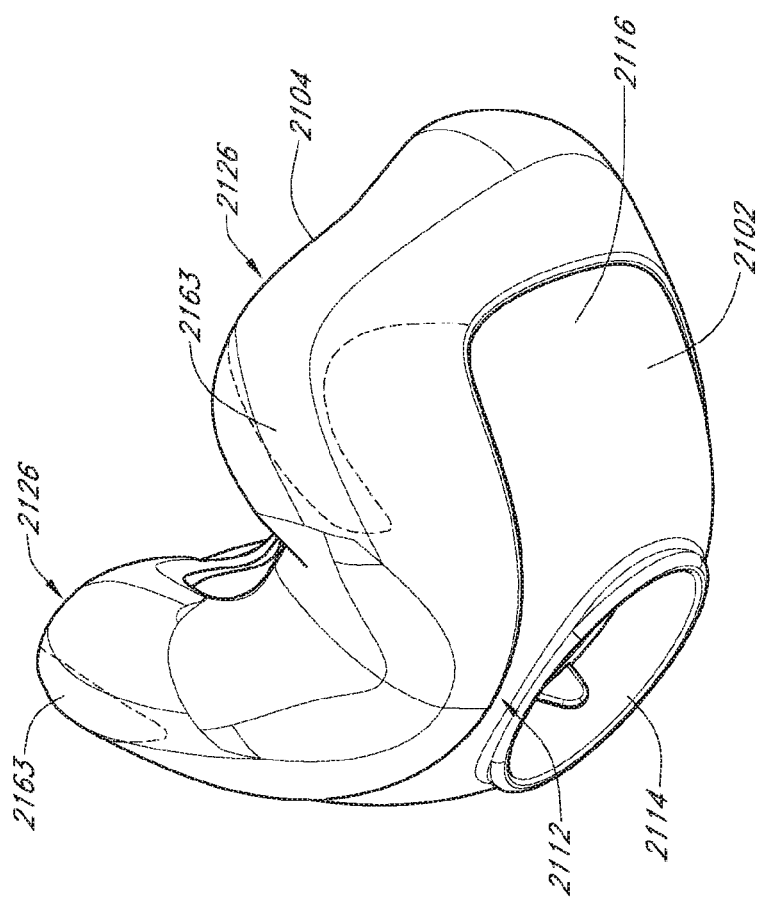
FIG. 4 is a front perspective view of a mask assembly of the interface assembly of FIG. 1.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

One or more of the embodiments described herein address issues with stability that can be experienced with face masks. In particular, at least some of the embodiments are directed toward patient interfaces, such as face masks, which seal below the bridge of the user's nose and around the nares. However, the embodiments disclosed herein could also be adapted to other full face masks (e.g., those that partially cover and/or seal on the bridge of the user's nose). Most full face masks have a forehead rest, headgear mount or 'T' piece which extends upwardly from the remainder of the mask and rests on the forehead and adds significant stability compared to those full face masks without 'T' pieces. Instability can cause nose tip or septum pressure and/or seal leaks due to forces applied by the breathing tube of the breathing circuit that is attached to the mask or other patient interface. This force is often referred to as "hose pull" and can originate from the breathing circuit or tube or from movement of the user.

The embodiments illustrated herein have no T piece and seal below the bridge of the nose, around the nares and under the nose. In at least some configurations, the interface or mask also seals around the user's mouth. The reduced foot print of an under-nose combined nasal and oral mask on the user's face compared to conventional full face masks that contact the nasal bridge and/or have a T piece can have an adverse effect on stability. Similarly, the reduced foot print of an under-nose nasal mask on the user's face compared to conventional nasal mask that contact the nasal bridge and/or have a T piece can also have an adverse effect on stability. Sealing around and below the nose in this manner can present challenges due to the variation seen in facial geometries from user to user. In some circumstances, even small movements of the seal can induce loss of contact of the seal with the user, which can result in leaks.

FIGS. 1-24 illustrate a mask assembly 2100 both in position on a face of a user and separated from the face of the user. The illustrated mask assembly 2100 is a combined nasal and oral mask, which can be referred to herein as a nasal-oral mask. The illustrated mask assembly 2100 is designed to seal under the nose of the user, along a portion of the face extending lateral to the nose, as well as around the mouth of the user. The mask assembly 2100 advantageously does not require contact with the bridge of the nose of the user. In the illustrated configuration, the mask assembly 2100 does not extend over the bridge of the nose of the user. More particularly, the illustrated mask assembly 2100 does not contact the bridge of the nose of the user. Even more particularly, the illustrated assembly 2100 does not contact a forward facing portion of the bridge of the nose of the user. In some configurations, the assembly 2100 does not contact the face in a region vertically higher than a generally horizontal plane extending along the lower edges of the eyes of the user. The mask assembly 2100 may or may not extend over the tip of the nose of the user. Thus, in some configurations, the mask assembly 2100 covers the tip of the nose. In some configurations, the seal of the mask assembly 2100 covers the tip of the nose. In some configurations, the illustrated mask assembly 2100 preferably does not enshroud the tip of the nose of the user. In some configurations or with some facial geometries, the tip of the nose of the user extends over the adjoining portion of the mask assembly 2100.

As illustrated, the mask assembly 2100 preferably is adapted to extend around and seal over the wing or alar of the nose, which flares out to form a rounded eminence around the nostril. The illustrated mask assembly 2100 is adapted to seal around the surfaces that define the opening to the nostril, which may include a portion or entirety of the fleshy external end of the nasal septum, sometimes called the columella. In some configurations, the mask assembly 2100 is adapted to extend upwardly to seal along at least a portion of the left and right dorsal side walls of the nose of the user. In some configurations, the mask assembly 2100 is adapted to extend upwardly along at least a portion of the left and right dorsal side walls without extending upwardly to the region of the bridge of the nose of the user. In some configurations, a primary sealing surface of the mask assembly 2100 contacts the underside of the nose of the user, possibly along with the upper lip and/or a transition region between the underside of the nose and the upper lip. A secondary sealing surface of the mask can contact the side surfaces of the nose of the user, possibly along with the cheeks at a location near the nose. Such primary and secondary sealing surfaces may not make contact with the face of all users, however, such an arrangement can provide a suitable seal with a relatively large range of facial geometries. The mask assembly 2100 preferably also seals around at least a portion of the user's mouth. The mask assembly 2100 may or may not be adapted to seal between the mouth and nose of the user.

As illustrated, the mask assembly 2100 comprises a mask support, such as a base, housing or shell 2102 (see, for example, FIG. 5), for example. A mask seal 2104 can be attached to the mask shell 2102 such that the mask shell 2102 provides some amount of support for the mask seal 2104. However, in other configurations, the mask seal 2104 may not include a support and may be adapted for direct assembly to another component of the associated interface assembly. In some configurations, the mask support 2102 can be substantially smaller than the illustrated shell. For example, the mask support 2102 can define an opening that allows the mask assembly 2100 to be attached to another component, such as a frame and/or conduit connector (e.g., elbow) and the mask support 2102 can be localized to the opening without providing direct support to other portions of the mask assembly 2100.

The mask assembly 2100 can be engaged with or otherwise supported by a frame 2178 that allows for connection to a head strap or headgear 2180 of any suitable arrangement. The mask assembly 2100 can be keyed to the frame 2178 to permit assembly in only the correct orientation. In some configurations, the head strap or headgear 2180 could be coupled directly to the mask assembly 2100 and the frame 2178 can be utilized for other purposes or omitted. A conduit connector 2106 can also be attached to the mask shell 2102, frame 2178 or otherwise supported relative to and adapted to communicate with an interior space of the mask assembly 2100. Together, the frame 2178 and the headgear 2180 can support the mask assembly 2100 in place on the user's face. Collectively, the mask assembly 2100, frame 2178 and headgear 2180 can be referred to as an interface assembly. The mask assembly 2100 or the mask assembly 2100 in combination with the frame 2178 can be referred to as an interface.

The illustrated conduit connector 2106 can be connected to the frame 2178 and/or shell 2102 in any suitable manner, including but not limited to any manner discussed elsewhere within this application. For example, but without limitation, the connector 2106 can be connected to the shell 2102 such that the connector 2106 can swivel, pivot or rotate relative to the shell 2102 about a single axis or about multiple axes.

In some configurations, the connector 2106 can define a portion of a ball joint with the frame 2178 and/or mask shell 2102, for example but without limitation, defining the other portion. The ball joint can have any suitable configuration. The connector 2106 facilitates connection to a gases conduit, such as a supply conduit or the like for the supply of pressurized breathing gases to an interior of the mask assembly 2100. Any suitable connector 2106 can be used, which in some cases can include a swivel or rotational coupling that permits relative rotation between the connector 2106 and the gases conduit.

In the illustrated configuration, the connector 2106 comprises an elbow, such as a polycarbonate elbow for example but without limitation, that contains a vent. In the illustrated arrangement, the vent comprises bias flow holes 2110. However, the vent could comprise other geometries or arrangements, such as slots or a controlled leak between components, for example. The vent could also comprise diffuser materials to reduce noise and/or draft. The bias flow holes 2110 are a collection of orifices that are configured to exhaust air and flush $CO_2$ to reduce the likelihood of rebreathing expired carbon dioxide by the user. While the bias flow holes 2110 are shown exclusively on the connector 2106, in some configurations, the bias flow holes 2110 can be provided on the mask shell 2102, on the mask seal 2104 or on any combination of the connector 2106, the shell 2102 and the seal 2104 or on any other component of the interface assembly or associated breathing circuit. The bias flow holes 2110 can have any suitable cross-section and can be cylindrical, hour-glass shaped, tapered in either direction, fully or partially tapered, fully or partially cylindrical, contoured to vary in cross-section or the like.

The mask shell 2102 provides a support structure of sorts for the mask assembly 2100 in general and for the mask seal 2104 more specifically. The mask shell 2102 can be formed from any suitable material. In some configurations, the mask shell 2102 is formed from a fairly rigid material. In some configurations, the mask shell 2102 is formed from a plastic material, such as a polycarbonate material. In some configurations, the mask assembly 2100 can comprises a mask seal that includes a mask seal clip that is separate from but attachable to a mask shell. In such a configuration, the mask seal clip would connect the mask seal 2104 to the mask shell 2102. In such configurations, the mask seal and mask seal clip can be formed separately and secured together or the mask seal and the mask seal clip can be integrated into a single component. In some configurations, the mask seal can be overmolded onto the mask seal clip and, in some configurations, the mask seal 2104 can be overmolded directly onto the mask shell 2102, which can comprise chemical and/or mechanical overmolding, for example.

In some configurations, the mask shell 2102 comprises a substantial portion of a forward wall of the mask assembly 2100. Such an arrangement provides an advantageous level of support to the mask seal 2104. For example, the mask shell 2102 comprises a substantial portion of an oral portion of the forward wall of the mask assembly 2100. In some configurations, the mask shell 2102 is generally limited to the oral portion of the mask assembly 2100 and does not extend into the nasal portion of the mask assembly 2100, at least to any significant extent. Such an arrangement can provide support to the mask seal 2104, while advantageously permitting movement or deformation of the nasal portion of the mask seal 2104. In the illustrated configuration, the mask shell 2102 sweeps rearward from a central portion 2112 toward opposing side portions 2116. The central portion 2112 contains an aperture 2114 for receiving the connector 2106. The mask shell 2102 can have a generally or substantially constant height throughout the central portion 2112 and opposing side portions 2116. In other arrangements, the mask shell 2102 can vary in height, such as by forming a shape that generally mimics the frontal shape of the mask seal 2104. The height of the mask shell 2102 can be substantially equal to a height of the oral portion of the mask seal 2104. A width of the mask shell 2102 can comprise a significant portion of the overall width of the oral portion of the mask assembly 2100, such as at least about three-quarters of the overall width of the oral portion of the mask assembly 2100. Such an arrangement of the mask shell 2102 can provide reinforcement to the central and lateral portions of the mask seal 2104. In some configurations, the mask shell 2102 could be minimal, such as an annular support ring or frame, for example.

The mask seal 2104 is designed to seal against the face of the user. The mask seal 2104 preferably is formed of a soft material, such as silicone, for example but without limitation. In some configurations, at least portions of the mask seal 2104 can be textured to improve comfort to the user. For example, in some configurations, at least portions of the mold used to form the illustrated mask seal 2104 can be bead blasted to provide a surface texture in at least the regions of the mask seal 2104 that will contact the skin of the user. Other techniques for texturing one or more surface of the mask seal 2104 can be used. In some configurations, it may be desirable to avoid surface texturing and provide at least the face-contacting surfaces of the mask seal 2104 with a smooth surface texture, which may increase grip of the mask seal 2104 on the user's face and improve sealing characteristics.

As described above, the illustrated mask seal 2104 comprises a nasal-oral mask seal and, therefore, comprises at least one oral opening 2122 and at least one nasal opening 2124. In some configurations, the mask seal 2104 can comprise a combined oral-nasal opening. In some configurations, the mask seal 2104 can comprise more than one nasal opening 2124. In some configurations, the mask seal 2104 can comprise nasal openings 2124 defined within superstructures, such as pillows, prongs or the like. In some configurations, the nasal opening 2124 can be defined by a nasal cushion or insert, which can be overmolded or otherwise secured to a base structure of the mask seal 2104. An example of such an arrangement is disclosed in Applicant's publication no. WO 2014/062070, the entirety of which is incorporated by reference herein.

The at least one oral opening 2122 and the at least one nasal opening 2124 preferably communicate with a single chamber 2125 that is defined within the mask assembly 2100. The chamber 2125 of the illustrated mask assembly 2100 is at least partially defined by the mask shell 2102 and the mask seal 2104. The at least one oral opening 2122 is substantially opposed to the aperture 2114 that receives or communicates with the connector 2106. The at least one nasal opening 2124 can be vertically above the at least one oral opening 2122. The at least one nasal opening 2124 can be positioned between the aperture 2114 for the connector 2106 and the at least one oral opening 2122 in a fore-aft direction of the mask assembly 2100. The at least one nasal opening can have an axis that is inclined relative to vertical and that, in some arrangements, can generally extend through the aperture 2114 for the connector 2106.

The mask seal 2104 preferably comprises a pair of paddles 2126 that extend upward above an upper surface 2130 (FIG. 8) of a central portion of the mask seal 2104. The upper surface 2130 can define a line that lies along a central surface of the nasal surface of the mask seal 2104 in a fore-aft direction. Such a line extends generally along the nasal septum in a direction away from the user's face. The paddles 2126 are configured to extend upward alongside, and in some configurations above, the nares. The paddles 2126 can contact the edges of the nares and/or sides of the nose. The paddles 2126 or portions of the mask seal 2104 between the paddles 2126 may or may not cover the tip of the user's nose. As described herein, preferably the mask seal 2104 does not contact the bridge of the user's nose.

In some configurations, the paddles 2126 each comprise an air pocket that is in direct fluid communication with the air path through the mask assembly 2100 from the connector 2106 to the at least one nasal opening 2124 and the at least one oral opening 2122. The paddles 2126 can be configured to expand in volume in response to elevated pressure within the mask seal 2104 and/or flex inwardly to accommodate various facial and nasal geometries and assist in creating a sealed contact with the user's face. Expansion of the paddles 2126 can assist in sealing against the face of the user, especially along the varying contours on and around the user's nose. Inward flexing of the paddles 2126 allows the central portion (e.g., upper surface 2130) to move downward with less restriction or less stretching of the material of the mask seal 2104 so that the mask seal 2104 can better conform to various nasal geometries.

The height of the paddles 2126 above the upper surface 2130 can be selected to provide a desired balance between stability of the mask seal 2104 on the user's face (e.g., vertical stability) and being able to accommodate a range of nasal geometries or reducing visual disruption by the paddles 2126. In general, higher paddles 2126 tend to provide additional vertical stability of the mask assembly 2100, while lower paddles 2126 tend to provide a better fit of a wider range of users and result in less visual disruption. In some configurations, the paddle height 2126 is between about 10 mm and about 30 mm or between about 15 mm and about 25 mm. In some configurations, the paddle height 2126 is between about 15 mm and about 22 mm or between about 18 mm and about 20 mm, including an value or sub-range within the above-described ranges. In some configurations, the paddle height is about 18.5 mm.

The illustrated mask seal 2104 of the mask assembly 2100 comprises a fairly complex range and configuration of thicknesses, as shown in FIGS. 7-21. The thicknesses are varied to take advantage of or provide different characteristics in different regions of the illustrated mask seal 2104. For example, the thicknesses in the various regions can be selected to address a desired characteristic for that region and/or the mask seal 2104 as a whole. Such characteristics can include, for example, allowing the mask seal 2104 to conform to the facial geometry of the user to enhance sealing properties or comfort, supporting the shape of the mask seal without significant internal gas pressure to facilitate fitment and/or in response to internal gas pressure and/or external pressure (e.g., caused by headgear forces) or providing strength or durability.

FIGS. 7-10 illustrate views of the mask seal 2104 with regions of different thickness outlined. In general, the outer surface of the mask seal 2104 defines a relatively smoothly shaped or curved surface without abrupt changes in direction. The different thicknesses are created by changes in wall thickness that are apparent on or created by changes in shape of an interior surface of the mask seal 2104, as illustrated by the sectional views of FIGS. 12-21. FIGS. 7-10 illustrate differences in thicknesses of the mask seal 2104, such as those in the above-described regions or portions. In some configurations, support structures 2163 for the paddles are thicker than a nasal region 2168 and an upper front portion 2150. In some configurations, a relatively abrupt transition in thickness occurs between the nasal region 2168 and upper front portion 2150 and the supports 2163. In contrast, transitions in thickness between outer peripheral portions 2162, the supports 2163 and an upper rear portion 2156 are more gradual. In addition, in at least some configurations, transitions in thickness between the outer peripheral portions 2162, the upper rear portion 2156 and the oral region 2166 are relatively gradual. The various portions of the mask seal 2104 are described further below.

To reduce the incidence of wrinkling of at least some of the face contacting regions of the mask seal 2104 during use, it has been found that the outer peripheral portions 2162 of the mask seal 2104, which are generally adjacent to some or all of the face contacting portions of the mask seal 2104, provide desirable performance when the outer peripheral portions 2162 are fairly rigid or relatively rigid compared to adjacent portions or other portions of the mask seal 2104. In the illustrated arrangement, the outer peripheral portions 2162 extend along the generally vertically extending portions on the rear of the mask seal 2104 and wrap slightly inward at a bottom of the rear of the mask seal 2104. In addition, the outer peripheral portions 2162 wrap from a rear facing side of the mask seal around to at least a portion of a laterally facing side of the mask seal 2104.

In the illustrated arrangement, the outer peripheral portions 2162 are located on each lateral side of the oral opening 2122. In some configurations, the outer peripheral portions 2162 extend along an entire height of the oral opening 2122. Upper ends of the outer peripheral portions 2162 can extend at least to about an upper end of the oral opening 2122. Lower ends of the outer peripheral portions 2162 can extend below a lower end of the oral opening 2122. As described above, in some configurations the outer peripheral portions 2162 wrap inwardly below the oral opening 2122 such that portions of the outer peripheral portions 2162 are positioned vertically below portions of the oral opening 2122.

The relatively increased thickness of the outer peripheral portions 2162 can assist in resisting or preventing collapse of the mask seal 2104 in the absence of significant internal gas pressure to facilitate fitment and provide feedback to the user, such as in response to applied forces (e.g., headgear forces). The outer peripheral portions 2162 can help maintain the curved shape of the lateral sides of the mask seal 2104 and/or help maintain a separation between a rear wall of the mask seal 2104 (defining a face contacting surface) and a front wall of the mask seal 2104 at least in response to forces experience during normal use. In some configurations, the thickness of a portion or an entirety of the outer peripheral portions can be between about 1.0 mm and about 2.0 mm. In the illustrated configuration, a portion or an entirety of the outer peripheral portions 2162 preferably have a thickness of about 1.5 mm. The thicknesses of the outer peripheral portions 2162 can be consistent or varied within a boundary of the outer peripheral portion 2162.

The illustrated mask seal 2104 also comprises the oral region 2166. The oral region 2166 in the illustrated mask seal 2104 extends along at least a portion of the oral opening 2122. Preferably, the oral region 2166 extends along at least a lower portion of the oral opening 2122. The oral region 2166 can extend along at least the sides and the bottom of the oral opening 2122. In the illustrated arrangement, the oral region 2166 circumscribes the oral opening 2122. The oral region 2166 can comprise a relatively thin band that surrounds some or all of the oral opening 2122, such as the sides and upper portion in the illustrated arrangement. The illustrated oral region 2166 comprises a lower thickened band portion that extends downwardly away from the oral opening 2122 and can extend toward or to a lower edge of the mask seal 2104. The lower thickened portion of the oral region 2166 can contact the area below the lower lip of the user and can allow the mask seal 2104 to accommodate a range of chin geometries. The lower thickened portion of the oral region 2166 can define a curved edge opposite the edge adjacent the oral opening 2122.

The oral region 2166 provides a softer region that contacts the face. Accordingly, the oral region 2166 can have a thinner cross-section than the outer peripheral portions 2162 and/or other regions of the mask seal 2104. In some configurations, the oral region 2166 has the smallest thickness or is among the smallest thicknesses of the mask seal 2104. For example, a portion or an entirety of the oral region 2166 can have a thickness of between about 0.2 mm and about 0.5 mm. In the illustrated configuration, the thickness of a portion or an entirety the oral region 2166 is about 0.3 mm. The thickness of the oral region 2166 can be consistent or variable within the oral region 2166.

The mask seal 2104 can also include the nasal region 2168 located near the nasal opening 2124. The nasal region 2168 can surround a portion or an entirety of the nasal opening 2124. In the illustrated arrangement, the nasal region 2168 surrounds an entirety of the nasal opening 2124 and has side portions that are located at least partially on the paddles 2126. The nasal region 2168 can wrap from the rear of the mask seal 2104 toward the front. In the illustrated arrangement, the nasal region 2168 is radially spaced from the nasal opening 2124. Given a desire to gently seal against the lower portion of the nose, the nasal region 2168 in the illustrated configuration has a fairly small thickness. In some configurations, the nasal region 2168 has the smallest thickness of the mask seal 2104 or is equal to or among the smallest thickness of the mask seal 2104. For example, a portion or an entirety the nasal region 2168 can have a thickness that is equal to or slightly larger than the thickness of the oral region 2166. In some configurations, the thickness of a portion or an entirety the nasal region 2168 is between about 0.3 mm and about 0.5 mm or 0.6 mm. In some configurations, the thickness of a portion or an entirety the nasal region 2168 is about 0.3 mm. The thickness of the nasal region 2168 can be consistent or variable within the nasal region 2168. A portion or an entirety of the nasal region 2168 could have a thickness that is less than about 0.3 mm. For example, the thickness could be as low as about 0.15 mm. However, it has been determined that lower thicknesses can result in or increase the likelihood of creasing of the nasal region 2168 for some facial geometries and/or under some operational gas pressures. Keeping the thickness above about 0.3 mm in a substantial portion or an entirety of the nasal region 2168 can reduce the incidence of creasing over a substantial range of operational pressures, which may comprise an entire range of normal operating pressures.

The mask seal 2104 can also include the upper front portion 2150 that is positioned above the mask shell 2102. In the illustrated arrangement, the upper front portion 2150 extends in a lateral direction across the front of the mask seal 2104 between the mask shell 2102 and the nasal region 2168 in a vertical direction. The upper front portion 2150 can extend any suitable distance across the mask seal 2104, such as along a substantial entirety of a width of the mask seal 2104 or the width of the mask seal 2104 at least at the location of the upper front portion 2150. An upper edge of the upper front portion 2150 can be curved and the sides of the upper front portion 2150 can have a greater height than a central portion of the upper front portion 2150 such that the central portion defines a valley of the upper front portion 2150. In some configurations, the sides of the upper front portion 2150 can extend into the portion of the mask seal 2104 defining the paddles 2126. In some configurations, a lower edge of the upper front portion 2150 can be generally linear and extend in a horizontal or lateral direction. The lower edge of the upper front portion 2150 can have generally the same shape as an upper edge of the mask shell 2102.

The upper front portion 2150 preferably has a fairly small thickness to promote flexibility of the upper front portion 2150. That is, preferably, the upper front portion 2150 is able to flex, fold or otherwise deform in response to pressure acting on other portions of the mask seal 2104, such as downward pressure on the nasal region 2168, for example. Such an arrangement can assist the mask seal 2104 in conforming to different facial geometries of possible users. In addition, such an arrangement can facilitate expansion or ballooning of the paddles 2126, at least in the absence of external restraints on such expansion. In some configurations, the upper front portion 2150 has the smallest thickness of the mask seal 2104 or is equal to or among the smallest thickness of the mask seal 2104. For example, a portion or an entirety the upper front portion 2150 can have a thickness that is equal to the thickness of one or both of the oral region 2166 and the nasal region 2168. In some configurations, the thickness of a portion or an entirety the upper front portion 2150 is between about 0.2 mm and about 0.5 mm. In some configurations, the thickness of a portion or an entirety the upper front portion 2150 is about 0.3 mm. The thickness of the upper front portion 2150 can be constant or variable within the upper front portion 2150. The thickness of the upper front portion 2150 could be smaller or larger depending on the desired properties of the mask seal 2104, such as compliance of the nasal region 2168.

The mask seal 2104 can also comprise the support structures or supports 2163 for the paddles 2126, which can be in the form of suspension members or springs that provide mechanical rigidity and structure to hold the shape of the paddles 2126 when the mask seal 2104 is worn by a user. The supports 2163 can comprise thickened regions of the seal material. The supports 2163 preferably are sized, shaped and/or otherwise configured to transfer force from a rearward or user-contacting surface of the paddles 2126 toward or to a forward surface of the paddles 2126. In some configurations, the interface can include a support portion or cover for the paddles 2126 and the supports 2163 can transfer force from the rearward surface of the paddles 2126 to the forward surface or other portion of the paddles 2126 or mask seal 2104 that contacts or faces the support portion or cover. In some configurations, the supports 2163 can transfer force from the rearward surface of the paddles 2126 toward or to another support portion of the mask seal 2104 (e.g., the mask shell 2102) or interface. The supports 2163 can resist or prevent collapse of the paddles 2126 or other related or adjacent portions of the mask seal 2104 to facilitate fitment and provide feedback to the user, such as in response to applied forces (e.g., headgear forces). In some configurations, the supports 2163 can resist or prevent collapse of the paddles 2126 or other related or adjacent portions of the mask seal 2104 in the absence of significant internal gas pressure. The supports 2163 can help maintain the shape of the paddles 2126 of the mask seal 2104 and/or help maintain a separation between a rear wall of the mask seal 2104 (defining a face contacting surface) and a front wall of the mask seal 2104 at least in response to forces experience during normal use. In addition, the supports 2163 can provide support to the nasal region or nasal seal portion 2168. In particular, the supports 2163 can provide structure to and inhibit or prevent creasing, wrinkling or collapsing of the nasal seal portion 2168 and/or the upper front portion 2150. As described above, the nasal seal portion 2168 and/or the upper front portion 2150 preferably are relatively thin to permit these portions of the mask seal 2104 to conform to the user's nose. The relatively thin nasal seal portion 2168 and/or the upper front portion 2150 can expand and seal around the user's nose. The supports 2163 provide rigid portions or elements of the seal 2104 adjacent or near the relatively thin nasal seal portion 2168 and/or the upper front portion 2150 to inhibit or prevent collapse when a user engages his or her nose into the mask assembly 2100. The upper rear portion 2156 can assist in preventing collapse of the nasal seal portion 2168 and/or the upper front portion 2150.

In some configurations, the supports 2163 help to reduce the likelihood of wrinkling or creasing of the face contacting portions of the paddles 2126 during use while allowing the laterally inner portions to be as thin as desired within practical limitations, such as those described above. The supports 2163 can assist in inhibiting or preventing collapse of the paddles 2126 or maintaining a desired shape of the paddles 2126. For example, the supports 2163 can assist in maintaining a desired fore-aft shape of the paddles 2126 and/or a lateral or side-to-side shape of the paddles 2126. The level of support provided can vary in different directions. In some configurations, the supports 2163 could be formed as separate portions or separate components from the seal material and could be the same or a different material. Such separate supports 2163 could be coupled to the paddles 2126 or other portion of the mask seal 2104 if desired. The supports 2163 disclosed herein can be particularly useful in under-nose type mask assemblies, including both nasal masks and combined nasal-oral masks. However, the supports 2163 can also be utilized in other types of mask assemblies or interfaces, including those that cover, contact or seal against the bridge of the user's nose and/or include a T piece or other type of forehead support, for example and without limitation. The supports 2163 can be utilized, or modified for use, in any locations of an interface in which support against collapsing and/or support against overexpansion may be desirable. Such locations can be at or near the portion of the seal that contacts or extends alongside the user's nose or can be at other locations.

In the illustrated arrangement, at least a portion of the supports 2163 extend generally in a fore-aft direction along the paddles 2126. In particular, the supports 2163 can extend along the upper edge of the paddles 2126 or the region or ridge that joins the laterally outer surface portion and the laterally inner surface portion along the upper edges of the paddles 2126. The supports 2163 can extend along a portion of the sides of the nasal region 2168. The supports 2163 can comprise a generally thin, elongate shape. Viewed from above, the supports 2163 can comprise a generally triangular shape with a base of the triangle positioned rearwardly of the top or point of the triangle. Other shapes are possible to achieve a desired level of support or for other design considerations, such as the desired shape(s) of adjacent or nearby structures. The supports 2163 can have additional portions to provide other levels of support or to provide support in other directions. For example, the supports 2163 could connect to one another, such as along one or both of the forward or rearward sides of the nasal opening 2124. In some configurations, the supports 2163 could extend completely through the paddles 2126, such as to the mask shell 2102, for example.

The supports 2163 can have a different thickness than other portions of the paddles 2126 and can have a greater thickness than other portions of the paddles 2126. In some configurations, the supports 2163 can have the largest thickness or among the largest thicknesses of the mask seal 2104. In some configurations, a portion or an entirety of the supports 2163 can have a thickness of between about 1.5 mm and about 3.5 mm. In the illustrated configuration, a portion or an entirety of the supports 2163 can have a thickness of about 2.5 mm. The thickness of the supports 2163 can be constant or variable.

Figure 19:
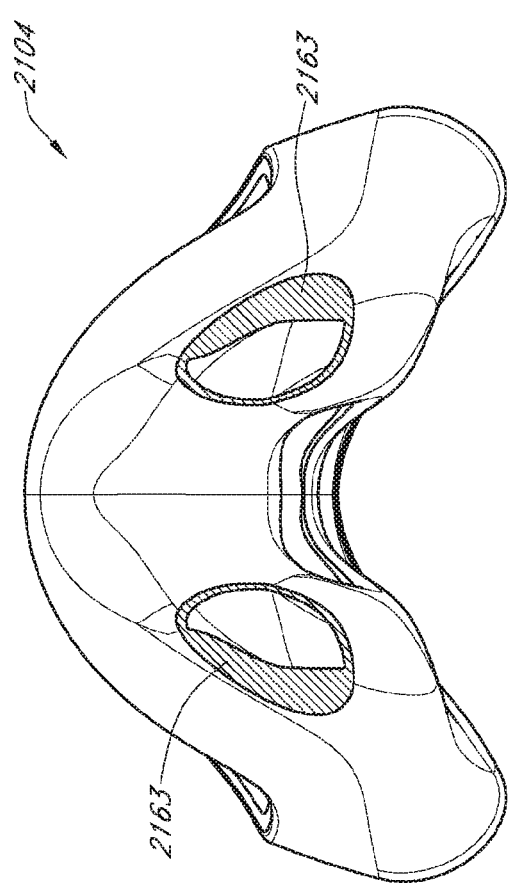
FIG. 19 is a sectional view of the mask seal taken along line 19-19 of FIG. 11.
Figure 20:
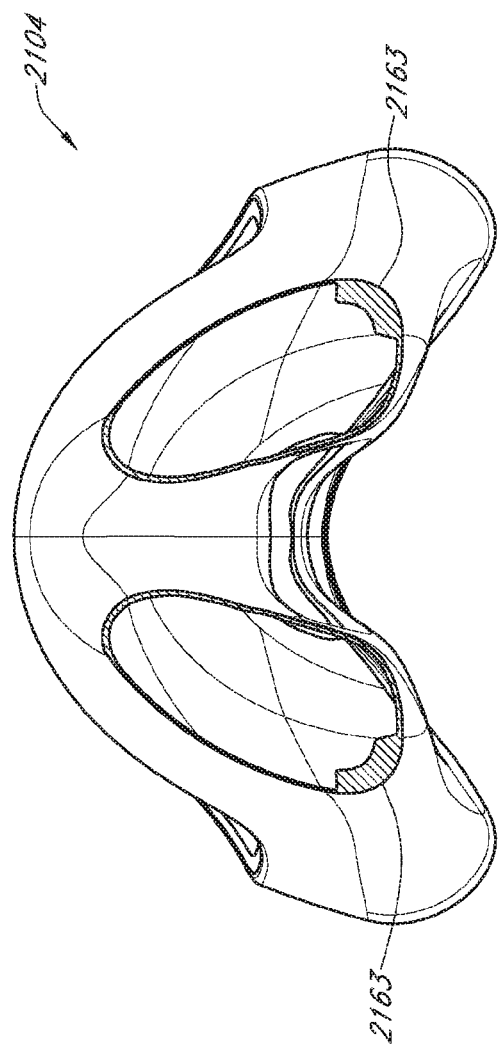
FIG. 20 is a sectional view of the mask seal taken along line 20-20 of FIG. 11.
Figure 21:
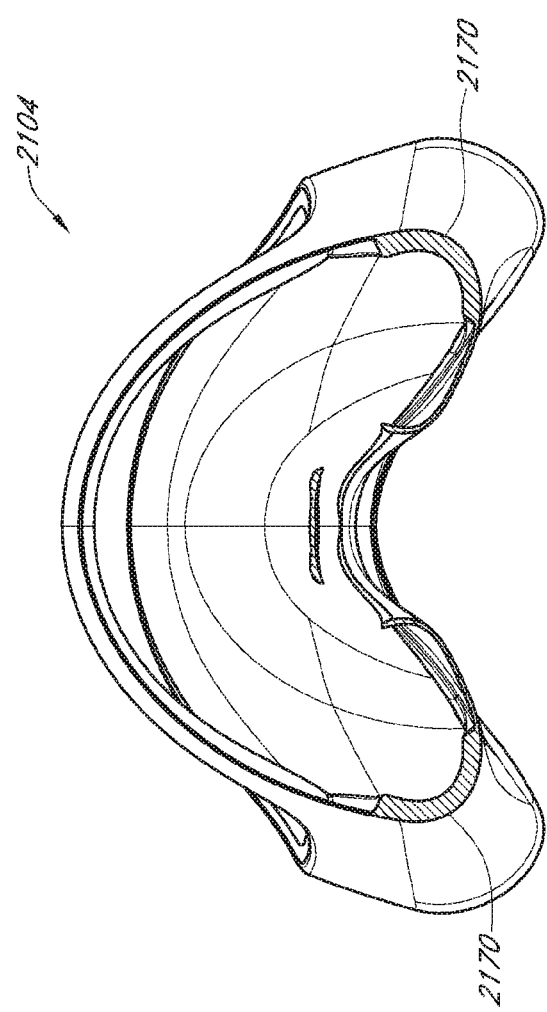
FIG. 21 is a sectional view of the mask seal taken along line 21-21 of FIG. 11.

With reference to FIGS. 19-21, portions of the mask seal 2104 incorporating the paddles 2126 are shown in cross section. As illustrated therein, and described above, the paddles 2126 can have a relatively thin cross section, at least in those sections other than the supports 2163. In some configurations, the paddles 2126 can be formed at least in part with a cross section sufficiently thin to allow controlled inflation or controlled expansion at typical treatment pressures (e.g., about 3 to about 25 cmH2O). In some configurations, such a thickness might be equal to or lower than about 0.5 or 0.6 mm, equal to or lower than 0.3 mm or equal to or lower than about 0.2 mm depending upon the particular location within the paddle 2126 and/or the material used. In some configurations, the portion of the paddles 2126 that will contact the face comprises a generally constant cross-sectional thickness. As illustrated in FIGS. 16-21, the thickened portions can continue to extend below the supports 2163 of the paddles 2126, such as into a region of the mask seal 2104 below the paddles 2126.

In some configurations, the mask seal 2104 comprises an upper rear portion 2156 that extends in a lateral direction along a rear surface of the mask seal 2104 between the nasal region 2168 and the oral region 2166. In the illustrated arrangement, the upper rear portion 2156 is an elongated strip region of the mask seal 2104 defined by an internal rib. In some configurations, the ends of the upper rear portion 2156 can have a greater height or vertical dimension than a center portion of the upper rear portion 2156. In some configurations, the upper and lower edges of the upper rear portion 2156 can generally follow the curvature or shape of the corresponding portions of the nasal region 2168 and oral region 2166, respectively. The upper rear portion 2156 can extend along a substantial width of the mask seal 2104. For example, the upper rear portion 2156 can have a length that is at least one-half of a width of the mask seal 2104 at the location of the upper rear portion 2156 and/or a length that is longer than a width of the nasal opening 2124. In some configurations, the upper rear portion 2156 can have a length that is greater than a width of the oral opening 2122. The upper rear portion 2156 can be centered in a lateral direction of the mask seal 2104. In some configurations, the upper rear portion 2156 extends into or is connected with the outer peripheral portions 2162. Such an arrangement assists in maintaining the open shape of the rear surface of the mask seal 2104 to facilitate fitment to the user's face.

The upper rear portion 2156 can provide support to the mask seal 2104 between the nasal region 2168 and the oral region 2166, such as to limit, inhibit or prevent collapse of the mask seal 2104 in a lateral direction between the outer peripheral portions 2162 and/or in a vertical direction between the nasal region 2168 and the oral region 2166 or to maintain a desired separation of those portions 2162 or regions 2168, 2166. The upper rear portion 2156 can have a thickness that is sufficient to provide such support and that can be greater than one or both of the nasal region 2168 and the oral region 2166. The upper rear portion 2156 can have a thickness that is smaller than one or both of the outer peripheral portions 2162 and the supports 2163. In some configurations, the upper rear portion 2156 has a thickness that is greater than both the nasal region 2168 and the oral region 2166 and smaller than both the outer peripheral portions 2162 and the supports 2163. In some configurations, a portion or an entirety of the upper rear portion 2156 can have a thickness that is between about 0.5 mm and about 1.5 mm. In the illustrated configuration, a portion or an entirety the upper rear portion 2156 has a thickness of about 1.0 mm. The thickness could be smaller or larger depending on the desired characteristics of the support provided by the upper rear portion 2156.

Figure 5:
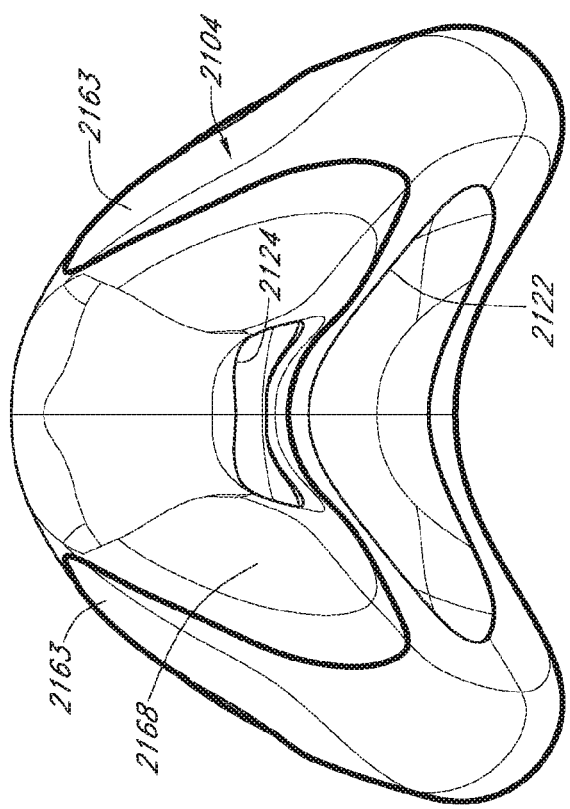
FIG. 5 is a rear view of the mask assembly of FIG. 4 illustrating a thickened region of a mask seal of the mask assembly.
Figure 6:
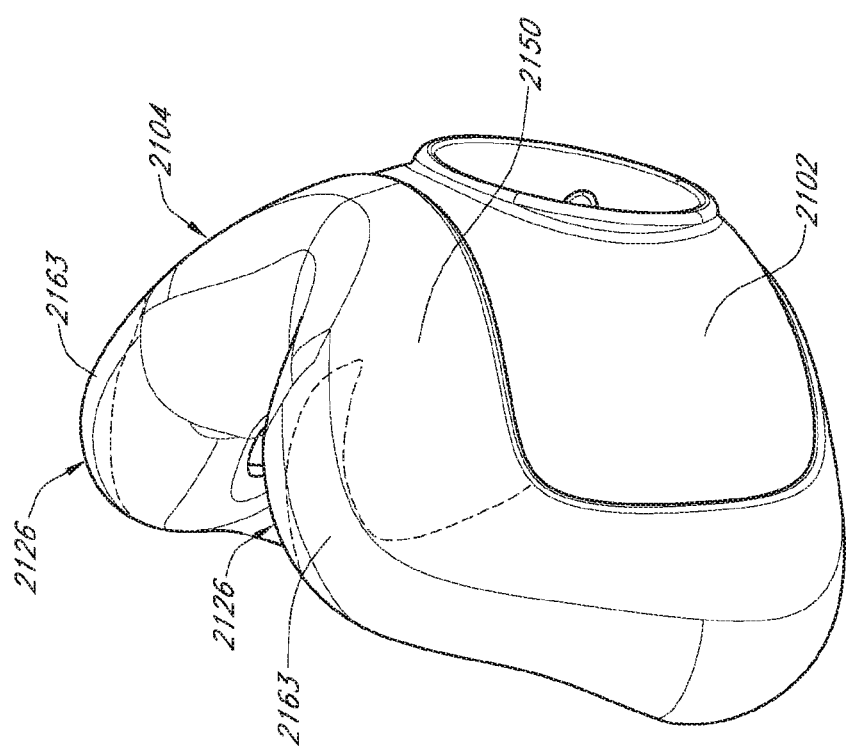
FIG. 6 is a side view of the mask assembly of FIG. 4 illustrating the thickened region of the mask seal.
Figure 7:
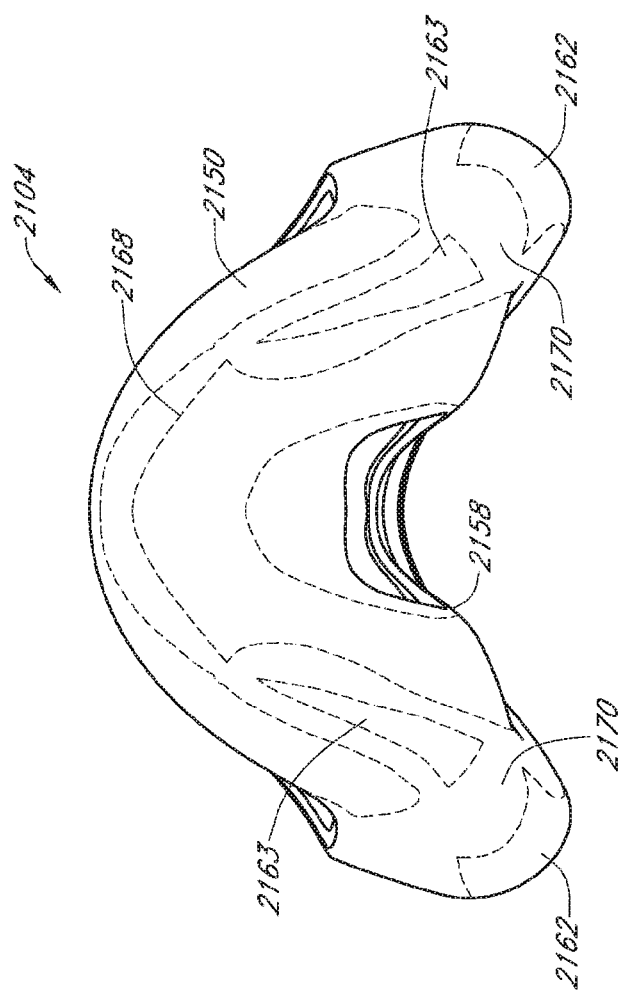
FIG. 7 is a top view of the mask seal of the mask assembly of FIG. 4 illustrating regions of different thickness of the mask seal.
Figure 8:
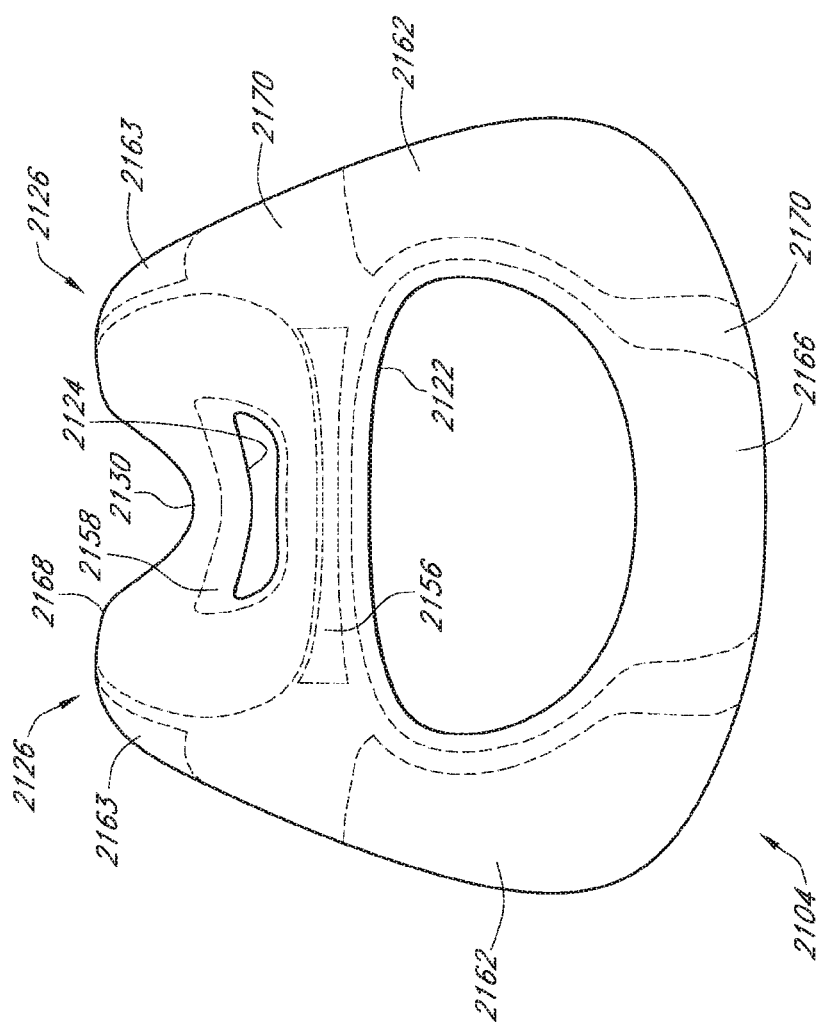
FIG. 8 is a rear view of the mask seal of FIG. 7 illustrating regions of different thickness of the mask seal.
Figure 9:
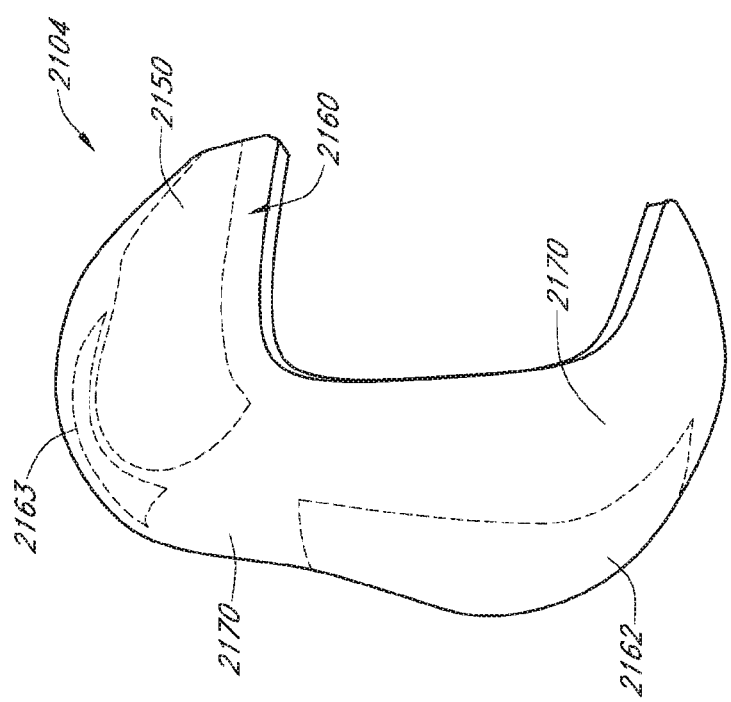
FIG. 9 is a side view of the mask seal of FIG. 7 illustrating regions of different thickness of the mask seal.
Figure 10:
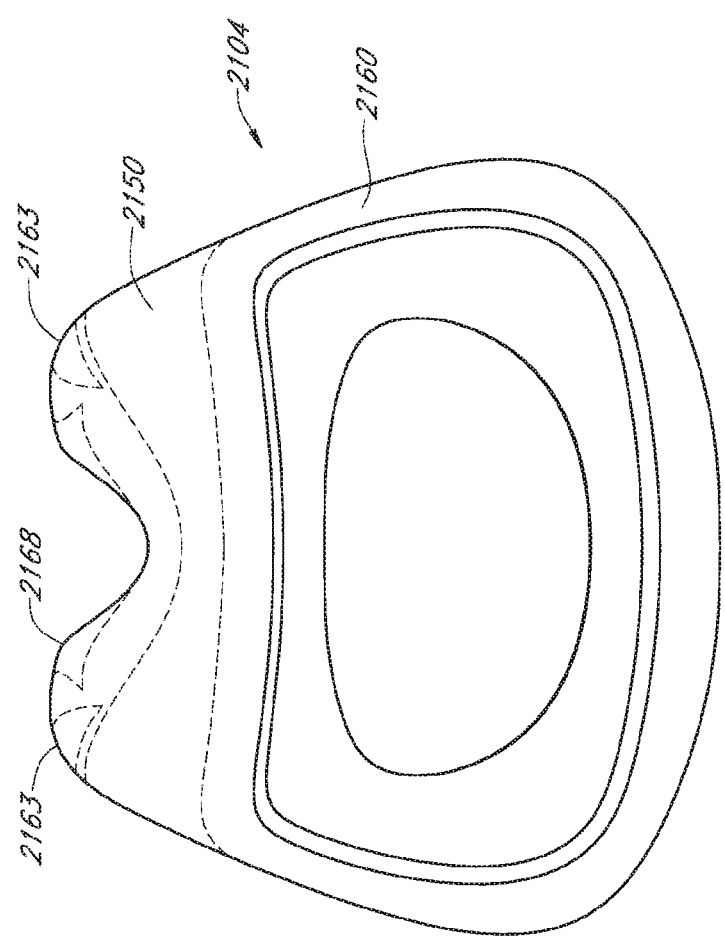
FIG. 10 is a front view of the mask seal of FIG. 7 illustrating regions of different thickness of the mask seal.
Figure 11:
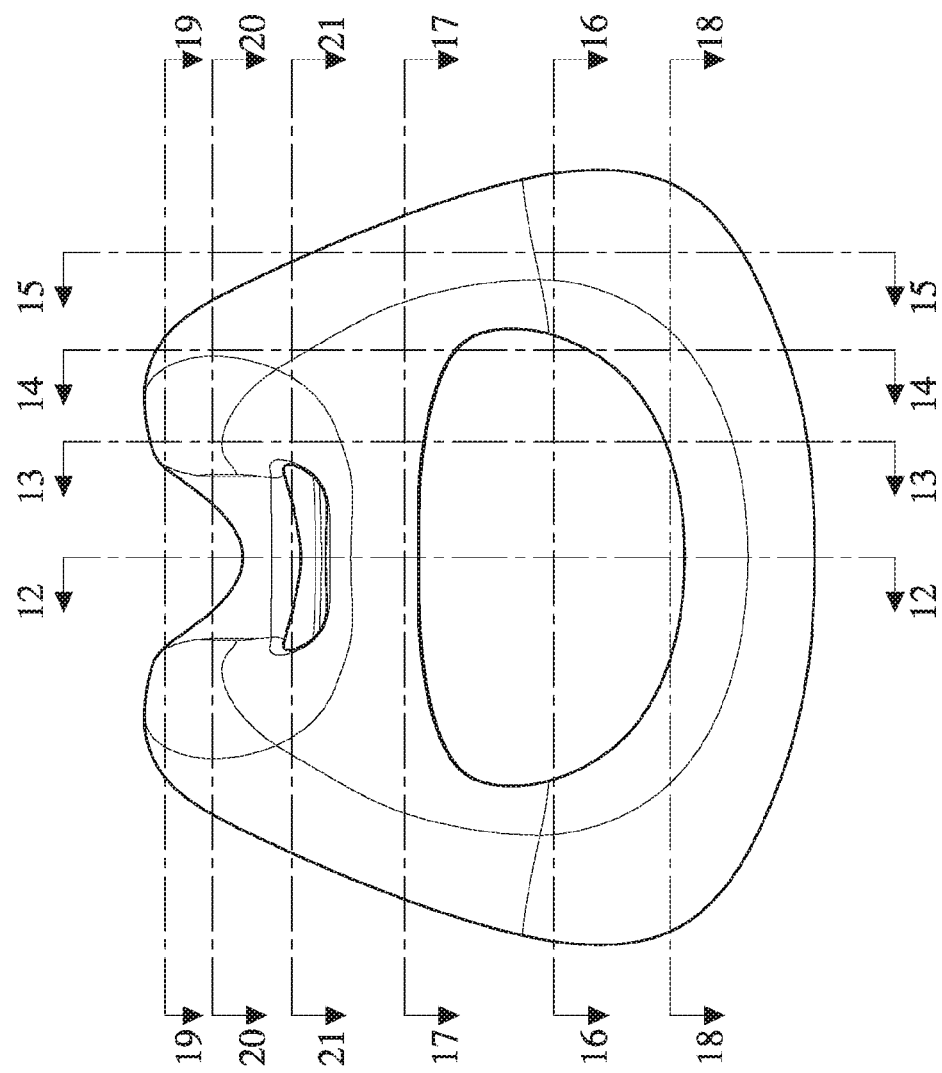
FIG. 11 is a rear view of the mask seal of FIG. 7.
Figure 12:
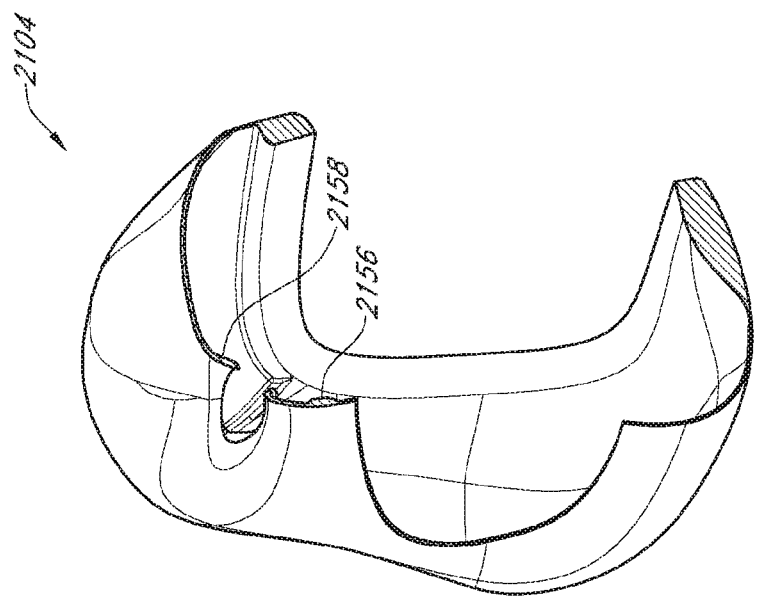
FIG. 12 is a sectional view of the mask seal taken along line 12-12 of FIG. 11.
Figure 13:
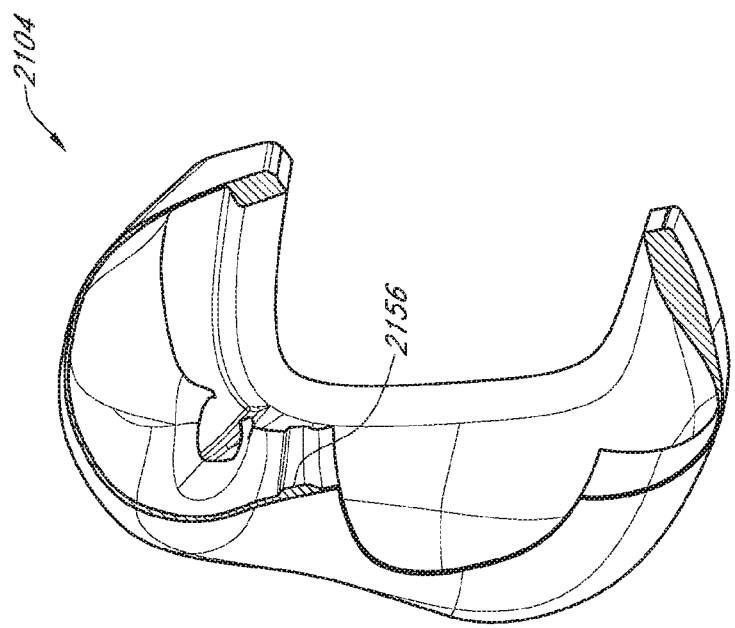
FIG. 13 is a sectional view of the mask seal taken along line 13-13 of FIG. 11.
Figure 14:
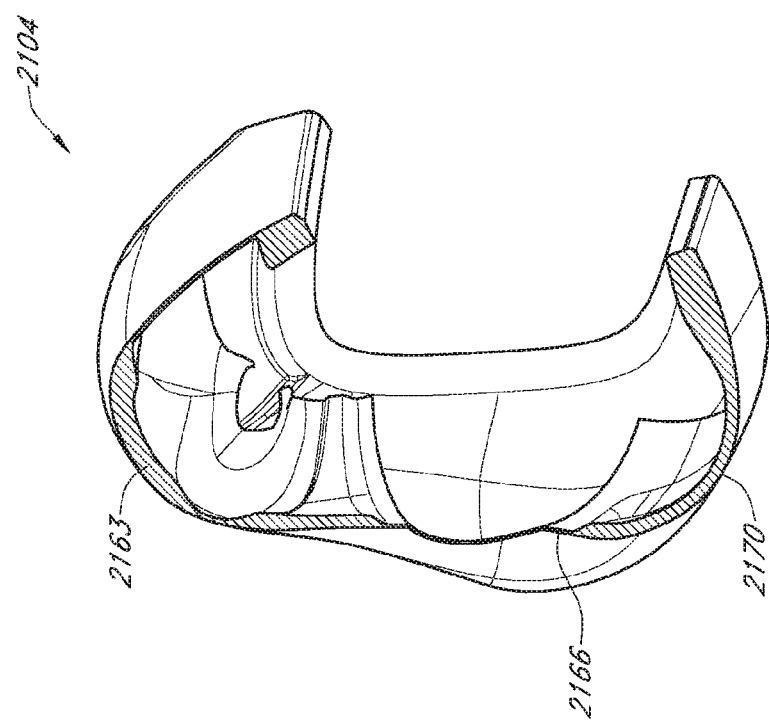
FIG. 14 is a sectional view of the mask seal taken along line 14-14 of FIG. 11.
Figure 15:
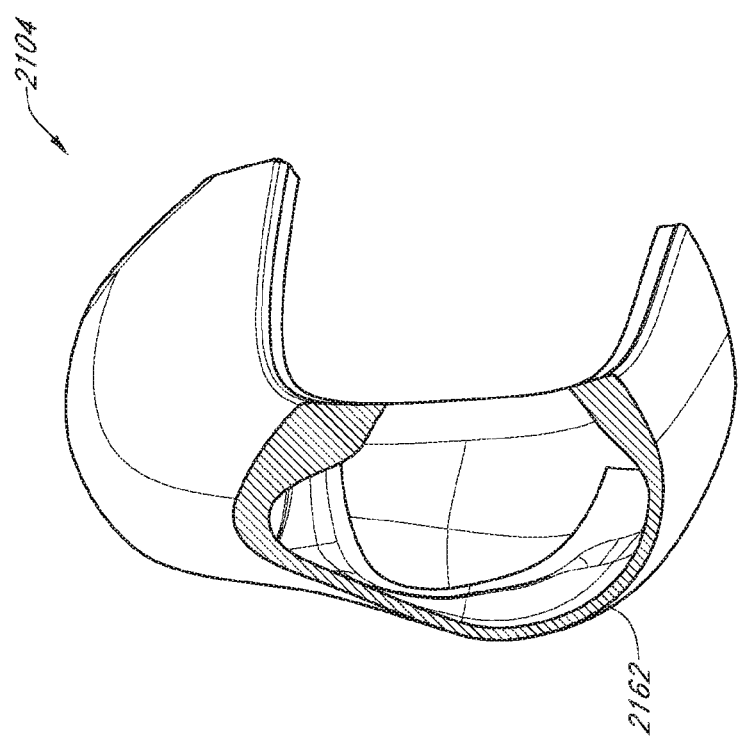
FIG. 15 is a sectional view of the mask seal taken along line 15-15 of FIG. 11.
Figure 16:
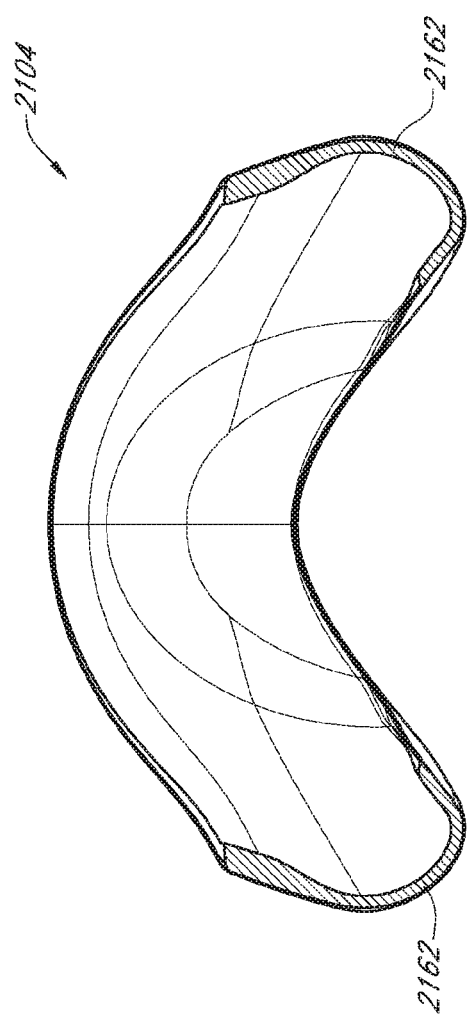
FIG. 16 is a sectional view of the mask seal taken along line 16-16 of FIG. 11.
Figure 17:
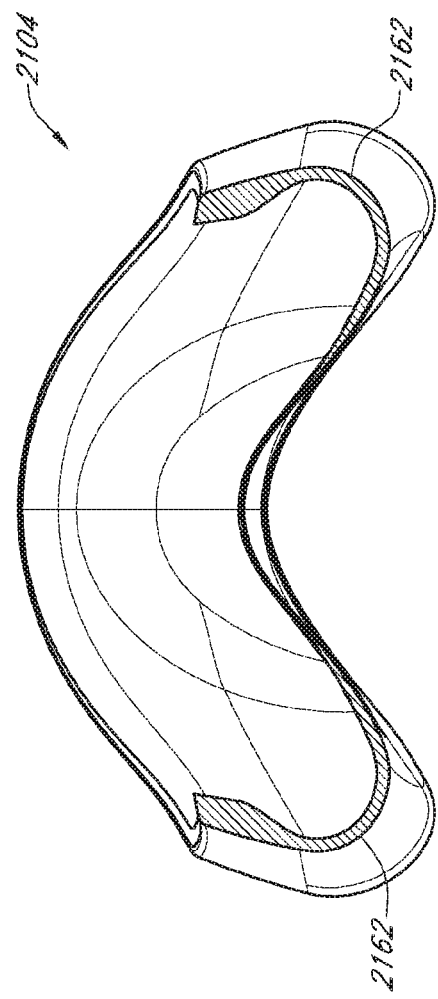
FIG. 17 is a sectional view of the mask seal taken along line 17-17 of FIG. 11.
Figure 18:
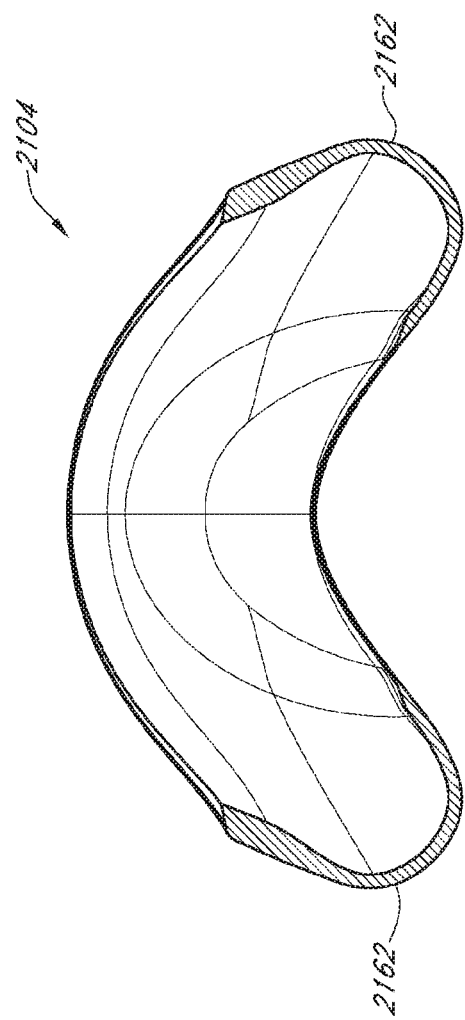
FIG. 18 is a sectional view of the mask seal taken along line 18-18 of FIG. 11.

The mask seal 2104 can have other portions outside of those described above. For example, the mask seal 2104 can have one or more transition portions 2170 in the area(s) between the above-described portions. The transition portion 2170 can be referred to in the singular herein; however, the transition portion 2170 is not necessarily a single contiguous region, but may comprise several discrete or non-contiguous regions. The transition portion 2170 can define a transitioning thickness between any one or more (including all) of the upper front portion 2150, the upper rear portion 2156, the supports 2163, the outer peripheral portions 2162, the oral region 2166 and the nasal region 2168. The transition portion 2170 can define a thickness that extends away from or is positioned or transitions between two regions in any suitable manner, such as a gradual or abrupt transition, for example. A transition in thickness can occur within the transition portion 2170 or along an edge of the transition portion 2170, for example. In the illustrated configuration, the outer peripheral portions 2162 are generally surrounded by the transitional portion 2170. The outer peripheral portions 2162 can make a relatively smooth transition into the supports 2163 such that the outer peripheral portions 2162, transition portion 2170 and supports 2163 comprise a generally continuous thickened region, as illustrated in FIG. 5. The oral region 2166 can be separated from the outer peripheral portions 2162 and/or the upper rear portion 2156 by a transition portion 2170. Other configurations also are possible.

The illustrated mask seal 2104 includes a connecting region 2160 that generally encircles an opening that receives the mask shell 2102 and can be configured to join the mask seal 2104 to the mask shell 2102. In the illustrated arrangement, the connecting region 2160 is illustrated as forming a portion of or being contained with the transition portion 2170. In some configurations, the connecting region 2160 could have a specific construction providing desirable characteristics, such as permitting connection to the mask shell 2102 and/or providing durability. In some configurations, the connecting region 2160 can be the thickest portion of the seal member 2104. In some configurations, the thickness of the connecting region can be between about 2 mm and about 5 mm or between about 3 mm and about 3.5 mm. In other configurations, the thickness could be smaller or larger depending on the desired properties, such as type of connection with the mask shell 2102 (e.g., overmolded connection). The thickness can vary within the connecting region 2160, such as in the case of the mask seal 2104 mechanically-engaging the mask shell 2102. For example, the periphery of the mask shell 2102 can include recesses or openings that are engaged or passed through by material of the mask seal 2104.

The illustrated mask seal 2104 also includes a nasal opening support 2158 that surrounds a portion or an entirety of the nasal opening 2124. The nasal opening support 2158 can assist in maintaining a desired shape of the nasal opening 2124 and/or limit, inhibit or prevent collapse of the nasal opening 2124. In the illustrated arrangement, the nasal opening support 2158 is illustrated as forming a portion of the transition portion 2170. The nasal opening support 2158 can have a variable or a relatively constant thickness. The nasal opening support 2158 can have a thickness that is larger than the thickness of the nasal region 2168. In some configurations, the nasal opening support 2158 can have a thickness of between about 1.0 mm to about 2.5 mm, for example and without limitation. As described above, the nasal opening support 2158 can be an insert or cushion that is coupled to the material of other portions of the mask seal 2104, such as a substantial entirety of the mask seal 2104.

With additional reference to FIGS. 1-3 and 22-24, as described above, the mask seal 2104 and mask shell 2102 (mask assembly 2100) can form a portion of an interface assembly, which can include the frame 2178 and the headgear 2180. The frame 2178 can be removably connected to the mask assembly 2100 by any suitable arrangement. For example, the frame 2178 can be coupled at or around the aperture 2114 of the mask shell 2102, such as by a snap fit, friction fit or clip connection, among other possibilities. The mask assembly 2100 can be keyed to the frame 2178 to permit assembly in only the correct orientation. The conduit connector 2106 can also be attached to the mask shell 2102, frame 2178 or otherwise supported relative to and adapted to communicate with an interior space of the mask assembly 2100.

In the illustrated arrangement, the frame 2178 comprises one or more portions that are positioned adjacent or contact a portion of the paddles 2126. In some configurations, the frame 2178 comprises a pair of support portions or covers 2182, each of which is associated with one of the paddles 2126 of the mask seal 2104. References to covers 2182 herein can refer to other suitable support structures for the paddles 2126 unless indicated otherwise. The covers 2182 can provide a desirable level of support to the paddles 2126, such as to inhibit or prevent over-expansion and/or outward bulging of the paddles 2126, which can occur in response to gas pressure within the mask seal 2104, for example. As described above, portions of the mask seal 2104 can be textured for purposes of user comfort. Texturing of a surface of the paddles 2126 that contacts or faces the paddle covers 2182 can allow or facilitate relative movement (e.g., sliding movement) of the paddles 2126 and the paddle covers 2182. However, if it is desired for the paddle covers 2182 to grip the paddles 2126 to inhibit movement therebetween, the surface of the paddles 2126 facing or contacting the paddle covers 2182 can be non-textured or have a smooth surface finish. Any suitable method for texturing the mask seal 2104 can be utilized, such as bead blasting of the mold for the mask seal 2104.

Although the illustrated covers 2182 are integrated with the frame 2178, in other configurations, the covers 2182 could be otherwise supported in a desired position relative to the paddles 2126 by any component of the interface assembly. For example, the covers 2182 could be a separate component(s) coupled to the frame 2178 or other portion of the interface assembly, including the mask shell 2102. Such separate covers 2182 can be glued, clipped, welded or otherwise attached to an underlying support structure. In some configurations, the covers 2182 could be integrated with the mask shell 2102. In some configurations, the covers 2182 could be a portion of the mask seal 2104, such as portion having greater thickness or stiffness relative to the paddles 2126. In the illustrated arrangement, the covers 2182 are unitarily formed with the frame 2178. Similarly, the covers 2182 could be unitarily formed with the mask shell 2102, mask seal 2104 or other portion of the interface assembly.

In some configurations, the covers 2182 are positioned next to or against a laterally outer surface of the paddles 2126, with or without a gap, or a varying gap, therebetween, prior to the paddles 2126 being pressurized. With such an arrangement, the covers 2182 can contact the paddles 2126 to limit, inhibit or prevent an undesirable amount of expansion or outward movement of the paddles 2126, such as due to gas pressure within the mask seal 2104. While some expansion of the paddles 2126 may be desirable to, for instance, control creasing of the paddles 2126 or upper portion of the mask seal 2104 (e.g., the nasal region 2168), too much expansion may be uncomfortable to the user, such as by causing the nasal region to press against the underside of the user's nose, and/or compromise the seal between the face of the user and the paddles 2126 or other portions of the mask seal 2104. Thus, characteristics (e.g., size, shape or location) of the covers 2182 can be selected to provide a desired level of support and/or allow a desired level of expansion of the paddles 2126 or other portions of the mask seal 2104. Preferably, the paddles 2126 or at least upper portions of the paddles 2126 are not coupled to the covers 2182 such that the paddles 2126 can flex or pivot inwardly away from the covers 2182. In some configurations, laterally outer surfaces of the paddles 2126 can move inwardly away from the covers 2182. Such an arrangement can advantageously assist in maintaining contact between the laterally inner surfaces of the paddles 2126 and the user's face when downward pressure is applied to the nasal region 2168.

In some configurations, the covers 2182 cover only a portion of the laterally-outward or forward-facing surfaces of the paddles 2126. With such an arrangement, the covers 2182 can provide a desired balance between user comfort and providing support to the paddles 2126. For example, the covers 2182 can cover only a portion of the paddles 2126 in a fore-aft direction. In the illustrated arrangement, the covers 2182 support a forward portion of the paddles 2126 and leave at least a rearward portion of the paddles 2126 exposed. In the illustrated arrangement, the covers 2182 cover substantially an entire height of the paddles 2126. In some configurations, the covers 2182 could cover a substantial entirety or an entirety of the length of the paddles 2126, while leaving some of the height of the paddles 2126 exposed. In some configurations, the covers 2182 could cover an intermediate portion of the paddles 2126, leaving forward and rearward portions exposed. In some configurations, the covers 2182 cover or overlap at least about one-third or one-half of a laterally-outward or forward-facing surface of the paddles 2126. In some configurations, the covers 2182 cover or overlap at least about two-thirds or three-quarters of a laterally-outward or forward-facing surface of the paddles 2126.

In some configurations, the paddle covers 2182 can be configured to provide localized support to a portion of the paddles 2126. For example, the paddle covers 2182 can be in the form of elongate finger structures. Such finger structures can provide support to a relatively small portion of the paddles 2126. The finger structures can originate at any desired location relative to the paddles 2126, such as a forward end, a rearward end or an intermediate portion of the paddles 2126. In some configurations, the finger structures are curved, such as curving toward a rearward direction or curving toward a forward direction. For example, the finger structures can curve to follow a portion or an entirety of an upper peripheral edge of the paddles 2126. Such finger structures can be located at, or spaced from, the peripheral edge of the paddles 2126. In some configurations, the finger structures can be configured to overlap support structures of the paddles 2126, such as the supports 2163 described further below.

Preferably, a space or valley 2184 is defined between the covers 2182. In the illustrated arrangement, the valley 2184 exposes a portion of the mask seal 2104, such as a forward portion of the nasal region 2168, to allow a desired amount of inflation of the mask seal 2104. In addition, such an arrangement can accommodate the tip of a user's nose or can provide space to accommodate a portion of the mask seal 2104 that is deflected by the user's nose.

Figure 22:
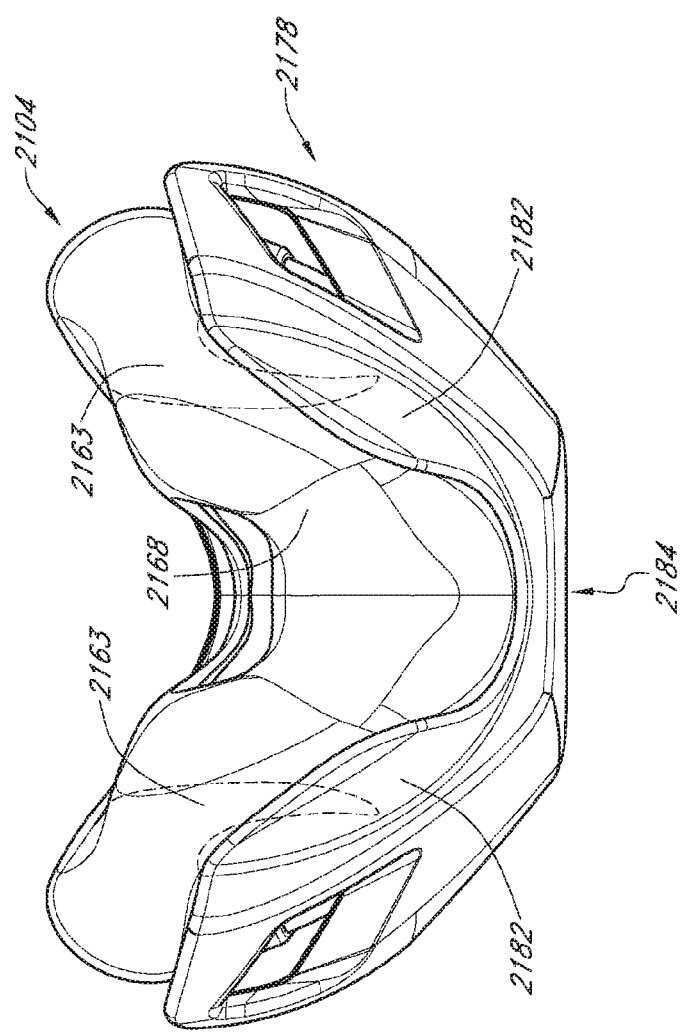
FIG. 22 is a top view of the interface portion of the interface assembly of FIG. 1 illustrating an example placement of support structures of the mask seal.

With reference to FIG. 22, the covers 2182 can cooperate with features of the mask seal 2104 to provide desirable performance characteristics. For example, the supports 2163 for the paddles 2126 can be positioned relative to the covers 2182 such that a load applied to the paddles 2126 by the user's face is transferred to the covers 2182 by the supports 2163. Thus, the supports 2163 can end at or shortly after the portion of the mask seal 2104 that contacts or is positioned adjacent the covers 2182 and may not extend into the upper front portion 2150 or all the way to the mask shell 2102. The supports 2163 can extend in a direction generally from the rearward or user-contacting surface of the mask seal 2104 toward its respective cover 2182. In some configurations, each of the supports 2163 extends generally or substantially in a longitudinal direction of the mask seal 2104. The supports 2163 can extend generally parallel to one another or can be closer at a forward end in comparison to a rearward end. In other words, the supports 2163 can converge in a direction moving from the rearward or user-contacting surface of the mask seal 2104 toward a front portion of the mask seal 2104. However, in other configurations, the supports 2163 can diverge from rear to front.

As described above, the supports 2163 can be in the form of or function in a manner similar to suspension members or springs to provide a resistance force in response to attempted compression or collapse of the paddles 2126 in a fore-aft direction. The thickness, shape, orientation and/or location of the supports 2163 inhibits or prevents collapse because the supports 2163 transmit force into the covers 2182. Because the force is transferred into the covers 2182, collapse of the regions of the mask seal 2104 near or surrounding the supports 2163 (e.g., the nasal region 2168 and/or the upper front portion 2150) is inhibited or prevented. Portions of the mask seal 2104 can deform or stretch, but preferably collapse is inhibited or prevented. Collapse of the seal can involve a loss of shape that causes leaks or other detrimental performance of the mask seal 2104. In some case, collapse involves contact of normally spaced-apart wall portions of the mask seal 2104 (e.g., contact between a relatively rearward wall portion and a relatively forward wall portion). The supports 2163 can also inhibit or prevent collapse of the valley of the mask seal 2104. In other words, the supports 2163 can assist in maintaining the paddles 2126 in a laterally-spaced or separated orientation.

In at least some configurations, the covers 2182 can also provide support for the paddles 2126 in the absence of supports 2163. Moreover, although the covers 2182 (or other similar support structures) are particularly useful for undernose type nasal masks or combined nasal-oral masks, the covers 2182 or similar structures can be utilized in other types of interfaces, as well. For example, the covers 2182 can be utilized in nasal or combined nasal-oral mask assemblies or interfaces that cover, contact or seal against the bridge of the user's nose and/or include a T piece or other type of forehead support, for example and without limitation. The covers 2182 can be utilized, or modified for use, in any locations of an interface in which support against collapsing and/or support against overexpansion may be desirable. Such locations can be at or near the portion of the seal that contacts or extends alongside the user's nose or can be at other locations. As noted above, the covers 2182 can be utilized with or without corresponding supports 2163.

Possible locations of the supports 2163 relative to the covers 2182 are illustrated in FIG. 22. In some configurations, the supports 2163 extend generally between the covers 2182 and rearward surfaces of the paddles 2126 that contact the user's face. Such surfaces can coincide with sides of the nasal region 2168, for example. Forward ends of the supports 2163 can be aligned in a lateral direction with the covers 2182. In some configurations, forward ends of the supports 2163 could join one another, such as with a semi-circular joining portion, for example, and/or could extend all the way or substantially all the way to the mask shell 2102. Such an arrangement could provide greater shape-holding functionality and feedback. However, it has been determined that the covers 2182 allow the supports 2163 to terminate earlier while still providing a desirable amount of shape-holding and feedback. A shape of the supports 2163 can be selected to be complementary with or otherwise provide desired interaction with the covers 2182. Such an arrangement allows at least portions of the nasal region 2168 (e.g., the nasal tip region), if not the entire nasal region 2168, to be relatively thin to provide comfort to the user and/or provide desirable sealing characteristics.

If desired, a structure or structures similar to the supports 2163 (e.g., spring or suspension structures) could be provided in the nose tip area (or other areas of the nasal region 2168) to help maintain a desired shape of the mask seal 2104. It is contemplated that the provision of covers 2182 can permit such supports to have a smaller thickness than would otherwise be provided in the absence of the covers 2182 thereby increasing compliance to improve user comfort and sealing characteristics.

Figure 23:
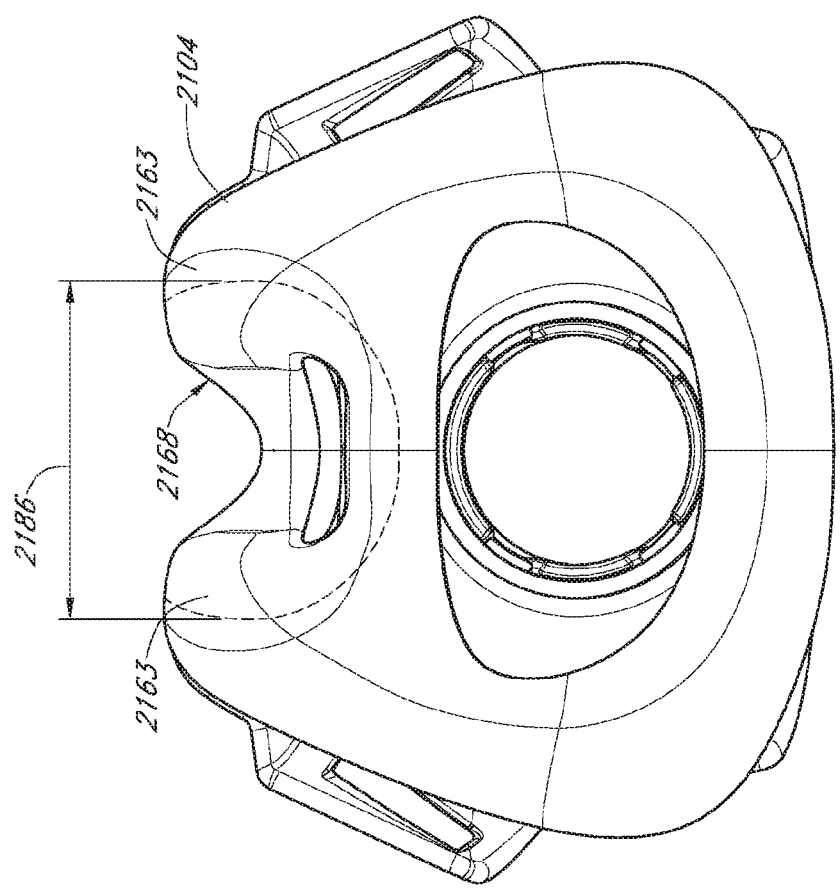
FIG. 23 is a rear view of the interface portion of FIG. 22.
Figure 24:
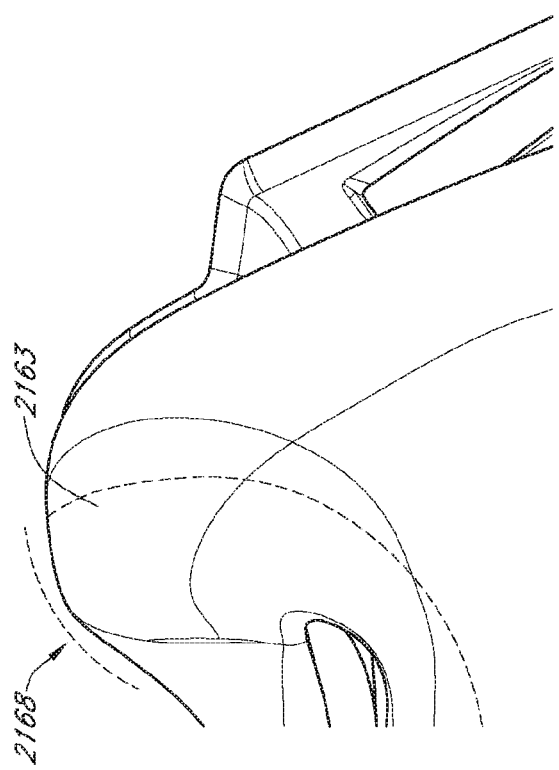
FIG. 24 is a rear view of a portion of the interface portion of FIG. 22.

With reference to FIGS. 23 and 24, rearward or user-contacting surface views of the mask seal 2104 and a portion of the nasal region 2168 are illustrated, respectively. It has been determined that an inner portion of the nasal region 2168 can be a region of the mask seal 2104 that can impact performance and there are certain features or properties that have been discovered to improve seal comfort, leak and overall performance. For example, a width 2186 of the nasal region 2168 or width between the spring structures or supports 2163 can influence seal comfort, leak and overall performance. In some configurations, this width is in the region of about 45 mm to about 50 mm, but could be smaller or larger, such as for different size mask seals 2104.

With reference to FIG. 24, in some configurations, the outer geometry profile of the mask seal 2104 from the spring structure or supports 2163 to the inner portion of the nasal region 2168 is a convex profile. Such an arrangement allows the paddles 2126 to displace away when the user's nose is fitted against the nasal region 2168 and provides a desirable sealing profile around the user's nostrils.

In addition, as described above, a portion or an entirety of the nasal region 2168 has a thickness of between about 0.3 mm and about 0.5 mm or 0.6 mm, in some configurations. In some configurations, at least the inner portion (excluding the nasal opening support 2158) of the nasal region 2168 has a thickness of at least about 0.3 mm to provide a desirable level of compliance while also inhibiting creasing over a range of facial geometries and/or operational pressures. In some configurations, the inner region of the nasal portion 2168 has a constant thickness. However, the thickness could be variable within the inner region of the nasal portion 2168. In some configurations, the thickness of the inner region of the nasal portion 2168 can vary from about 0.3 mm to slightly thicker values. In some configurations, the thickness of a portion or an entirety of the nasal region 2168 could be less than about 0.3 mm, which could provide increased compliance. However, such a thickness can result in creasing with some facial geometries and/or at lower operational pressures.

FIGS. 25-39 illustrate additional mask assemblies 2100 having paddles 2126 and support structure(s) 2182 that provide support to the paddles 2126. The mask assemblies 2100 of FIGS. 25-39, including the paddles 2126 and the support structures 2182, can be similar to or substantially the same as the mask assemblies 2100, paddles 2126 and support structures 2182 described elsewhere herein, including the mask assemblies 2100 of FIGS. 1-24. Accordingly, the same reference numbers used in connection with the mask assemblies 2100 of FIGS. 1-24 are used to refer to the same or corresponding features in the mask assemblies 2100 of FIGS. 25-39. The following description of the mask assemblies 2100 of FIGS. 25-39 is directed primarily toward the differences relative to the previously-described mask assemblies 2100. Features or components of the mask assemblies 2100 of FIGS. 25-39 not specifically described can be the same as or similar to the same or corresponding features or components of the mask assemblies 2100 of FIGS. 1-24, or can be of another suitable arrangement.

Figure 26:
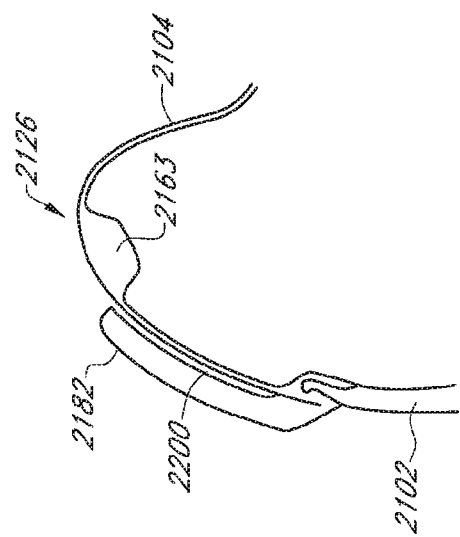
FIG. 26 is a sectional view of a portion of the mask assembly taken along line 26-26 of FIG. 25.
Figure 25:
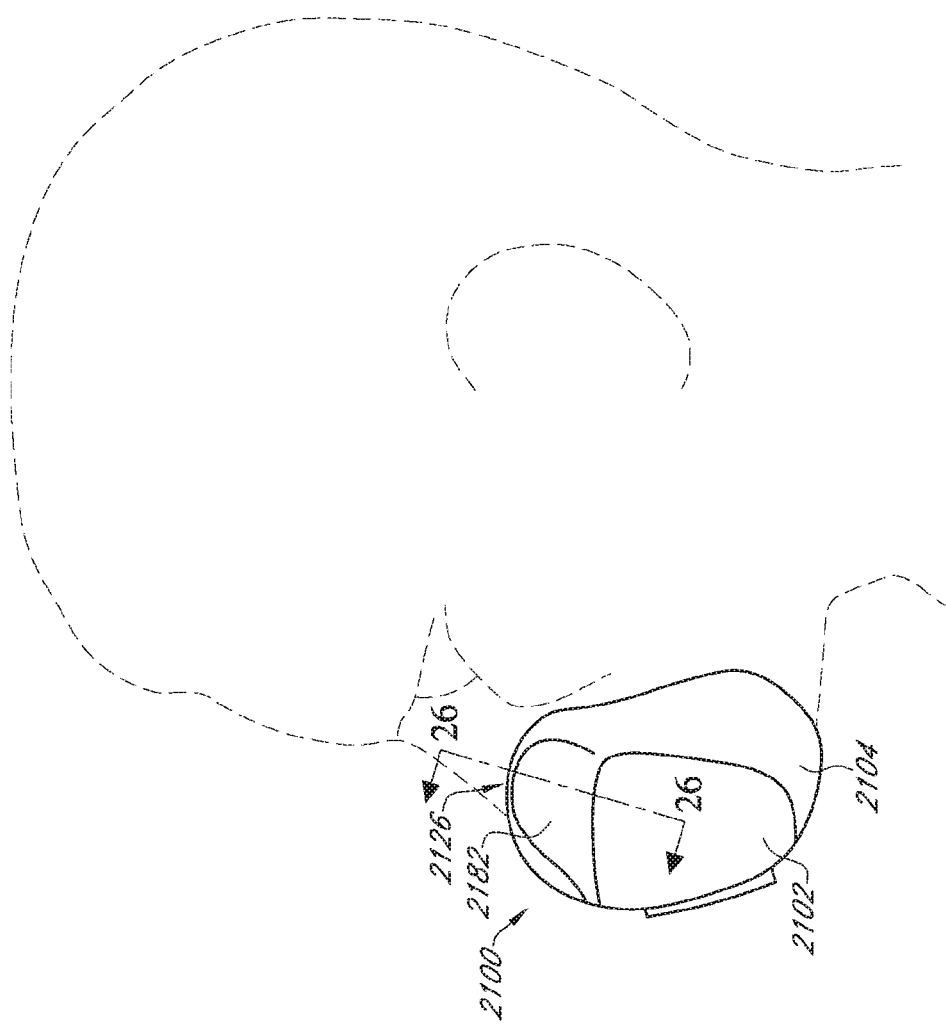
FIG. 25 is a side view of another mask assembly shown in position on the head of a user.

FIGS. 25 and 26 illustrate a mask assembly 2100 positioned on the face of a user. The mask assembly 2100 includes a pair of paddle covers 2182, each of which overlaps at least a portion of a corresponding paddle 2126 of the mask seal 2104. Only one paddle 2126 and paddle cover 2182 is illustrated in FIGS. 25 and 26; however, the mask assembly 2100 can be substantially or completely symmetrical about a central, vertical axis. Accordingly, the paddle 2126 and paddle cover 2182 on the other side of the mask assembly 2100 can be the same as or substantially the same as the illustrated paddle 2126 and paddle cover 2182.

In the illustrated arrangement of FIGS. 25 and 26, the paddle cover 2182 is carried directly by the mask seal 2104 rather than the mask shell 2102. In some configurations, the paddle cover 2182 is a flap portion that is unitarily-formed or formed in one piece with at least a portion of the mask seal 2104. The paddle cover 2182 can be substantially similar in size, shape, location and rigidity as the other paddle covers 2182 described herein. The illustrated paddle cover 2182 is separated from an outer surface of the paddle 2126 such that a space 2200 is defined therebetween, at least in the absence of elevated pressure within the mask assembly 2100. A shape of the paddle cover 2182 can correspond to a shape of the adjacent surface of the paddle 2126 such that a width of the space 2200 is constant. In other configurations, the width of the space 2200 can vary.

In some configurations, the paddle cover 2182 is more rigid than the portion of the paddle 2126 that is covered by or overlapped by the paddle cover 2182. The greater rigidity relative to the paddle 2126 can be accomplished by a variety of arrangements. In the illustrated arrangement, the paddle cover 2182 comprises the same material as the paddle 2126 (e.g., silicone), but has a wall thickness that is greater than the wall thickness of a corresponding wall portion of the paddle 2126. In some configurations, the wall thickness of the paddle cover 2182 is at least twice the wall thickness of the corresponding portion of the paddle 2126. In some configurations, the wall thickness of the paddle cover 2182 is at least three times the wall thickness of the corresponding portion of the paddle 2126. In some configurations, the wall thickness of the paddle cover 2182 is at least four times or about four times the wall thickness of the corresponding portion of the paddle 2126. The paddle cover 2182 can have a constant or variable wall thickness. The wall thickness can vary to vary the rigidity of the paddle cover 2182 to provide different levels of support to different portions of the paddle 2126.

Other suitable arrangements for the paddle cover 2182 can also be used. For example, the paddle cover 2182 could be constructed in whole or in part from a stiffer material than the material of the paddle 2126. In some configurations, the materials can be similar (e.g., silicone materials having different stiffness properties). The paddle cover 2182 can be coupled or connected to a remaining portion of the mask seal 2104 by any suitable process or arrangement. For example, the paddle cover 2182 and remaining portion of the mask seal 2104 can be constructed in a multiple shot injection molding process (e.g., over-molding or co-molding). In other configurations, the paddle cover 2182 can be constructed as a separate component and coupled to the remaining portion of the mask seal 2104, such as by adhesives, welding, mechanical fasteners or other suitable arrangements.

Figure 27:
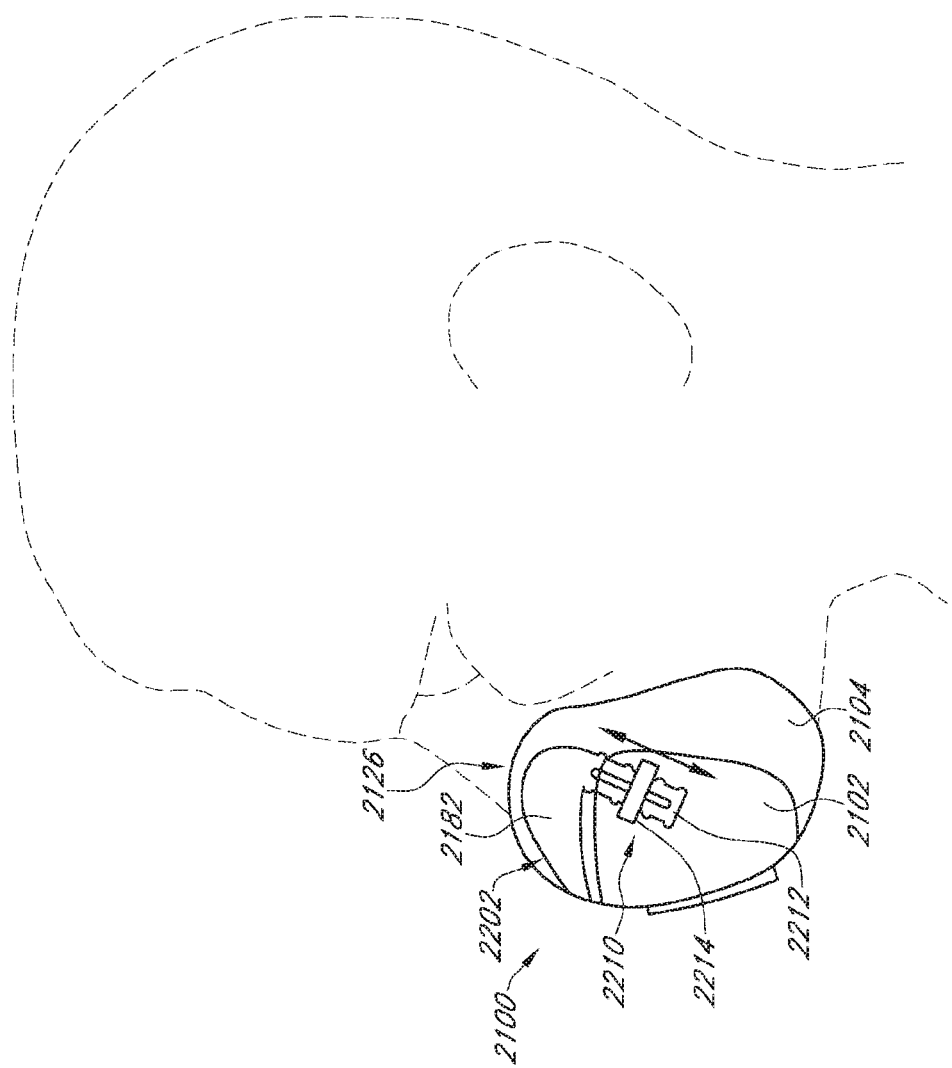
FIG. 27 is a side view of another mask assembly having an adjustable support for an upper portion of the mask seal shown in position on the head of a user.

FIG. 27 illustrates an adjustable support structure 2202 for the paddles 2126. In the illustrated arrangement, the adjustable support structure 2202 is a single structure that defines a pair of paddle cover portions 2182 (hereinafter, "paddle covers"). In other configurations, the paddle covers 2182 can be defined by separate structures. The support structure 2202 can be moved relative to the paddles 2126 and/or a remainder of the mask assembly 2100. In the illustrated arrangement, the support structure 2202 is movable to a desired one of a plurality of possible discrete adjustment positions. However, in other configurations, the support structure 2202 can be infinitely adjustable.

The mask assembly 2100 of FIG. 27 comprises an adjustment mechanism 2210 that permits adjustment of the support structure 2202 relative to the paddles 2126 and/or remainder of the mask assembly 2100. The adjustment mechanism 2210 comprises a detent assembly that allows the support structure 2202 to be secured in a selected one of a plurality of adjustment positions, such as 3, 4 or 5 adjustment positions, for example and without limitation. The illustrated adjustment mechanism 2210 comprises an elongate arm 2212 that extends downwardly from the paddle covers 2182 of the support structure 2202. The elongate arm 2212 comprises a plurality of protrusions that define adjustment positions therebetween. The mask shell 2102 (or another portion of the mask assembly 2100, such as the mask seal 2104) comprises a slot 2214 configured to receive the elongate arm 2212. The elongate arm 2212 can be secured within the slot 2214 at any one of the plurality of adjustment positions. A downwardly-projecting elongate arm 2212 is advantageous in that it can position the elongate arm 2212 out of the field of view of the user. In other configurations, however, the illustrated arrangement can be reversed and the elongate arm 2212 can be provided on the mask assembly 2100 (e.g., the mask shell 2102 or mask seal 2104) and the slot 2214 can be defined by the support structure 2202. Other suitable detent arrangements can also be used.

The support structure 2202 can adjust in any desired direction relative to the paddles 2126 and/or the remaining portion of the mask assembly 2100. In some configurations, the support structure 2202 is adjustable in a vertical direction relative to the paddles 2126 and/or the remaining portion of the mask assembly 2100. In some configurations, the support structure 2202 is adjustable in a horizontal or fore-aft direction relative to the paddles 2126 and/or the remaining portion of the mask assembly 2100. In the illustrated arrangement, the support structure 2202 is adjustable in both the vertical and horizontal direction relative to the paddles 2126 and/or the remaining portion of the mask assembly 2100. Thus, the support structure 2202 moves up and back in one adjustment direction and down and forward in the other adjustment direction. The direction of adjustment can be generally perpendicular to the upper surface 2130 (FIG. 8) of the mask seal 2104 and/or the underside of the user's nose when the mask assembly 2100 is properly positioned on the user's face. The direction of adjustment can be otherwise configured to provide desirable adjustment to the support offered to the paddles 2126.

Figure 29:
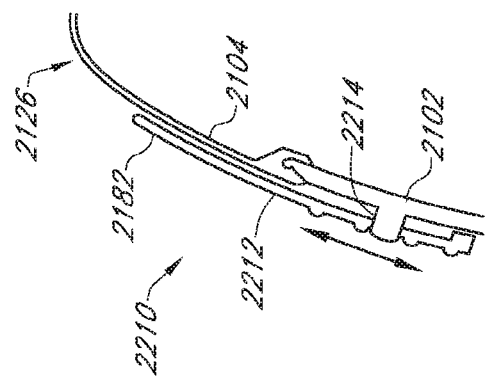
FIG. 29 is a sectional view of a portion of the mask assembly taken along line 29-29 of FIG. 28.
Figure 28:
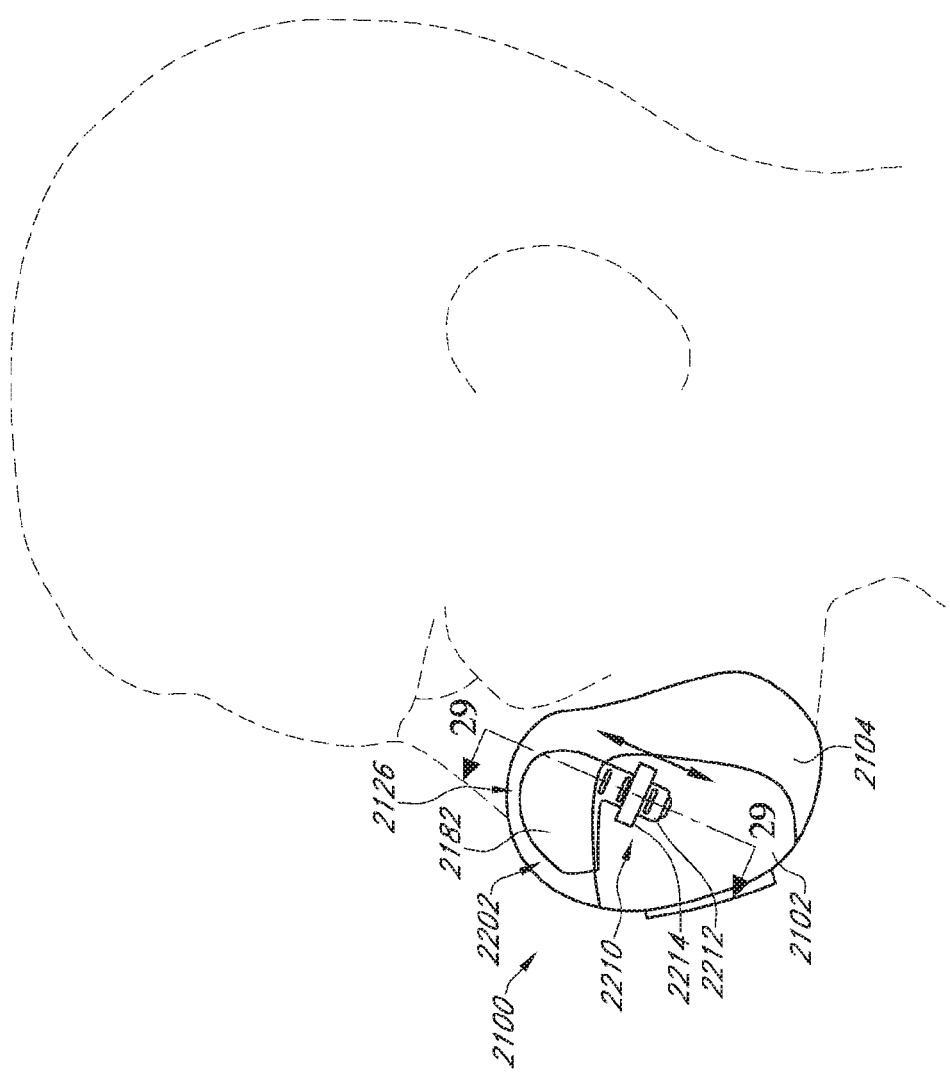
FIG. 28 is a side view of yet another mask assembly having an alternative adjustable support for the upper portion of the mask seal shown in position on the head of a user.

FIGS. 28 and 29 illustrate a mask assembly 2100 comprising an adjustable support structure 2202 for the paddles 2126. The adjustable support structure 2202 is similar in many respects to the adjustable support structure 2202 of FIG. 27. However, in the arrangement of FIGS. 28 and 29, the adjustable support structure 2202 comprises individual structures for each of the paddle cover portions 2182 (hereinafter, "paddle covers"). Each of the support structures 2202 can be moved individually relative to the paddles 2126 and/or a remainder of the mask assembly 2100. The support structures 2202 are movable to a desired one of a plurality of possible discrete adjustment positions. However, in other configurations, the support structures 2202 can be infinitely adjustable.

The mask assembly 2100 of FIGS. 28 and 29 comprises an adjustment mechanism 2210 associated with each support structure 2202 that permits adjustment of the support structures 2202 relative to the paddles 2126 and/or remainder of the mask assembly 2100. The adjustment mechanisms 2210 comprise a detent assembly that allows the support structure 2202 to be secured in a selected one of a plurality of adjustment positions, such as 3, 4 or 5 adjustment positions, for example and without limitation. Each of the illustrated adjustment mechanisms 2210 comprises an elongate arm 2212 that extends downwardly from the paddle cover 2182 of the support structure 2202. The elongate arm 2212 comprises a plurality of protrusions that define adjustment positions therebetween. In contrast to the arrangement of FIG. 27, however, the protrusions are provided on a face (e.g., an outwardly-facing surface) of the elongate arm 2212 instead of the edge protrusions of FIG. 27. The mask shell 2102 (or another portion of the mask assembly 2100, such as the mask seal 2104) comprises a slot 2214 configured to receive the elongate arm 2212. The elongate arm 2212 can be secured within the slot 2214 at any one of the plurality of adjustment positions. As in FIG. 27, the elongate arms 2212 of FIGS. 28 and 29 are downwardly-projecting to position the elongate arm 2212 out of the field of view of the user. In other configurations, however, the illustrated arrangement can be reversed and the elongate arm 2212 can be provided on the mask assembly 2100 (e.g., the mask shell 2102 or mask seal 2104) and the slot 2214 can be defined by the support structure 2202. Other suitable detent arrangements can also be used.

Similar to the support structure 2202 of FIG. 27, the support structure 2202 of FIGS. 28 and 29 can be adjustable in any desired direction relative to the paddles 2126 and/or the remaining portion of the mask assembly 2100, such as in a vertical direction, horizontal direction or a combination of the vertical and horizontal directions. The direction of adjustment can be generally perpendicular to the upper surface 2130 (FIG. 8) of the mask seal 2104 and/or the underside of the user's nose when the mask assembly 2100 is properly positioned on the user's face. The direction of adjustment can be otherwise configured to provide desirable adjustment to the support offered to the paddles 2126.

Figure 30:
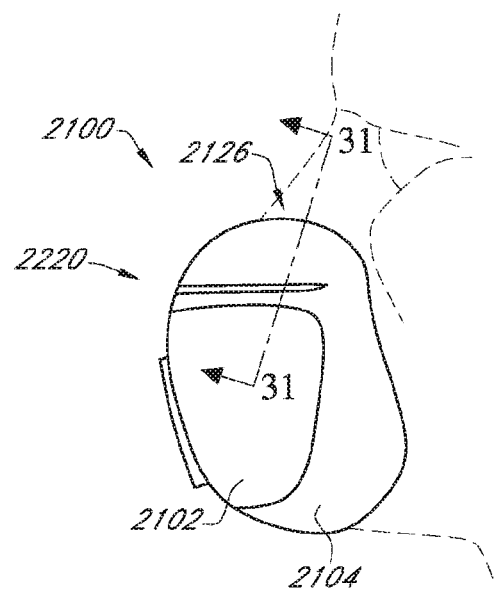
FIG. 30 is a side view of another mask assembly having a hinge portion within the mask seal.
Figure 31:
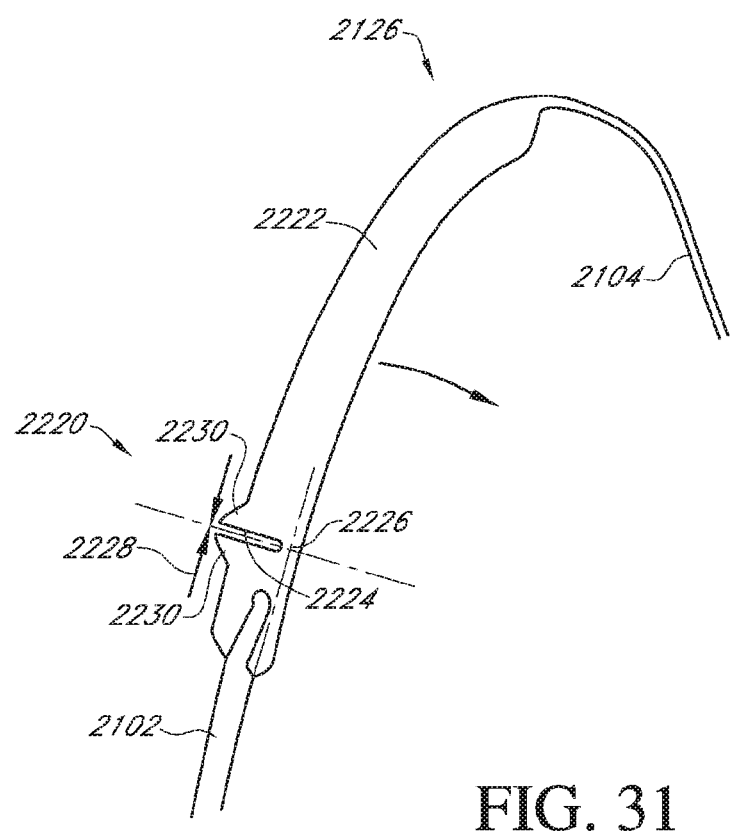
FIG. 31 is a sectional view of a portion of the mask assembly taken along line 31-31 of FIG. 30.

FIGS. 30 and 31 illustrate a mask assembly 2100 comprising a hinge arrangement 2220 configured to facilitate movement of the paddles 2126 or a portion of the paddles 2126 relative to another portion of the mask seal 2104 or mask assembly 2100, such as a portion of the mask seal 2104 below the paddles 2126 and/or upon which the paddles 2126 are supported. In some configurations, the hinge arrangement 2220 is configured to permit at least a portion of the paddles 2126 to move inwardly from a relaxed or normal position. In particular, in the illustrated arrangement, the hinge arrangement 2220 is configured to allow a laterally outer wall 2222 of the paddles 2126 to move inwardly from a relaxed or normal position. In some configurations, the hinge arrangement 2220 is configured to allow the paddles 2126 to move inwardly in response to a sufficient force applied to the upper surface 2130 (FIG. 8) of the mask seal 2104. Thus, the hinge arrangement 2220 may allow the paddles 2126 to move inwardly from any starting position (e.g., an inflated or expanded position) prior to the force being applied to the upper surface 2130.

The hinge arrangement 2220 can be substantially or completely unidirectional. That is, the hinge arrangement 2220 can facilitate movement of the paddles 2126 or a portion thereof in one direction and restrict, inhibit or prevent movement of the paddles 2126 or a portion thereof in another direction. For example, the illustrated hinge arrangement 2220 is configured to permit inward movement of at least the outer wall 2222 of the paddles 2126 and restrict outward movement of at least the outer wall 2222 of the paddles 2126. The hinge arrangement 2220 allows a small amount of outward movement of at least the outer wall 2222 of the paddles 2126, which preferably is significantly less than the amount of inward movement permitted.

In some configurations, the hinge arrangement 2220 comprises a living hinge defined by an inwardly-extending slot 2224 defined in the mask seal 2104. The slot 2224 preferably extends substantially perpendicular to a laterally outward surface of the paddle 2126 from which the slot 2224 extends. The slot 2224 can be located at or near a lower end of the paddles 2126. The slot 2224 can extend into the outer wall 2222 any desired distance, which can influence the ease with which the outer wall 2222 can deflect or move about a hinge axis 2226 defined by the hinge arrangement 2220. In general, the further the slot 2224 extends through the outer wall 2222, the easier the outer wall 2222 can deflect or move about the hinge axis 2226 due to the reduced wall thickness at the end of the slot 2224. In some configurations, the slot 2224 extends at least about one-half of the thickness of the outer wall 2222 at the location of the hinge arrangement 2220. In some configurations, the slot 2224 extends at least about three-quarters of the thickness of the outer wall 2222 at the location of the hinge arrangement 2220.

The slot 2224 can define a width 2228. The width 2228 can influence the amount of outward movement permitted by the outer wall 2222. In general, the greater the width 2228, the further the outer wall 2222 is able to move outward as a result of the hinge arrangement 2220. The hinge arrangement 2220 can permit outward movement of the outer wall 2222 until opposing surfaces of the slot 2224 contact one another. In some configurations, the width 2228 is less than about one-half of the length of the slot 2224. In some configurations, the width 2228 is less than about one-quarter of the length of the slot 2224. In the illustrated arrangement, the hinge arrangement 2220 comprises a projection 2230 that projects outwardly on each side of the slot 2224. The projection 2230 can provide a localized increase in the wall thickness of the outer wall 2222 and can limit outward movement of the outer wall 2222 relative to movement that would be permitted by a relatively reduced wall thickness because the free ends of opposing surfaces of the slot 2224 are further from the hinge axis 2226 and will contact one another at a smaller deflection angle than free ends that are closer to the hinge axis 2226.

In the illustrated arrangement, the hinge arrangement 2220 comprises a single slot 2224 that extends generally in a lateral direction from the paddle 2126 on one side of the mask assembly 2100 to the paddle 2126 on the other side of the mask assembly 2100. However, in other configurations, a pair of slots 2224 can be provided, with each of the slots 2224 associated with one of the paddles 2126.

The paddle 2126 illustrated in FIGS. 30 and 31 includes a thickened outer wall 2222. As a result, the outer wall 2222 has greater rigidity than other portions of the paddle 2126. Other suitable methods or arrangements for creating greater rigidity in the outer wall 2222 can also be employed. The thickened outer wall 2222 can reduce or eliminate the need for paddle supports (e.g., paddle covers 2182) with the mask assembly 2100 of FIGS. 30 and 31. Moreover, the provision of a hinge arrangement 2220 in combination with a thickened or otherwise stiffened outer wall 2222 can control outward movement or expansion of the paddles 2126 while permitting inward movement of the paddles 2126 in a manner similar to less rigid paddles 2126 in combination with paddle supports 2182. However, in some configurations, the thickened or otherwise stiffened outer wall 2222 can be used in combination with paddle covers 2182 or other paddle supports, such as any of the paddle supports disclosed herein.

Figure 33:
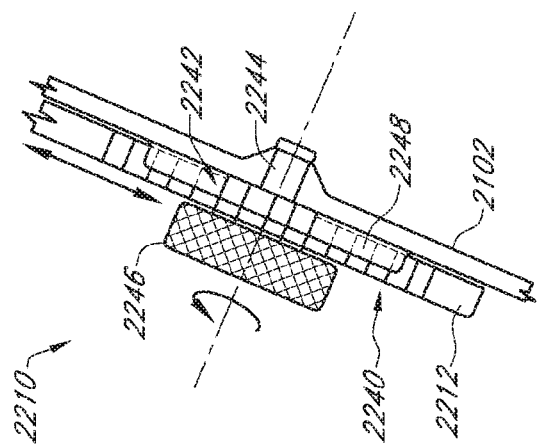
FIG. 33 is a sectional view of a portion of the mask assembly taken along line 33-33 of FIG. 32.
Figure 32:
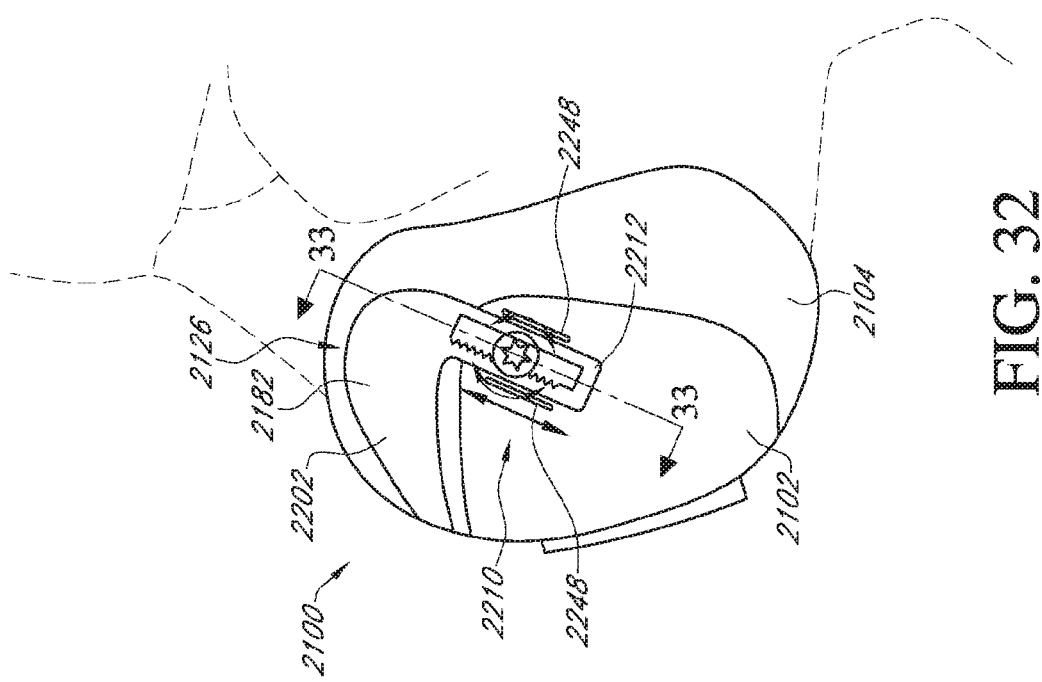
FIG. 32 is a side view of another mask assembly having an alternative adjustable support for the upper portion of the mask seal shown in position on the head of a user.

FIGS. 32 and 33 illustrate another adjustable support structure 2202 for the paddles 2126 that is similar in some respects to the adjustable support structures 2202 of FIGS. 27-29. Features or components not specifically described with respect to FIGS. 32 and 33 can be the same as or similar to the same or corresponding features or components of the supports structures 2202 of FIGS. 27-29. In the illustrated arrangement, the adjustable support structure 2202 is a single structure that defines a pair of paddle cover portions 2182 (hereinafter, "paddle covers"). In other configurations, the paddle covers 2182 can be defined by separate structures. As described above, the support structure 2202 can adjust in any desired direction relative to the paddles 2126 and/or the remaining portion of the mask assembly 2100, such as a vertical direction, horizontal or fore-aft direction or a combination of vertical and horizontal direction.

The support structure 2202 can be moved relative to the paddles 2126 and/or a remainder of the mask assembly 2100 by an adjustment mechanism 2210 comprising a rack and pinion arrangement. The adjustment mechanism 2210 can comprise a rack and pinion arrangement associated with each paddle cover 2182 or can include a single rack and pinion that adjusts both paddle covers 2182 of the support structure 2202. The illustrated adjustment mechanism 2210 comprises an elongate arm 2212 that extends downwardly from the paddle covers 2182 of the support structure 2202. The elongate arm 2212 comprises a plurality of teeth that define a rack 2240. The rack 2240 extends in a length direction of the elongate arm 2212. The mask shell 2102 (or another portion of the mask assembly 2100, such as the mask seal 2104) comprises a gear or pinion 2242 having teeth that engage the teeth of the rack 2240.

In the illustrated arrangement, the pinion 2242 comprises a mounting shaft 2244 that passes through an opening in the mask shell 2102. The mounting shaft 2244 can couple the pinion 2242 to the mask shell 2102 via a snap-fit coupling comprising an enlarged end portion of the shaft 2244 that is able to pass through the opening in the mask shell 2102 in response to deliberate assembly force, but resists passing back through the opening to retain the shaft 2244 and pinion 2242 on the mask shell 2102. The pinion 2242 is rotatable relative to the shaft 2244 and/or the mask shell 2102. A rotational adjuster, such as an adjustment knob 2246, is coupled to the pinion 2242 and includes a gripping surface that permits a user to manually rotate the knob 2246 to adjust a position or height of the support structure 2202. In other configurations, the rotational adjuster 2246 can allow or require a tool for adjustment. In some configurations, the rotational adjuster 2246 may not be manually adjustable. In some configurations, however, the illustrated arrangement can be reversed and the elongate arm 2212 can be provided on the mask assembly 2100 (e.g., the mask shell 2102 or mask seal 2104) and the pinion 2242 can be coupled to the support structure 2202. The adjustment mechanism 2210 can comprise a guide 2248, such as a rib, that guides movement of the support structure 2202 and/or inhibits or prevents rotation of the support structure 2202 relative to the mask shell 2102 or mask seal 2104.

In an alternative arrangement, the support structure 2202 and/or paddle covers 2182 are configured to pivot inwardly in a direction toward the paddles 2126 and outwardly in a direction away from the paddles 2126 in addition or in the alternative of movement in other directions. In such an arrangement, the adjustment mechanism 2210 can be configured to pivot the support structure 2202 and/or paddle covers 2182 about a pivot axis, which can be a generally horizontal axis located at or near a lower end of the paddles 2126. Such an arrangement can allow the level of support provided to the paddles 2126 to be adjusted. In addition, such an arrangement can permit inward displacement of the paddles 2126 if necessary or desired to address a particular user's facial geometry. Furthermore, the support structure 2202 and/or paddle covers 2182 can be moved away from the paddles 2126 to allow outward expansion of the paddles 2126 when appropriate or desired.

Figure 35:
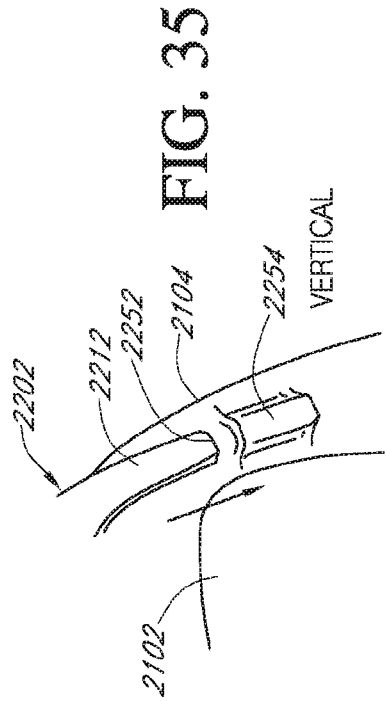
FIG. 35 is a perspective view of a portion of another mask assembly having a removable support including an alternative connection arrangement.
Figure 36:
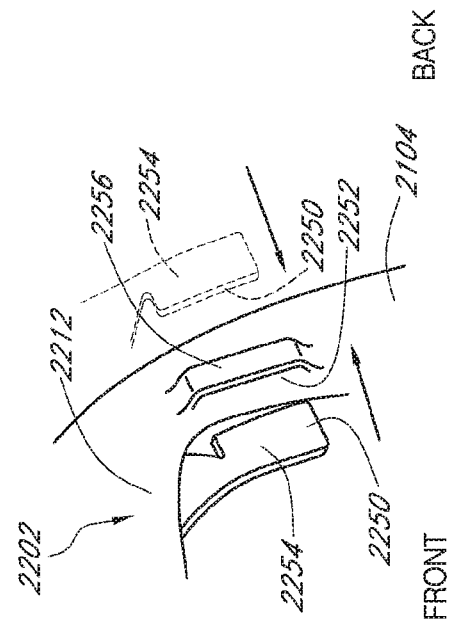
FIG. 36 is a perspective view of a portion of another mask assembly having a removable support including another alternative connection arrangement.
Figure 34:
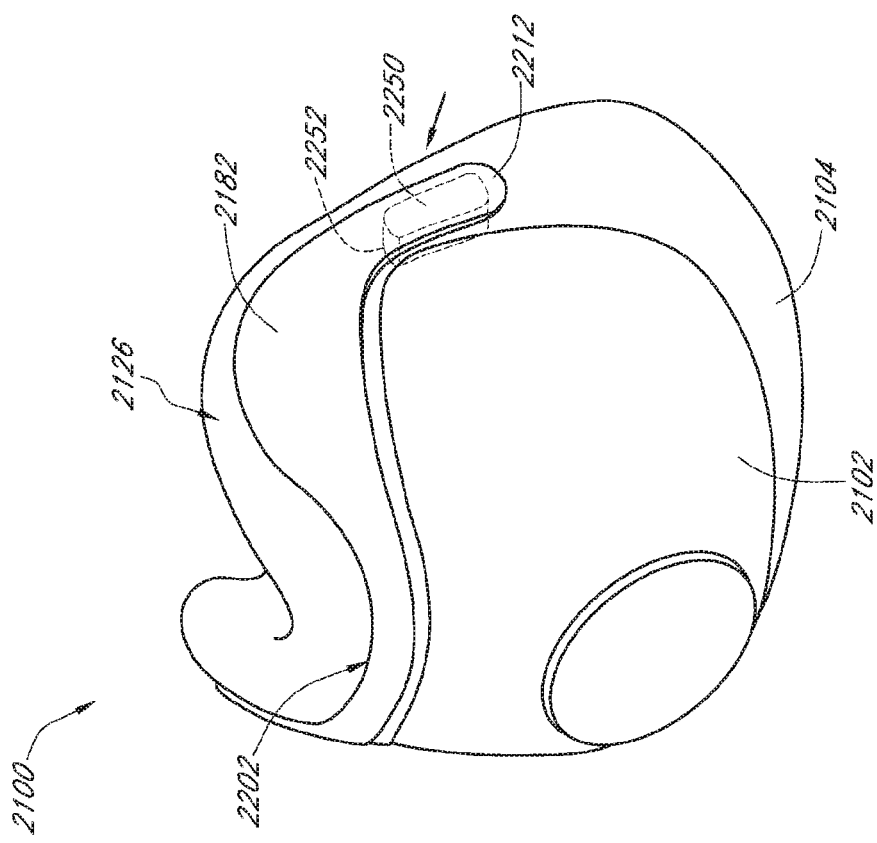
FIG. 34 is a perspective view of another mask assembly having a removable support for the upper portion of the mask seal.

FIGS. 34-36 illustrate various embodiments of removable support structures 2202 for the paddles 2126 that are similar in some respects to the support structures 2202 of FIGS. 27-29, 32 and 33. Features or components not specifically described with respect to FIGS. 34-36 can be the same as or similar to the same or corresponding features or components of the supports structures 2202 of FIGS. 27-29, 32 and 33. In the illustrated arrangement, each of the removable support structures 2202 is a single structure that defines a pair of paddle cover portions 2182 (hereinafter, "paddle covers"). In other configurations, the paddle covers 2182 can be defined by separate structures.

The support structure 2202 of FIG. 34 comprises a protrusion 2250 that extends inwardly from a lower end portion of each downwardly-extending side arm portion 2212 of the support structure 2202. The protrusion 2250 is received within an inwardly-extending pocket or recess 2252 of the mask seal 2104 when the support structure 2202 is coupled to the remainder of the mask assembly 2100. In other configurations, the pocket 2252 can be defined by another portion of the mask assembly 2100, such as the mask shell 2102, for example and without limitation. The protrusion 2250 can be retained within the pocket 2252 by frictional engagement, by a snap-fit, by another interlocking arrangement and/or by the resiliency of the support structure 2202, among other possibilities. In some configurations, multiple sizes and/or shapes of support structures 2202 can be available for a particular mask assembly 2100 to, for example, provide for greater or less support or deflection of the paddles 2126. As with other support structures 2202 disclosed herein, the rigidity of the support structure 2202 can be configured to provide a desired level of support to the paddles 2126.

The support structure 2202 of FIG. 35 can be substantially similar in many respects to the support structure 2202 of FIG. 34. Features or components not specifically described with respect to FIG. 35 can be the same as or similar to the same or corresponding features or components of the supports structure 2202 of FIG. 34, to other support structures disclosed herein or can be of any other suitable arrangement. The support structure 2202 of FIG. 35 has end portions 2254 of the side arms 2212 that are configured to be received within vertically-oriented pockets 2252 in the mask seal 2104. However, in other configurations, the pockets 2252 can be defined by another portion of the mask assembly 2100, such as the mask shell 2102, for example and without limitation.

The support structure 2202 of FIG. 36 can be substantially similar in many respects to the support structures 2202 of FIG. 34 or 35. Features or components not specifically described with respect to FIG. 36 can be the same as or similar to the same or corresponding features or components of the supports structure 2202 of FIG. 34 or 35, to other support structures disclosed herein or can be of any other suitable arrangement. End portions 2254 of the side arms 2212 of the support structure 2202 of FIG. 36 can comprise protruding portions or engagement portions 2250 that are configured to be received within a respective slot or opening 2252 of the mask seal 2104 or other portion of the mask assembly 2100 (e.g., the mask shell 2102). The engagement portions 2250 can be aligned with the remainder of the side arms 2212. The mask seal 2104 or other portion of the mask assembly 2100 can comprise a strap 2256, wall or other suitable structure that at least partially defines the slot 2252. With such an arrangement, the support structure 2202 can be clipped onto the mask assembly 2100 in such instances that additional support of the paddles 2126 is desired. As illustrated in FIG. 36, the support structure 2202 can be configured to clip onto the mask assembly 2100 from multiple directions, such as by movement in a forward direction or movement in a rearward direction.

Figure 37:
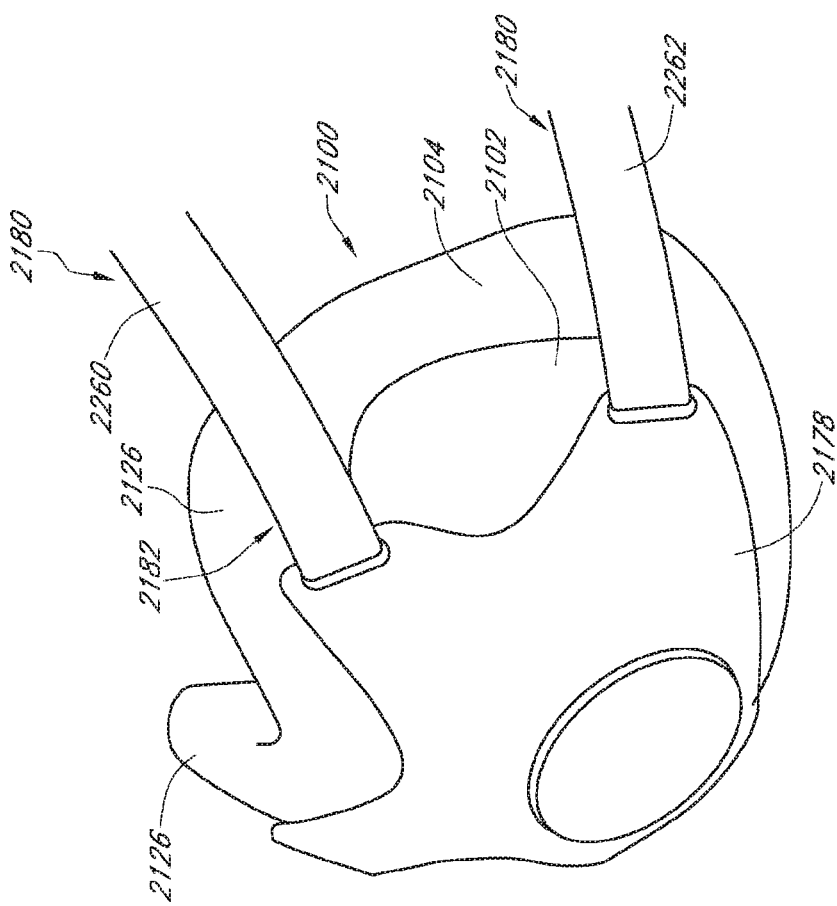
FIG. 37 is a perspective view of another mask assembly that utilizes the headgear as a support for the upper portion of the mask seal.

In some configurations, portions of the interface assembly the primarily serve another function can also be utilized to provide support to the paddles 2126. For example, as illustrated in FIG. 37, the interface assembly can be configured such that a portion of the headgear 2180 is positioned to overlap at least a portion of the paddles 2126. The portion of the headgear 2180 can provide the same or similar function as the paddle covers 2182 described herein. In such an arrangement, adjustment of the headgear 2180, such as headgear position and/or tension, can adjust the amount of support provided to the paddles 2126. In general, greater tension in the headgear 2180 results in greater support or greater deflection of the paddles 2126. The headgear 2180 tension can be increased to move the paddles 2126 inwardly toward one another or decreased to allow the paddles 2126 to move outwardly away from one another.

In the illustrated arrangement, the headgear 2180 comprises an upper strap 2260 and a lower strap 2262 on each side of the interface assembly. In some configurations, the upper strap 2260 is positioned to overlap at least a portion of the paddles 2126; however, in other configurations, other portions of the headgear 2180 can be utilized to function as support for the paddles 2126. In the illustrated arrangement, the upper strap 2260 and lower strap 2262 are connected to a frame 2178, which is connected to the mask assembly 2100. The upper strap 2260 or other portion of the headgear 2180 can be positioned to overlap the paddle 2126 as a result of the headgear 2180 shape and/or mounting location on the frame 2178 or can be guided or deflected into a position to overlap the paddle 2126 by a guiding structure, such as a slot or passage, which in some cases could be an integral portion of the mask seal 2104. As described above and illustrated in FIGS. 1-3, a portion of the frame 2178 can include or carry a support for the paddles 2126. Accordingly, in some configurations, both a portion of the headgear 2180 and the frame 2178 can provide support for the paddles 2126.

Figure 38:
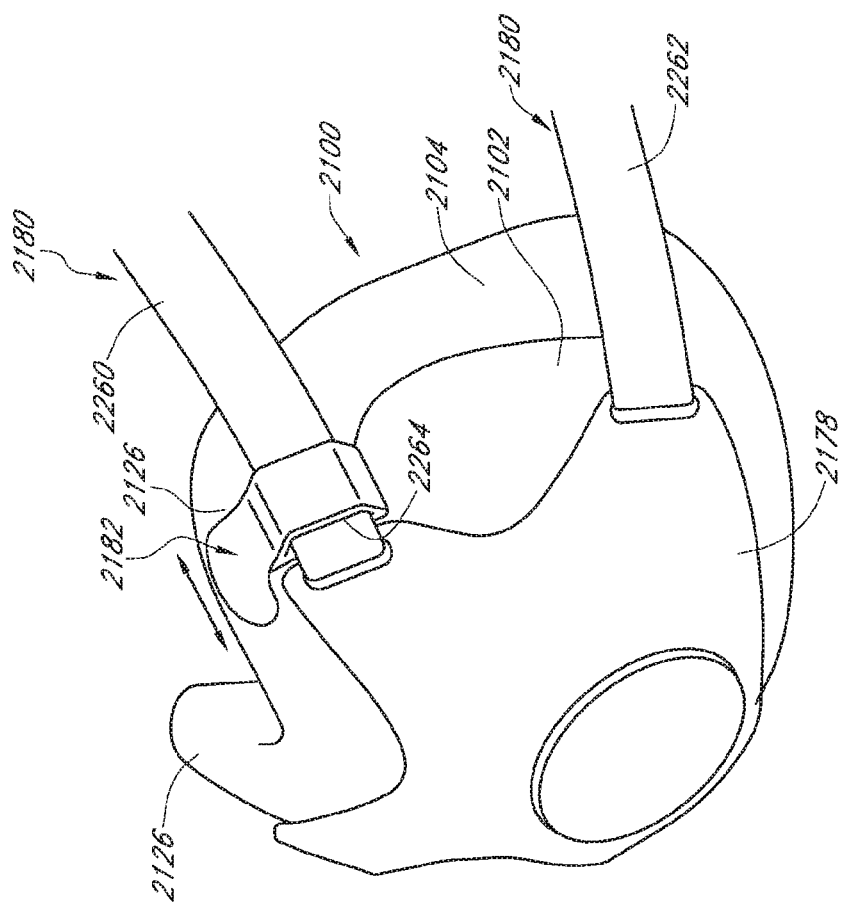
FIG. 38 is a perspective view of another mask assembly in which the headgear carries a support for the upper portion of the mask seal.

With reference to FIG. 38, the headgear 2180 can carry one or more paddle supports or paddle covers 2182 configured to provide support to the paddles 2126. For example, each of the upper straps 2260 can carry a paddle cover 2182 that can be positioned on the strap 2260 to provide support to the corresponding paddle 2126. In some configurations, the paddle cover 2182 comprises an opening 2264 through which the headgear strap 2260 can pass and the paddle cover 2182 can be slid along the strap 2260 into a desired position relative to the paddle 2126. The paddle cover 2182 can be held in position on the strap 2260 by frictional engagement between the paddle cover 2182 and the strap 2260. Similar to the arrangement of FIG. 37, adjustments to the headgear 2180 can adjust the level of support or deflection provided to the paddles 2126 by the paddle covers 2182. Different sizes and/or shapes of paddle covers 2182 can be provided to tune the amount of support or deflection provided to the paddles 2126.

Figure 39:
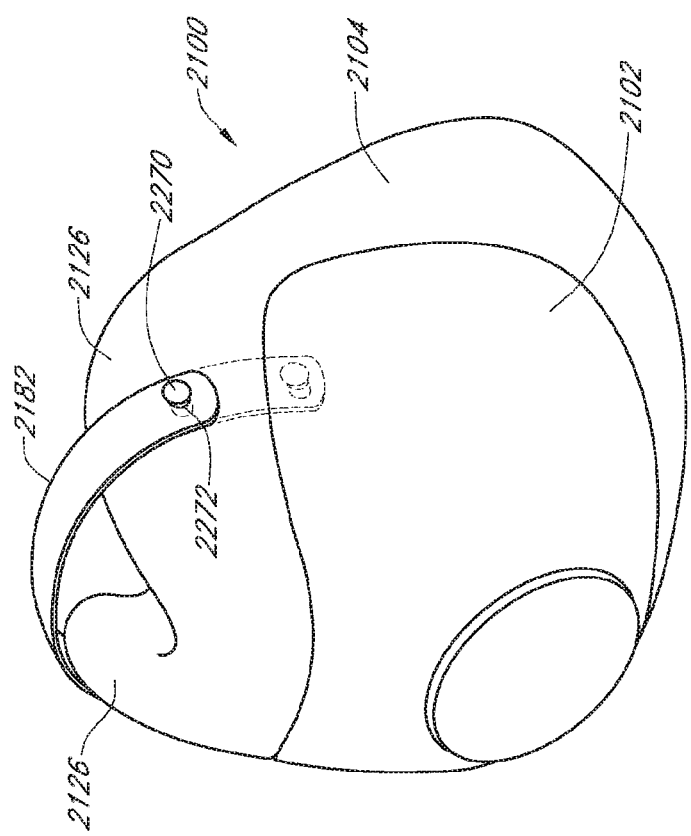
FIG. 39 is a perspective view of another mask assembly having a tether or strap that provides support for the upper portion of the mask seal.
Figure 40:
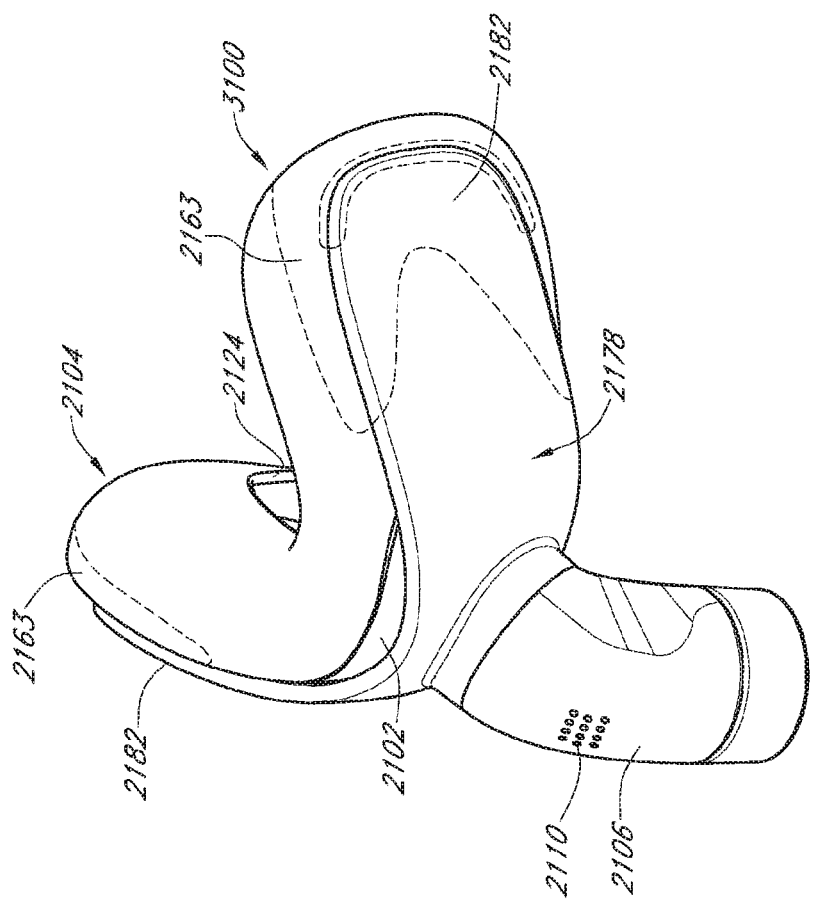
FIG. 40 is a perspective view of another interface assembly having certain features, aspects and advantages of the present disclosure.
Figure 41:
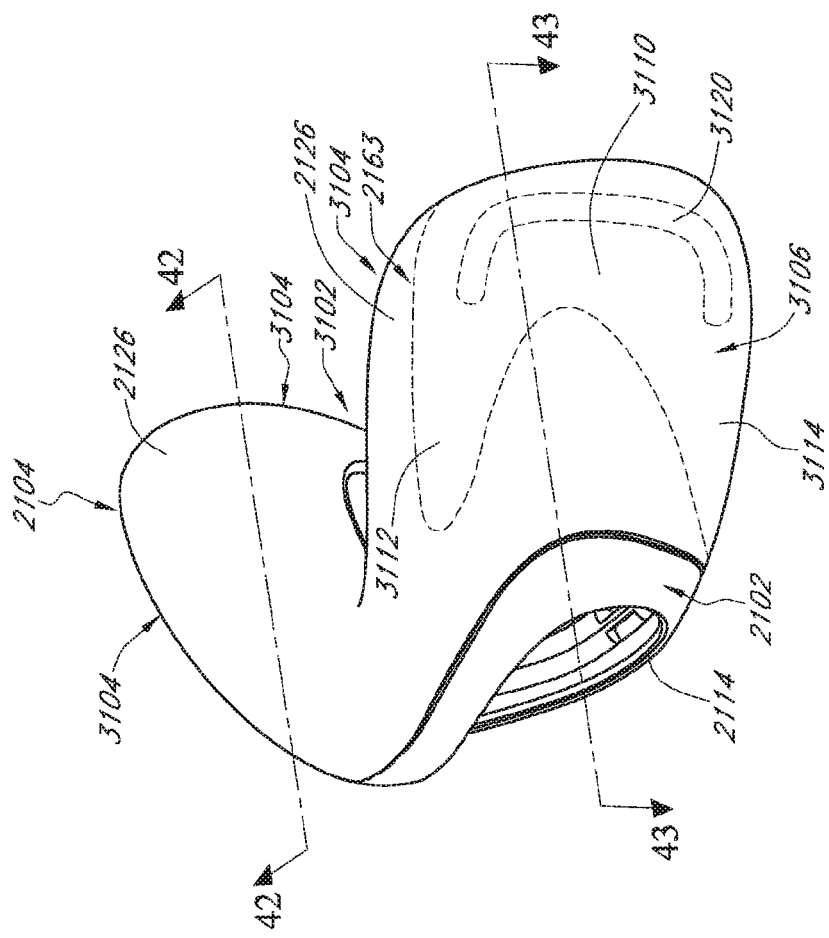
FIG. 41 is a perspective view of a mask assembly of the interface assembly of FIG. 40.
Figure 42:
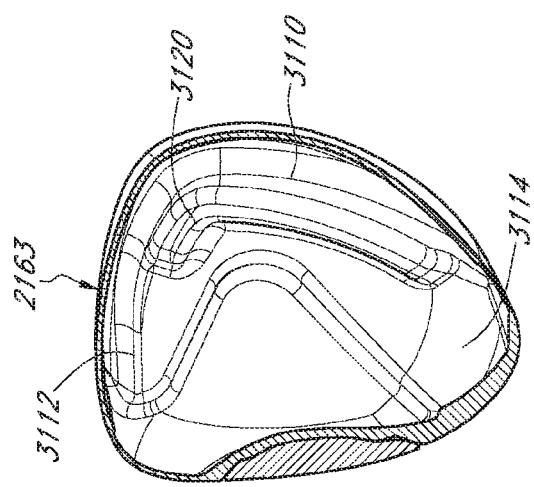
FIG. 42 is a sectional view of the mask assembly taken along line 42-42 of FIG. 41.
Figure 43:
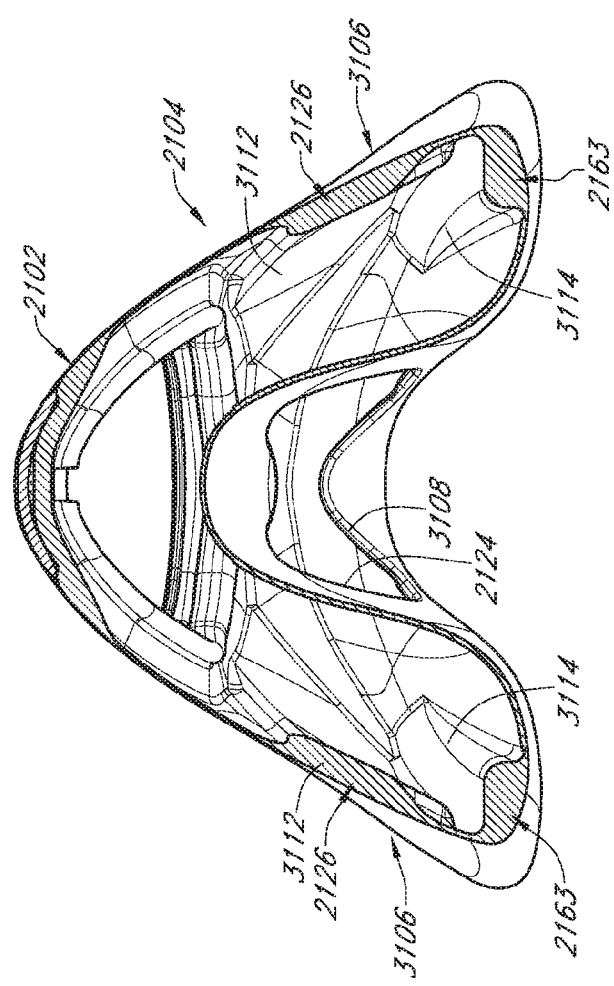
FIG. 43 is a sectional view of the mask assembly taken along line 43-43 of FIG. 41.

FIG. 39 illustrates a support arrangement for the paddles 2126 in the form of a tether or strap 2182. The strap 2182 can be coupled to each side of the mask assembly 2100 and can pass over the paddle 2126 on each side of the mask assembly 2100 to provide support to and/or deflection of the paddles 2126. In the illustrated arrangement, the strap 2182 passes over the top of the mask seal 2104 such that a portion of the strap 2182 is located above the upper surface 2130 (FIG. 8) of the mask seal 2104. The strap 2182 can be rigid or semi-rigid such that it can hold a curved or other shape in the absence of external forces acting on the strap 2182. In other configurations, the strap 2182 can be non-rigid or flexible and can rely on the resistance provided by the paddles 2126, other portion of the mask seal 2104, mask shell 2102 or another portion of the mask assembly 2100 to shape the strap 2182 in use. For example, the paddles 2126 can support a central portion of the strap 2182 and maintain the strap 2182 away from the nose of the user.

The strap 2182 can be coupled to the mask assembly 2100 by any suitable arrangement. In some configurations, the mask seal 2104, mask shell 2102 or another portion of the mask assembly 2100 can include a mounting element that engages a corresponding mounting element of the strap 2182. The strap 2182 can be coupled to each side of the mask assembly 2100. In the illustrated arrangement, the mask seal 2104 or mask shell 2102 comprises a mounting post 2270 and the strap 2182 comprises an opening 2272 through which the mounting post 2270 can pass. An enlarged retaining portion or head of the mounting post 2270 can retain the strap 2182 in place once the strap 2182 is assembled onto the mounting post 2270. In other configurations, this arrangement could be reversed. Other suitable arrangements can also be used, such as a tab/slot arrangement, snap-fit or hook-and-bar arrangement. In still other configurations, the strap 2182 can be attached to the headgear 2180, such as to the upper straps 2260 on each side of the interface assembly. The strap 2182 can be adjustable relative to the mask assembly 2100 to adjust an effective length of the strap 2182 and thereby adjust the amount of support or deflection provided to the paddles 2126. For example, the strap 2182 could be provided with multiple openings 2272 or other mounting elements on each side.

Although illustrated in connection with a nasal-oral mask assembly 2100, the features and advantages of the paddles 2126, support structures 2163 and paddle covers 2182 can be utilized with other types of masks, as well. FIGS. 40-43 illustrate a nasal mask assembly 3100 comprising features similar to the paddles 2126, support structures 2163 and paddle covers 2182 described above. The nasal mask assembly 3100 is described in the context of the differences relative to the previously-described nasal-oral masks. Therefore, features, components or other structures not explicitly described can be the same as or similar to the same or corresponding features, component or structures of the mask assemblies 2100 disclosed herein, or can be of any other suitable arrangement.

The illustrated mask assembly 3100 comprises a mask support, which can be a base, housing or shell 2102, for example. A mask seal 2104 can be attached to the mask shell 2102 such that the mask shell 2102 provides some amount of support for the mask seal 2104. The mask assembly 3100 can be engaged with or otherwise supported by a frame 2178 that allows for connection to a headgear of any suitable arrangement (such as headgear 2180). In the illustrated arrangement, the mask shell 2102 is in the form of a connector that permits the mask assembly 3100 to be connected to the frame 2178. The illustrated mask shell 2102 is generally annular in shape and, in at least some configurations, does not cover a substantial portion of a forward-facing surface of the mask seal 2104. In some configurations, the headgear could be coupled directly to the mask assembly 3100 and the frame 2178 can be utilized for other purposes or omitted. A conduit connector, such as an elbow 2106, can also be attached to the mask shell 2102, frame 2178 or otherwise supported relative to and adapted to communicate with an interior space of the mask assembly 3100. Together, the frame 2178 and the headgear 2180 can support the mask assembly 3100 in place on the user's face. Collectively, the mask assembly 3100, frame 2178 and headgear 2180 can be referred to as an interface assembly. The mask assembly 3100 or the mask assembly 3100 in combination with the frame 2178 can be referred to as an interface.

The frame 2178 can be removably connected to the mask assembly 3100 by any suitable arrangement. For example, the frame 2178 can be coupled at or around the aperture 2114 of the mask shell 2102, such as by a snap fit, friction fit or clip connection, among other possibilities. The mask assembly 3100 can be keyed to the frame 2178 to permit assembly in only the correct orientation. The conduit connector 2106 can also be attached to the mask shell 2102, frame 2178 or otherwise supported relative to and adapted to communicate with an interior space of the mask assembly 3100. For example, but without limitation, the connector 2106 can be connected to the shell 2102 such that the connector 2106 can swivel, pivot or rotate relative to the shell 2102 about a single axis or about multiple axes. In some configurations, the connector 2106 can define a portion of a ball joint with the frame 2178 and/or mask shell 2102, for example but without limitation, defining the other portion. The ball joint can have any suitable configuration. The connector 2106 facilitates connection to a gases conduit, such as a supply conduit or the like for the supply of pressurized breathing gases to an interior of the mask assembly 3100. Any suitable connector 2106 can be used, which in some cases can include a swivel or rotational coupling that permits relative rotation between the connector 2106 and the gases conduit.

In the illustrated configuration, the connector 2106 comprises an elbow, such as a polycarbonate elbow for example but without limitation, that contains a vent. In the illustrated arrangement, the vent comprises bias flow holes 2110. However, the vent could comprise other geometries or arrangements, such as slots or a controlled leak between components, for example. The vent could also comprise diffuser materials to reduce noise and/or draft. The bias flow holes 2110 are a collection of orifices that are configured to exhaust air and flush CO2 to reduce the likelihood of rebreathing expired carbon dioxide by the user. While the bias flow holes 2110 are shown exclusively on the connector 2106, in some configurations, the bias flow holes 2110 can be provided on the mask shell 2102, on the mask seal 2104 or on any combination of the connector 2106, the shell 2102 and the seal 2104 or on any other component of the interface assembly or associated breathing circuit. The bias flow holes 2110 can have any suitable cross-section and can be cylindrical, hour-glass shaped, tapered in either direction, fully or partially tapered, fully or partially cylindrical, contoured to vary in cross-section or the like.

The illustrated seal 2104 is configured to seal under the nose of the user, along a portion of the face extending lateral to the nose, as well as along the upper lip of the user. The mask assembly 3100 advantageously does not require contact with the bridge of the nose of the user. In the illustrated configuration, the mask assembly 3100 does not extend over the bridge of the nose of the user. More particularly, the illustrated mask assembly 3100 does not contact the bridge of the nose of the user.

The mask assembly 3100 may or may not extend over the tip of the nose of the user. Thus, in some configurations, the mask assembly 3100 covers the tip of the nose. In some configurations, the seal of the mask assembly 3100 covers the tip of the nose. In some configurations, the illustrated mask assembly 3100 preferably does not enshroud the tip of the nose of the user. In some configurations or with some facial geometries, the tip of the nose of the user extends over the adjoining portion of the mask assembly 3100. In some configurations, the frame 2178 and other portions of the mask assembly 3100 can accommodate deflection of the mask seal 2104 by portions (e.g., the tip) of the user's nose such that the interface can accommodate a variety of nasal lengths.

As illustrated, the mask assembly 3100 preferably is adapted to extend around and seal over the wing or alar of the nose, which flares out to form a rounded eminence around the nostril. The illustrated mask assembly 3100 is adapted to seal around the surfaces that define the opening to the nostril, which may include a portion or entirety of the fleshy external end of the nasal septum, sometimes called the columella. In some configurations, the mask assembly 3100 is adapted to extend upwardly to seal along at least a portion of the left and right dorsal side walls of the nose of the user. In some configurations, the mask assembly 3100 is adapted to extend upwardly along at least a portion of the left and right dorsal side walls without extending upwardly to the region of the bridge of the nose of the user. In some configurations, a primary sealing surface of the mask assembly 3100 contacts the underside of the nose of the user, the upper lip and/or a transition region between the underside of the nose and the upper lip. A secondary sealing surface of the mask can contact the side surfaces of the nose of the user, possibly along with the cheeks at a location near the nose. Such primary and secondary sealing surfaces may not make contact with the face of all users; however, such an arrangement can provide a suitable seal with a relatively large range of facial geometries.

The mask seal 2104 comprises at least one nasal opening 2124. In some configurations, the mask seal 2104 can comprise more than one nasal opening 2124. In some configurations, the mask seal 2104 can comprise nasal openings 2124 defined within superstructures, such as pillows, prongs or the like. In some configurations, the nasal opening 2124 can be defined by a nasal cushion or insert, which can be overmolded or otherwise secured to a base structure of the mask seal 2104. Examples of suitable arrangements of the mask seal 2104 are disclosed in Applicant's publication no. WO 2014/077708, the entirety of which is incorporated by reference herein.

The mask seal 2104 comprises an inward or rearward-facing central portion 3102 that faces or contacts the user during use of the mask assembly 3100. The mask seal 2104 also comprises a pair of opposing inner lateral portions 3104 and a pair of opposing outer lateral portions 3106. The inner lateral portions 3104 are configured to contact the sides of the nose and/or the portion of the user's face on either side of the nose. The inner lateral portions 3104 can comprise both inward-facing surfaces and rearward-facing surfaces. That is, each of the inner lateral portions 3104 can wrap from an inward-facing surface of the mask seal 2104 toward or to a rearward-facing surface of the mask seal 2104. The outer lateral portions 3106 can comprise both rearward-facing surfaces and outward-facing surfaces. The rearward-facing surfaces of the outer lateral portions 3106 can contact the face of the user during use of the mask assembly 3100. The mask seal 2104 can also comprise a nasal opening support 3108 that partially or completely surrounds and provides support to the nasal opening 2124.

Similar to the mask seals 2104 described above with respect to FIGS. 1-39, the mask seal 2104 of FIGS. 40-43 can comprise regions of varying thickness to provide the mask seal 2104 with different properties or characteristics within the different regions. For example, the central portion 3102 can have a relatively low thickness to allow the central portion 3102 to conform to the particular facial geometry of the user. In some configurations, the relatively low thickness can allow the central portion 3102 to stretch. In some configurations, the central portion 3102 can have a thickness between 0.3 mm and 0.5 mm or 0.6 mm. In some configurations, the thickness of the central portion 3102 is 0.3 mm. If desired, the central portion 3102 could have a thickness as low as 0.15 mm. However, it has been determined that lower thicknesses can result in or increase the likelihood of creasing for some facial geometries and/or under some operational gas pressures. Keeping the thickness at or above 0.3 mm in a substantial portion or an entirety of the central portion 3102 can reduce the incidence of creasing over a substantial range of operational pressures, which may comprise an entire range of normal operating pressures.

The inner lateral portions 3104 can have a thickness that is greater than the thickness of the central portion 3102. In some configurations, the thickness of the inner lateral portions 3104 can be between 0.4 mm and 0.6 mm. In some configurations, the thickness of the inner lateral portions 3104 is 0.5 mm. The nasal opening support 3108 can have a thickness that is greater than one or both of the central portion 3102 and the inner lateral portions 3104. The relatively greater thickness can protect the mask seal 2104 from tearing at the nasal opening 2124 and can help the nasal opening 2124 maintain an opened shape. In some configurations, the thickness of the nasal opening support 3108 is between 1 mm and 2.5 mm. In some configurations, the thickness of the nasal opening support 3108 is 1.2 mm. The thicknesses can be constant or varied within any of the central portion 3102, inner lateral portions 3104 or nasal opening support 3108.

The lateral portions 2126 of the mask assembly 3100, including portions or entireties of the inner lateral portions 3104 and the outer lateral portions 3106, can function in the same or similar manner as the paddles 2126 of the mask assembly 2100. Accordingly, the lateral portions 2126 of the mask assembly 3100 can be referred to herein as paddles. Paddles 2126 can refer to any portion of an interface seal that is positioned alongside the nose of the user during use of the interface. Paddles 2126 are disclosed in the context of under-nose interfaces herein, but can be utilized in other types of interfaces, including those that contact, cover or seal against the bridge of the user's nose, unless otherwise indicated.

The outer lateral portions 3106 can comprise features that assist in maintaining a shape of the mask seal 2104. In some configurations, the outer lateral portions 3106 comprise regions of increased thickness, rigidity or stiffness that assist in maintaining a shape of the mask seal 2104. Such features can be similar in structure and/or function to the support structures 2163 described herein with respect to the paddles 2126 of the mask assemblies 2100. Accordingly, the same reference number is used to refer to both the support structures 2163 of the mask assembly 3100 and the support structures 2163 of the mask assemblies 2100. The support structures 2163 of the mask assembly 3100 can inhibit or prevent overexpansion or undesired expansion of the lateral end portions of the mask seal 2104, which could result in leaks and/or undesirable pressure being applied to the user's nose by the central portion 3102 of the mask seal 2104, in a manner similar to that described above with respect to the paddles 2126. Similarly, the support structures 2163 can inhibit or prevent collapse of at least portions of the mask seal 3100 when engaged with a nose in use. For example, the support structures 2163 can inhibit or prevent collapse of the nasal region or central portion 3102 of the mask seal 3100.

The support structures 2163 can also transfer forces from one portion of the mask seal 2104 to another portion of the mask seal 2104. For example, the support structures 2163 can transfer force applied to a rear portion of the mask seal 2104 to a front portion of the mask seal 2104. In some configurations, the support structures 2163 can transfer force applied to a rearward-facing surface of the mask seal 2104 by the user's face to another portion of the mask seal 2104 that can resist some or all of the transferred force. In some configurations, the support structures 2163 transfer force from a rearward-facing or user-contacting surface of the mask seal 2104 to the frame 2178 or other structure that supports the mask seal 2104 (e.g., the mask shell 2102). Thus, in some configurations, the support structures 2163 extend between a rearward-facing surface of the mask seal 2104 and a surface of the mask seal 2104 that contacts or is overlapped by the frame 2178 or other support structure for the mask seal 2104. Preferably, the support structures extend from the rearward-facing surface to the surface that is overlapped by the frame 2178 or other support structure. However, as noted above, the support structures 2163 can provide structure to the mask seal 2104 and can be utilized to provide such support without necessarily transferring forces.

In some configurations, the frame 2178 includes a central portion and lateral portions on each side of the central portion. The lateral portions can function in a manner similar to or the same as the paddle covers 2182 described with respect to the interfaces of FIGS. 1-39. Accordingly, the same reference number used to indicate the paddle covers 2182 is used to indicate the lateral portions 2182 of the frame 2178. Moreover, references to paddle covers 2182 can also refer to the lateral portions 2182 of the frame 2178 of FIG. 40 unless otherwise indicated. The lateral portions or paddle covers 2182 can be aligned with or overlap the portions of the mask seal 2104 comprising the support structures 2163 such that the support structures 2163 can transfer loads to the lateral portions 2182 of the frame 2178 in a manner similar to or the same as described above with reference to FIGS. 1-39.

The supports 2163 can extend in a direction generally from the rearward or user-contacting surface of the mask seal 2104 toward its respective lateral portion of cover 2182 of the frame 2178. In some configurations, each of the supports 2163 extends generally or substantially in a longitudinal direction of the mask seal 2104. The supports 2163 can extend generally parallel to one another or can be closer at a forward end in comparison to a rearward end. In other words, the supports 2163 can converge in a direction moving from the rearward or user-contacting surface of the mask seal 2104 toward a front portion of the mask seal 2104. However, in other configurations, the supports 2163 can diverge from rear to front.

In the illustrated arrangement, each support structure 2163 is shaped or otherwise configured to follow a portion or an entirety of a peripheral edge of the associated outer lateral portion 3106. Each support structure 2163 can comprise a general C-shape (or reversed C-shape) when the mask seal 2104 is viewed from the side, which comprises a rearward portion 3110 and an upper extension or leg 3112 and a lower extension or leg 3114 that extend forward from the rearward portion 3110. In the illustrated arrangement, the support structures 2163 are thickened regions of the mask seal 2104, each of which projects inwardly into the interior space of the mask seal 2104. Either one or both of the extensions 3112, 3114 can extend to and/or contact the mask shell 2102. In the illustrated configuration, only the lower extension 3112 extends to the mask shell 2102 and the upper extension 3112 is spaced rearward from the mask shell 2102. However, in other configurations, this arrangement could be reversed.

Each of the illustrated support structures 2163 comprises a cut-out or relief 3120 that provides a region of less thickness, stiffness or rigidity within the support structure 2163. In the illustrated arrangement, the relief 3120 is a region of less thickness relative to other portions of the support structure 2163. The illustrated relief 3120 also comprises a general C-shape (or reverse C-shape) when the mask seal 2104 is viewed from the side. In some configurations, the relief 3120 also follows a portion or an entirety of a peripheral edge of the associated outer lateral portion 3106. However, preferably, the relief 3120 is spaced inwardly from the peripheral edge of the outer lateral portion 3106. In at least some configurations, the relief 3120 is fully contained within the support structure 2163. The relief 3120 can allow portions of the support structure 2163 to move relative to one another. Accordingly, the relief 3120 can allow corresponding portions of the mask seal 2104 to move relative to one another. Thus, a portion of the support structure 2163 and mask seal 2104 rearward of the relief 3120 can move toward a portion of the support structure 2163 and mask seal 2104 forward of the relief 3120.

The support structure 2163 can be of variable thickness to provide different levels of support to the mask seal 2104. For example, the upper extension 3112 and/or lower extension 3114 can have a thickness that is less than a thickness of at least a portion of the rearward portion 3110. In some configurations, a portion of the rearward portion 3110 rearward of the relief 3120 and/or located on or adjacent a rearward surface of the mask seal 2104 has a thickness that is greater than a portion of the rearward portion 3110 forward of the relief 3120. The relief 3120 can have a thickness that is less than both the portion of the rearward portion 3110 forward of the relief 3120 and the portion of the rearward portion 3110 rearward of the relief 3120. Furthermore, a portion of the outer lateral portions 3106 outside (e.g., forward) of the support structure 2163 can have a thickness that is less than a thickness of any portion of the support structure 2163. In some configurations, the thickness of the portion of the outer lateral portions 3106 outside of the support structure 2163 is equal to or substantially equal to the thickness of the relief 3120.

In some configurations, the portion of the rearward portion 3110 rearward of the relief 3120 and/or located on or adjacent a rearward surface of the mask seal 2104 has a thickness of between 2 mm and 5 mm. In some configurations, the thickness is 4 mm. In some configurations, the portion of the rearward portion 3110 forward of the relief 3120 has a thickness of between 1.5 mm and 3 mm. In some configurations, the thickness is 2 mm. In some configurations, the relief 3120 has a thickness between 0.3 mm and 0.6 mm. In some configurations, the thickness is 0.5 mm. In some configurations, the portion of the outer lateral portions 3106 outside of the support structure 2163 can have a thickness of between 0.3 mm and 0.6 mm. In some configurations, the thickness is 0.5 mm. The mask seal 2104 can also have thicknesses proportional to those disclosed herein, without having any or all of the particular thicknesses disclosed.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A mask assembly for use in providing positive pressure respiratory therapy, the mask assembly comprising:
    a mask seal comprising a wall having an inner surface opposite an outer surface and a wall thickness defined between the inner surface and outer surface, the mask assembly also comprising a mask shell, the mask seal being connected to the mask shell;
    the mask assembly being configured to be fully positioned lower than a bridge of a nose of a face of a user, the mask assembly also being configured to provide an exposed bridge of the nose of the user;
    the mask seal comprising a nasal region comprising at least one nasal opening, the mask seal further comprising an upper front portion positioned vertically higher than the mask shell, the upper front portion extending in a lateral direction across a front side of the mask seal, the nasal region of the mask seal comprising an upper surface defined by a central portion of an outer surface of the mask seal, a first paddle extending upward relative to the upper surface on a first side of the nasal region and a second paddle extending upward relative to the upper surface on a second side of the nasal region, the first paddle comprising a first upper ridge at a vertical apex of the first paddle, the second paddle comprising a second upper ridge at a vertical apex of the second paddle, the first paddle being configured to contact a first side of the nose of the user and the second paddle configured to contact the other a second side of the nose of the user, the upper surface being located between the first paddle and the second paddle;
    a wall surface of the first paddle comprising a first elongate area of increased wall thickness relative to the upper surface of the nasal region and a wall surface of the second paddle comprising a second elongate area of increased wall thickness relative to the upper surface of the nasal region, each of the first elongate area of increased wall thickness and the second elongate area of increased wall thickness comprising a generally triangular shape with a base of the generally triangular shape being positioned closer to the face of the user than a tip of the generally triangular shape, the first elongate area of increased wall thickness and the second elongate area of increased wall thickness extending in a fore-aft direction between a first end and a second end, the first elongate area of increased wall thickness extending along the first upper ridge of the first paddle, the second elongate area of increased wall thickness extending along the second upper ridge of the second paddle, the first elongate area of increased wall thickness joining a first laterally outward-facing surface portion of the first paddle and a first laterally inward-facing surface portion of the first paddle, the second elongate area of increased wall thickness joining a second laterally outward-facing surface portion of the second paddle and a second laterally inward-facing surface portion of the second paddle, and each of the first laterally inward-facing surface portion and the second laterally inward-facing surface portion having a curved shape that is concave facing an interior of the mask seal.

2. The mask assembly of claim 1, wherein the wall thickness in the nasal region is thinner than any other portion of the mask seal.

3. The mask assembly of claim 1, wherein the first elongate area of increased wall thickness and the second elongate area of increased wall thickness are thicker than any other portion of the mask seal.

4. The mask assembly of claim 1, wherein the first elongate area of increased wall thickness and the second elongate area of increased wall thickness extend from a user-contacting surface of the mask seal toward the mask shell.

5. The mask assembly of claim 1, wherein the first elongate area of increased wall thickness and the second elongate area of increased wall thickness are connected to form a connected area of increased wall thickness.

6. The mask assembly of claim 1, wherein the mask seal further comprises an oral opening, wherein a wall thickness surrounding the oral opening is as thin as or thinner than any other portion of the mask seal.

7. The mask assembly of claim 6, wherein the mask seal further comprises outer peripheral portions on either side of the oral opening, wherein each of the outer peripheral portions wrap from a rear-facing side of the mask seal around to at least a portion of a laterally-facing side of the mask seal, wherein a wall thickness in each of the outer peripheral portions is greater than a wall thickness in the nasal region.

8. An interface assembly comprising the mask assembly of claim 1, wherein the interface assembly further comprises a removably attachable frame, wherein the removably attachable frame comprises one or more covers that extend from the removably attachable frame and are configured to prevent the mask seal from expanding outwardly and losing shape when pressurized air is introduced into the mask seal.

9. The interface assembly of claim 8, wherein each of the first elongate area of increased wall thickness and the second elongate area of increased wall thickness is aligned with a respective one of the one or more covers and is configured to transfer load from the mask seal to the one or more covers.

10. An interface assembly comprising the mask assembly of claim 1, wherein the interface assembly further comprises a removably attachable frame, wherein the removably attachable frame comprises a pair of covers supported relative to the mask assembly such that each of the pair of covers is positioned adjacent a portion of a respective one of the first paddle and the second paddle, wherein the pair of covers limit expansion of at least the portion of the first paddle and the second paddle.

11. The interface assembly of claim 10, wherein the pair of covers are unitarily formed with the removably attachable frame.

12. The interface assembly of claim 11, wherein each of the first elongate area of increased wall thickness and the second elongate area of increased wall thickness is aligned with a respective one of the pair of covers and is configured to transfer load from the mask seal to the pair of covers.

13. The interface assembly of claim 10, wherein the pair of covers are positioned adjacent only a first portion of the first paddle and the second paddle leaving a second portion of the first paddle and the second paddle exposed.

14. The interface assembly of claim 13, wherein each of the first elongate area of increased wall thickness and the second elongate area of increased wall thickness is aligned with a respective one of the pair of covers and is configured to transfer load from the mask seal to the pair of covers.

15. The interface assembly of claim 13, wherein the first elongate area of increased wall thickness and the second elongate area of increased wall thickness in the first paddle and the second paddle is thicker than all other portions of the mask seal in the first paddle and the second paddle and the nasal region.

16. The interface assembly of claim 15, wherein each of the first elongate area of increased wall thickness and the second elongate area of increased wall thickness is aligned with a respective one of the pair of covers and is configured to transfer load from the mask seal to the pair of covers.

17. The mask assembly of claim 1, wherein the first elongate area of increased wall thickness and the second elongate area of increased wall thickness in each of the first paddle and the second paddle is greater than a wall thickness in adjacent portions of the first laterally outward-facing surface portion, the second laterally outward-facing surface portion, the first laterally inward-facing surface portion, and the second laterally inward-facing surface portion.

18. The mask assembly of claim 1, wherein an entirety of each of the first elongate area of increased wall thickness and the second elongate area of increased wall thickness is located within a respective one of the first paddle and the second paddle.

19. The mask assembly of claim 1, wherein an entirety of each of the first elongate area of increased wall thickness and the second elongate area of increased wall thickness is positioned superior of the at least one nasal opening.

20. The mask assembly of claim 1, wherein each one of the first paddle and the second paddle comprises a paddle height measured vertically higher than the upper surface of the mask seal.

21. The mask assembly of claim 1, wherein the first end of each of the first elongate area of increased wall thickness and the second elongate area of increased wall thickness is located in a forward-facing wall of the mask seal and the second end of each of the first elongate area of increased wall thickness and the second elongate area of increased wall thickness is located in a rearward-facing wall of the mask seal.

22. The mask assembly of claim 21, wherein the first elongate area of increased wall thickness and the second elongate area of increased wall thickness are configured to transfer force from a rearward-facing wall of each of the first paddle and the second paddle to a forward-facing wall of each of the first paddle and the second paddle.

* * * * *

UNITED STATES PATENT AND TRADEMARK OFFICE
CERTIFICATE OF CORRECTION

| | | |
|---|---|---|
| PATENT NO. | : 11,701,486 B2 | |
| APPLICATION NO. | : 15/316814 | |
| DATED | : July 18, 2023 | |
| INVENTOR(S) | : Fadi Karim Moh'd Mashal et al. | |

It is certified that error appears in the above-identified patent and that said Letters Patent is hereby corrected as shown below:

In the Specification

Column 3, Line 28, delete "seal" and insert -- seal. --.

Column 7, Line 21, delete "users," and insert -- users; --.

Column 15, Line 24, delete "cmH2O)." and insert -- cm H2O). --.

Column 35, Line 65, delete "that that" and insert -- that --.

In the Claims

Column 36, Line 50, Claim 1, after "contact" delete "the other".

Signed and Sealed this
Twenty-first Day of November, 2023

Katherine Kelly Vidal
*Director of the United States Patent and Trademark Office*